United States Patent
Kelly et al.

(10) Patent No.: US 7,402,596 B2
(45) Date of Patent: Jul. 22, 2008

(54) BICYCLOHETEROARYL COMPOUNDS AS P2X7 MODULATORS AND USES THEREOF

(75) Inventors: Michael G. Kelly, Thousand Oaks, CA (US); John Kincaid, San Mateo, CA (US)

(73) Assignee: Renovis, Inc., South San Francisco, CA (US)

( * ) Notice: Subject to any disclaimer, the term of this patent is extended or adjusted under 35 U.S.C. 154(b) by 192 days.

(21) Appl. No.: 11/384,199

(22) Filed: Mar. 17, 2006

(65) Prior Publication Data

US 2007/0197565 A1 Aug. 23, 2007

Related U.S. Application Data

(60) Provisional application No. 60/753,194, filed on Dec. 22, 2005, provisional application No. 60/721,390, filed on Sep. 28, 2005, provisional application No. 60/712,778, filed on Aug. 31, 2005, provisional application No. 60/710,077, filed on Aug. 22, 2005, provisional application No. 60/709,186, filed on Aug. 18, 2005, provisional application No. 60/664,903, filed on Mar. 24, 2005.

(51) Int. Cl.
C07D 211/74 (2006.01)
A61K 31/47 (2006.01)

(52) U.S. Cl. ........................ 514/309; 546/141
(58) Field of Classification Search .......... 546/141; 514/309
See application file for complete search history.

(56) References Cited

U.S. PATENT DOCUMENTS

| | | | |
|---|---|---|---|
| 2,640,829 | A | 6/1953 | Wilson et al. |
| 3,978,066 | A | 8/1976 | Philipp et al. |
| 6,380,193 | B1 | 4/2002 | Li et al. |
| 2005/0267202 | A1 | 12/2005 | Nguyen et al. |
| 2005/0277643 | A1 | 12/2005 | Kelly et al. |
| 2006/0135557 | A1 | 6/2006 | Nan et al. |

FOREIGN PATENT DOCUMENTS

| | | |
|---|---|---|
| EP | 482939 A1 | 4/1992 |
| WO | WO 99/21836 | 5/1999 |
| WO | WO 00/42040 | 7/2000 |
| WO | WO 01/87855 | 11/2001 |
| WO | WO 02/094790 | 11/2002 |
| WO | WO 03/011285 | 2/2003 |
| WO | WO 03/080578 | 10/2003 |
| WO | WO 03/082827 | 10/2003 |
| WO | WO 03/093249 | 11/2003 |
| WO | WO 03/099274 | 12/2003 |
| WO | WO 2004/078176 | 9/2004 |
| WO | WO 2004/108724 | 12/2004 |
| WO | WO 2005/034939 | 4/2005 |
| WO | WO 2005/035503 | 4/2005 |
| WO | WO 2005/066171 | 7/2005 |
| WO | WO 2005/075429 | 8/2005 |
| WO | WO 2005/105814 | 11/2005 |
| WO | WO 2006/030032 | 3/2006 |
| WO | WO 2006/050998 | 5/2006 |
| WO | WO 2006/057270 | 6/2006 |
| WO | WO 2006/066950 | 6/2006 |

OTHER PUBLICATIONS

Electron Impact Induced Loss of C-5/C-8 Substituents of 1,2,3,4,-Tetrahydroisoquinolines, VI[1)]: Snythesis and Mass Spectrometric Fragmentation of Dihydroindole Derivatives*)**); 1990, Arch. Pharm. 323, pp. 145-155.

Abstract Only of: Ponomarev, O.A. et al., Acid-base reactions of 1(2H)-isoquinolinone derivatives in the ground and excited states; 1989; Zhurnal Osbschei Khimii 59(6).

Abstract Only of: Doroshenko, A.O., et al., A theoretical approach to the problem of the search for effective luminophors in the isocarbostyril series; 1988; Teoreticheskaya i Eksperimental'naya Khimiya; 24(4).

Chan, WN, et al., Evaluation of a Series of Anticonvulsant 1,2,3,4-Tetrahydrolsoquinollnyl-benzamides, 2000, Bioorganic & Medical Chemistry, vol. 8, pp. 2085-2094.

*Primary Examiner*—Zinna N Davis
(74) *Attorney, Agent, or Firm*—Klauber & Jackson, LLC

(57) ABSTRACT

Bicycloheteroaryl compounds are disclosed that have a formula represented by the following:

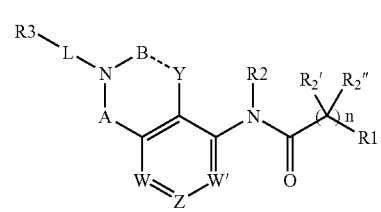

The compounds may be prepared as pharmaceutical compositions, and may be used for the prevention and treatment of a variety of conditions in mammals including humans, including by way of non-limiting example, pain, inflammation, traumatic injury, and others.

41 Claims, No Drawings

BICYCLOHETEROARYL COMPOUNDS AS P2X7 MODULATORS AND USES THEREOF

CROSS REFERENCE TO RELATED APPLICATIONS

The present application claims the priority of co-pending provisional applications U.S. Ser. No. 60/664,903, filed on Mar. 24, 2005; U.S. Ser. No. 60/709,186 filed on Aug. 18, 2005; U.S. Ser. No. 60/710,077 filed on Aug. 22, 2005; U.S. Ser. No. 60/712,778 filed on Aug. 31, 2005; U.S. Ser. No. 60/721,390 filed on Sep. 28, 2005; and U.S. Ser. No. 60/753,194 filed on Dec. 22, 2005. The disclosures of all of the aforementioned applications are incorporated by reference herein in their entireties. Applicants claim the benefits of these applications under 35 U.S.C. §119(e).

FIELD OF THE INVENTION

This invention relates to novel compounds of the class bicycloheteroaryls that are capable of modulating $P2X_7$ receptor activity, and to pharmaceutical compositions containing such compounds. This invention also relates to methods for preventing and/or treating conditions that are causally related to aberrant $P2X_7$ activity, such as inflammation-related conditions in mammals, comprising (but not limited to) rheumatoid arthritis, osteoarthritis, Parkinson's disease, uveitis, asthma, cardiovascular conditions including myocardial infarction, the treatment and prophylaxis of pain syndromes (acute and chronic or neuropathic), traumatic brain injury, acute spinal cord injury, neurodegenerative disorders, inflammatory bowel disease and autoimmune disorders, using the compounds and pharmaceutical compositions of the invention.

BACKGROUND OF THE INVENTION

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members ($P2X_1$-$P2X_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three primary ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, which has been interpreted to indicate that $ATP^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor ($rP2X_7$) thus corresponds to the P2Z receptor. $rP2X_7$ is structurally related to other members of the P2X family but it has a longer cytoplasmic C-terminus domain (there is 35-40% amino acid identity in the corresponding region of homology, but the C-terminus is 239 amino acids long in the $rP2X_7$ receptor compared with 27-20 amino acids in the others). The $rP2X_7$ receptor functions both as a channel permeable to small cations and as a cytolytic pore. Brief applications of ATP (1-2s) transiently open the channel, as is the case of other P2X receptors. Repeated or prolonged applications of agonist cause cell permeabilization reducing the extracellular magnesium concentration potentiates this effect. The unique C-terminal domain of $rP2X_7$ is required for cell permeabilization and the lytic actions of ATP (Suprenant et al, Science 272:735 (1996)).

The $P2Z/rP2X_7$ receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). Certain functional differences exist between rodent and man (Hickman et al, Blood 84:2452 (1994)). The human macrophage $P2X_7$ receptor ($P2X_7$) has now been cloned and its functional properties determined (Rassendren et al, J. Biol. Chem. 272:5482 (1997). When compared with the rat $P2X_7$ receptor, elicited cation-selective currents in the human $P2X_7$ receptor required higher concentrations of agonists, were more potentiated by removal of extracellular magnesium ions, and revised more rapidly on agonist removal. Expression of chimeric molecules indicated that some of the differences between rat and human $P2X_7$ receptors could be revised by exchanging the respective C-terminal domains of the receptor proteins.

It has been reported that certain compounds act as $P2X_7$ antagonists. For example, WO99/29660 and WO99/29661 disclose that certain adamantane derivatives exhibit $P2X_7$ antagonistic activity having therapeutic efficacy in the treatment of rheumatoid arthritis and psoriasis. Similarly, WO99/29686 discloses that certain heterocyclic derivatives are $P2X_7$ receptor antagonists and are useful as immunosuppressive agents and treating rheumatoid arthritis, asthma, septic shock and atheroscelerosis. Finally, WO00/71529 discloses certain substituted phenyl compounds exhibiting immunosuppressing activity. All of the references described herein are incorporated herein by reference in their entirety.

A need therefore exists for therapeutic agents, and corresponding pharmaceutical compositions and related methods of treatment, that address the conditions causally related to aberrant $P2X_7$ activity, and it is toward the fulfillment and satisfaction of that need, that the present invention is directed.

SUMMARY OF THE INVENTION

Bicycloaryl derivatives of formulas I-IIIa, and their pharmaceutical compositions are disclosed as therapeutic agents useful for the treatment of conditions in mammals associated with abnormal or aberrant activity of the $P2X_7$ receptor, including inflammatory-mediated conditions such as (but not limited to) arthritis, myocardial infarction, the treatment and prophylaxis of pain syndromes (acute and chronic [neuropathic]), traumatic brain injury, acute spinal cord injury, neurodegenerative disorders, inflammatory bowel disease and immune dysfunctions such as autoimmune disorders.

It has now been found that the present bicycloheteroaryl compounds are capable of mediating the activity of the $P2X_7$ receptor. This finding leads to novel compounds having therapeutic value. It also leads to pharmaceutical compositions having the compounds of the present invention as active ingredients and to their use to treat, prevent or ameliorate a range of conditions in mammals such as but not limited to inflammation of various genesis or etiology, for example rheumatoid arthritis, cardiovascular disease, inflammatory bowel disease, acute, chronic, inflammatory and neuropathic pain, dental pain and headache (such as migraine, cluster headache and tension headache) and other conditions causally related to inflammation or immune dysfunction.

The compounds of the present invention are also useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, uveitis, asthma, myocardial infarction, traumatic brain injury, spinal cord injury, neurodegenerative disorders, inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides bicycloheteroaryl compounds which are capable of modulating the activity of the $P2X_7$ receptor, in vivo. In a further aspect, the compounds of the invention are capable of antagonizing (suppressing or inhibiting) the activity of the $P2X_7$ receptor, and thereby treating those conditions, representative ones of which are causally related to aberrant $P2X_7$ activity.

Accordingly, in a first aspect of the invention, bicycloheteroaryl compounds are disclosed that are capable of modulating the activity of the $P2X_7$ receptor in vivo, having a formula (I):

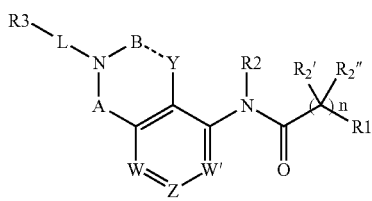

wherein

A is selected from $CR^{2'}R^{2''}$, CO, and CS;

B is selected from $CR^{2'}$, $CR^{2'}R^{2''}$, CO, and CS;

Y is independently selected from $CR^{2'}$ and $CR^{2'}R^{2''}$;

W, W' and Z are independently selected from $CR^4$ and N, provided that all three of W, W' and Z can not be N at the same time;

L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl which can be optionally substituted by a substituent selected from hydroxyl, halogen and $C_1$-$C_6$ alkoxy;

n is 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido; each of $R^2$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;

$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

and the dotted bond is a single or a double bond;

or a pharmaceutically acceptable salt, solvate or prodrug thereof;

and stereoisomers and tautomers thereof.

In one particular embodiment, A is CO or CS.

In a further embodiment, with respect to compounds of formula I, n is 0.

In a further embodiment, with respect to compounds of formula I, L may be a bond and $R^3$ is selected from H, acyl, substituted acyl, substituted or unsubstituted aminocarbonyl, alkoxycarbonyl, substituted alkoxycarbonyl, substituted or unsubstituted sulfoxide, substituted or unsubstituted sulfone, substituted or unsubstituted aminosulfonyl, substituted or unsubstituted arylsulfonyl, aryloxycarbonyl, substituted aryloxycarbonyl, heteroaryloxycarbonyl, and substituted heteroaryloxycarbonyl.

In a further embodiment, with respect to compounds of formula I, L is $L^1$; and wherein $L^1$ is a bond, or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy. In one particular embodiment, when A is CO or CS, $L^1$ is a bond or $C_1$-$C_5$ alkylene group.

In a further embodiment, with respect to compounds of formula I, L is $L^1$; and wherein $L^1$ is a bond, a $C_1$-$C_5$ alkylene group; and $R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl. In one particular embodiment, when $R^3$ is hydrogen $L^1$ is a bond or a $C_1$-$C_5$ alkylene group.

In a further embodiment, with respect to compounds of formula I, A is CO; and B and Y are independently selected from $CR^{2a}$ and $CR^{2a}R^{2b}$.

In a further embodiment, with respect to compounds of formula I, A is CO; B and Y may all represent $CH_2$ and $R^2$ represents hydrogen.

In a further aspect, the present invention provides pharmaceutical compositions comprising a bicycloheteroaryl compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. inflammation, such as rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction, including autoimmune disorders, which method comprises administering an effective amount of one or more of the pharmaceutical compositions just described.

In yet another method of treatment aspect, this invention provides a method of treating a mammal susceptible to or afflicted with a condition that is causally related to aberrant $P2X_7$ receptor activity, and that for example, gives rise to pain responses or that relates to imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with conditions that are causally related to abnormal activity of the $P2X_7$ receptor, such as neurodegenerative diseases and disorders including, for example, Parkinson's disease, multiple sclerosis; diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and cardiovascular and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of the $P2X_7$ receptor and thus avert or treat any maladies that may be causally related thereto.

It is further an object of this invention to provide a series of compounds that can treat or alleviate maladies or symptoms of same, such as pain and inflammation, that may be causally related to the activation of the $P2X_7$ receptor.

A still further object of this invention is to provide pharmaceutical compositions that are effective in the treatment or prevention of a variety of disease states, including the diseases associated with the central nervous system, cardiovascular conditions, chronic pulmonary obstructive disease COPD), inflammatory bowel disease, rheumatoid arthritis, osteoarthritis, and other diseases where an inflammatory component is present.

Other objects and advantages will become apparent to those skilled in the art from a consideration of the ensuing detailed description.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that, consistent with the scope of the present invention, any of the moieties defined herein and/or set forth below may be substituted with a variety of substituents, and that the respective definitions are intended to include such substituted moieties within their scope. By way of non-limiting example, such substituents may include e.g. halo (such as fluoro, chloro, bromo), —CN, —CF_3, —OH, —OCF_3, $C_2$-$C_6$ alkenyl, $C_3$-$C_6$ alkynyl, $C_1$-$C_6$ alkoxy, aryl and di-$C_1$-$C_6$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'—, wherein R' is selected from hydrogen and alkyl.

"Arylamino" refers to the group aryl-NR'—, wherein R' is selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" or "amido" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

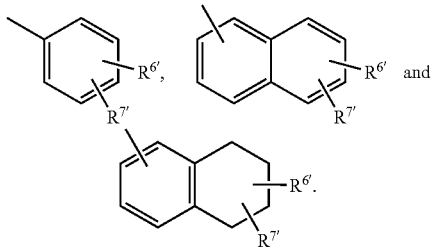

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{11}$, NR$^{10}$R$^{11}$, SO$_2$NR$^{10}$R$^{11}$, S-alkyl, S-alkyl, SOalkyl, SO$_2$alkyl, Saryl, SOaryl, SO$_2$aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

Examples of representative heteroaryls include the following:

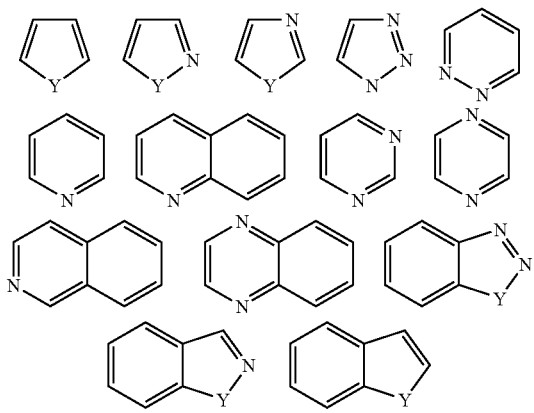

wherein each Y is selected from carbonyl, N, NR$^4$, O, and S, where R$^4$ is as defined herein.

Examples of representative cycloheteroalkyls include the following

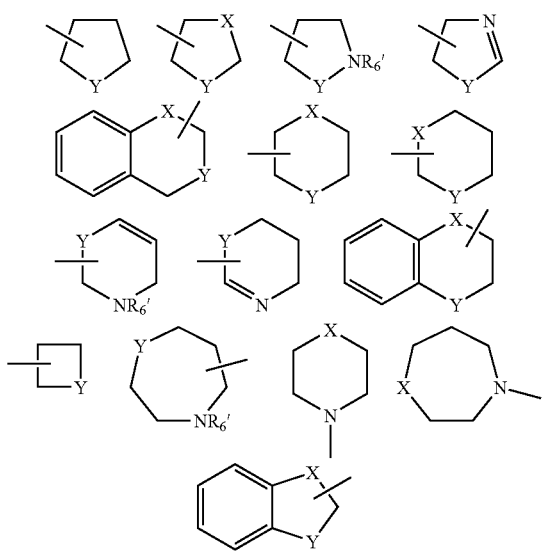

wherein each X is selected from CR$^4_2$, NR$^4$, O and S; and each Y is selected from NR$^4$, O and S, and where R$^{6'}$ is R$^2$, R$^2$ and R$^4$ being as defined herein.

Examples of representative cycloheteroalkenyls include the following:

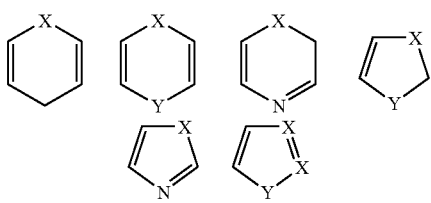

wherein each X is selected from CR$^4$, NR$^4$, O and S; and each Y is selected from carbonyl, N, NR$^4$, O and S, where R$^4$ is as defined herein.

Examples of representative aryl having hetero atoms containing substitution include the following:

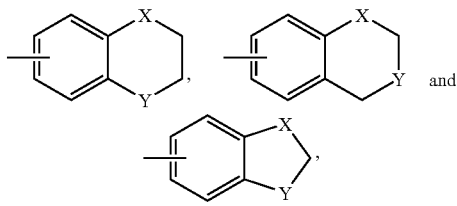

wherein each X is selected from C—R$^4$, CR$^4_2$, NR$^4$, O and S; and each Y is selected from carbonyl, NR$^4$, O and S, where R$^4$ is as defined herein.

"Hetero substituent" refers to a halo, O, S or N atom-containing functionality that may be present as an R$^4$ in a CR$^4$ group present as substituents directly on W or Z of the compounds of this invention or may be present as a substituent in the "substituted" aryl, heteroaryl and aliphatic groups present in the compounds.

Examples of hetero substituents include:
-halo,
—NO$_2$, —NH$_2$, —NHR, —N(R)$_2$,
—NRCOR, —NRSOR, —NRSO$_2$R, OH, CN, CO$_2$R,
—CO$_2$H,
—O—R,
—CON(R)$_2$, —CONROR,
—SO$_3$H, —S—R, —SO$_2$N(R)$_2$,
—S(O)R, and —S(O)$_2$R, wherein each R is independently an aryl or aliphatic, optionally with substitution. Among hetero substituents containing R groups, preference is given to those materials having aryl and alkyl R groups as defined herein. Where feasible, each R may include hydrogen. Also, where feasible, two R groups when on same atom may join to form a heterocyclic ring of 3-8 atoms. For example, two R groups of NR$^2$, SO$_2$NR$^2$, and CONR$^2$ may join, together with the N atom, to form a N-morpholino, N-pyrrolo, N-piperidino, and N-pyrazolylo ring. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

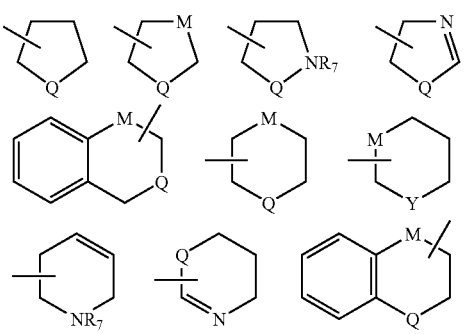

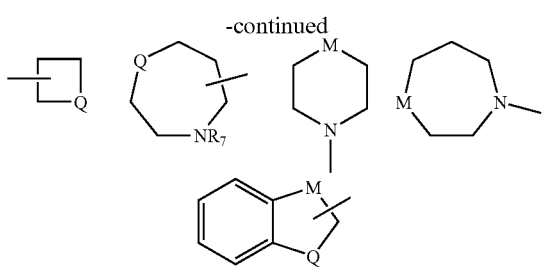

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is CR$^7$, NR$^2$, O, or S; Q is O, NR$^2$ or S, where R$^2$ is as defined herein. R$^7$ and R$^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as S(O$_2$)—R wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfoxide" refers to the divalent radical —S(O)—. "Substituted sulfoxide" refers to a radical such as S(O)—R, wherein R is any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol-keto structures and equilibrium are illustrated below:

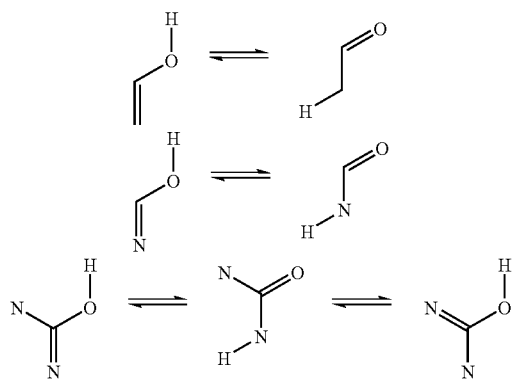

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides bicycloheteroaryl compounds useful for preventing and/or treating a broad range of conditions, associated with abnormalities in the activity of the $P2X_7$ receptor, among them, rheumatoid arthritis, Parkinson's disease, uveitis, asthma, cardiovascular conditions such as myocardial infarction, the treatment and prophylaxis of pain syndromes (acute and chronic or neuropathic), traumatic brain injury, acute spinal cord injury, neurodegenerative disorders, inflammatory bowel disease and immune dysfunctions such as autoimmune disorders or conditions, in mammals.

In a first aspect of the invention, bicycloheteroaryl compounds are disclosed that are capable of modulating the activity of the $P2X_7$ receptor in vivo, having a formula (I):

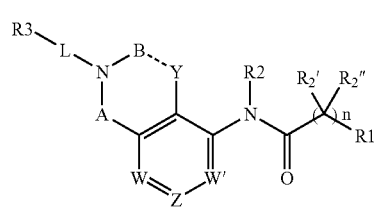

wherein

A is selected from $CR^{2'}R^{2''}$, CO, and CS;

B is selected from $CR^{2'}$, $CR^{2'}R^{2''}$, CO, and CS;

Y is independently selected from $CR^{2'}$ and $CR^{2'}R^{2''}$;

W, W' and Z are independently selected from $CR^4$ and N, provided that all three of W, W' and Z can not be N at the same time;

L is a $C_1$-$C_5$ alkylene group, heteroalkyl, 3 to 8 membered cycloalkyl or heterocycloalkyl, alkylcycloalkyl, alkylheterocycloalkyl, cycloalkylalkyl, or heterocycloalkylalkyl group, which can be optionally substituted by a substituent selected from hydroxyl, halogen and $C_1$-$C_6$ alkoxy;

n is 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;

each of $R^2$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;

$R^3$ is hydrogen or a functional group selected from acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; or $R^3$ is a 4-9 membered carbocyclic or heterocyclic ring which can be optionally substituted with at least one substituent selected from a $R^4$ group; or the group "$R^3$-L" is H;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and the dotted bond is a single or a double bond;

or a pharmaceutically acceptable salt, solvate or prodrug thereof;

and stereoisomers and tautomers thereof.

In one particular embodiment, A is CO or CS.

In a further embodiment as to compounds of formula I, n may be 0.

In a further embodiment, with respect to compounds of formula I, L may be a bond and $R^3$ is selected from H, acyl, substituted acyl, substituted or unsubstituted aminocarbonyl, alkoxycarbonyl, substituted alkoxycarbonyl, substituted or unsubstituted sulfoxide, substituted or unsubstituted sulfone, substituted or unsubstituted aminosulfonyl, substituted or unsubstituted arylsulfonyl, aryloxycarbonyl, substituted aryloxycarbonyl, heteroaryloxycarbonyl, and substituted heteroaryloxycarbonyl.

In a further embodiment, with respect to compounds of formula I, L is $L^1$; and wherein $L^1$ is a bond or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy. In one particular embodiment, when A is CO or CS, $L^1$ is a bond or $C_1$-$C_5$ alkylene group.

In a further embodiment, with respect to compound of formula I, L is $L^1$; and wherein $L^1$ is a bond or a $C_1$-$C_5$ alkylene group; and $R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl. In one particular embodiment, when $R^3$ is hydrogen, $L^1$ is a bond or a $C_1$-$C_5$ alkylene group.

In a further embodiment, with respect to compound of formula I, A is CO; and B and Y are independently selected from $CR^{2a}$ and $CR^{2a}R^{2b}$.

In a further embodiment, with respect to compound of formula I, A is CO; B and Y may all represent $CH_2$ and $R^2$ represents hydrogen.

In another aspect the present invention provides bicycloheteroaryl compounds bicycloheteroaryl compounds are disclosed that are capable of modulating the activity of the $P2X_7$ receptor in vivo, having a formula II:

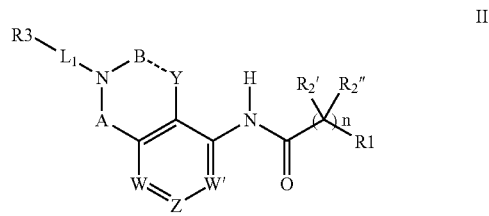

wherein

A is CO;

B and Y are independently selected from $CR^{2a}$ and $CR^{2a}R^{2b}$;

W, W' and Z are independently selected from $CR^4$ and N, provided that all three of W, W' and Z can not be N at the same time;

$L^1$ is a bond or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy;

n is 0, 1, 2 or 3;

$R^1$ is selected from a 3-13 membered cycloalkyl, heterocycloalkyl, aryl and heteroaryl ring system, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;

each of $R^{2a}$, $R^{2b}$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;

$R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl; provided when $L^1$ is a bond, $R^3$ is hydrogen, substituted or unsubstituted alkyl, substituted or unsubstituted cycloalkyl, or substituted or unsubstituted heterocycloalkyl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and the dotted bond is a single or a double bond;

or a pharmaceutically acceptable salt, solvate or prodrug thereof;

and stereoisomers and tautomers thereof.

In one particular embodiment, with respect to compounds of formula II, $L^1$ is a bond and $R^3$ is hydrogen, substituted or unsubstituted alkyl, substituted or unsubstituted cycloalkyl, or substituted or unsubstituted heterocycloalkyl In one particular embodiment, with respect to compounds of formula II, $L^1$ is a $C_1$-$C_5$ alkenyl group and $R^3$ is hydrogen.

In one particular embodiment, with respect to compounds of formula II, $L^1$ is a vinyl group and $R^3$ is hydrogen.

In one particular embodiment, with respect to compounds of formula II, when $R^3$ is hydrogen, $L^1$ is a bond or a $C_1$-$C_5$ alkylene group.

In a further embodiment, with respect to compound of formula II, A is CO; and B and Y may all represent $CR^{2a}R^{2b}$ and the dotted bond is a single bond.

In a further embodiment, with respect to compound of formula II, A is CO; and B and Y each represent $CR^{2a}$ and the dotted bond is a double bond.

In a further embodiment, with respect to compound of formula II, A is CO; B and Y may all represent $CH_2$ and the dotted bond is a single bond.

In a further embodiment, with respect to compound of formula II, A is CO; and B and Y each represent CH and the dotted bond is a double bond.

In one embodiment, with respect to compounds of formula II, W' is N.

In another embodiment, with respect to compounds of formula II, W' is $CR^4$.

In another embodiment, with respect to compounds of formula II, W' is $CR^{4'}$ and $R^{4'}$ is selected from hydrogen, halo, alkoxy, alkyl, and dialkylamino.

In another embodiment, with respect to compounds of formula II, each of $R^{2'}$ and $R^{2''}$ of the

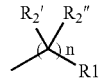

group is H.

In another embodiment, with respect to compound of formula II, wherein one of $R^{2'}$ and $R^{2''}$ of the

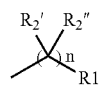

group is Me and the other is H.

In another embodiment, with respect to compounds of formula II, each of $R^{2'}$ and $R^{2''}$ of the

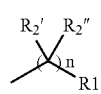

group is Me.

In another embodiment, with respect to compounds of formula II, n is 0 or 1. In one particular embodiment, n is 0. In yet another particular embodiment, n is 1.

In another embodiment, with respect to compounds of formula II, wherein the

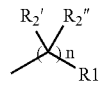

group is selected from substituted or unsubstituted admantane.

In another embodiment, with respect to compound of formula II, wherein the

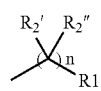

group is

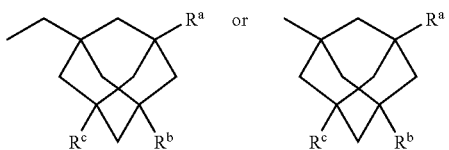

and wherein $R^a$, $R^b$ and $R^c$ are independently selected from H, halo, hydroxyl, substituted hydroxyl, alkyl, substituted alkyl, amino, substituted amino, aryl and substituted aryl.

In another embodiment, with respect to compound of formula II, wherein the

group is as described in the preceding paragraph, $R^a$, $R^b$ and $R^c$ are independently selected from H and Me. In one particular embodiment, each of $R^a$, $R^b$ and $R^c$ is H.

In another aspect the present invention provides bicycloheteroaryl compounds bicycloheteroaryl compounds are disclosed that are capable of modulating the activity of the $P2X_7$ receptor in vivo, having a formula (III or IV):

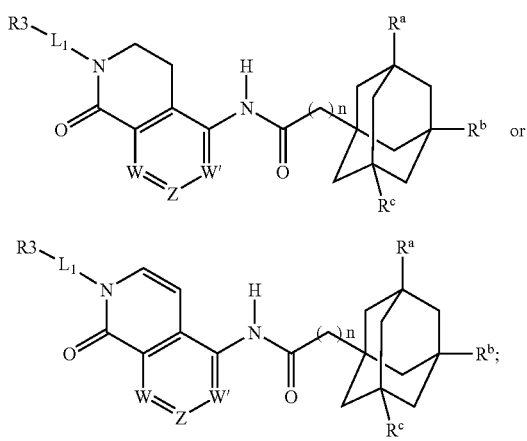

and wherein $L^1$, $R^3$, W, Z, W' and n are as described for formula II; and wherein $R^a$, $R^b$ and $R^c$ are independently selected from H, halo, hydroxyl, substituted hydroxyl, alkyl, substituted alkyl, amino, substituted amino, aryl and substituted aryl.

In one embodiment, with respect to compounds of formulae II-IV, each of W, W' and Z is independently $CR^4$.

In one embodiment, with respect to compounds of formulae II-IV, each of W, W' and Z is independently CH.

In one embodiment, with respect to compounds of formulae II-IV, W' is C-Me and W and Z both are CHs.

In one embodiment, with respect to compounds of formulae II-IV, W' is N and W and Z both are $CR^4$s.

In one embodiment, with respect to compounds of formulae II-IV, W' is N and W and Z both are CHs.

In one embodiment, with respect to compounds of formulae II-IV, Z is $CR^4$ and W and W' both are Ns.

In one embodiment, with respect to compounds of formulae II-IV, Z is CH and W and W' both are Ns.

In one embodiment, with respect to compounds of formulae II-IV, Z is N and W and W' both are $CR^4$s.

In another aspect the present invention provides bicycloheteroaryl compounds bicycloheteroaryl compounds are disclosed that are capable of modulating the activity of the $P2X_7$ receptor in vivo, having a formula (V or VI):

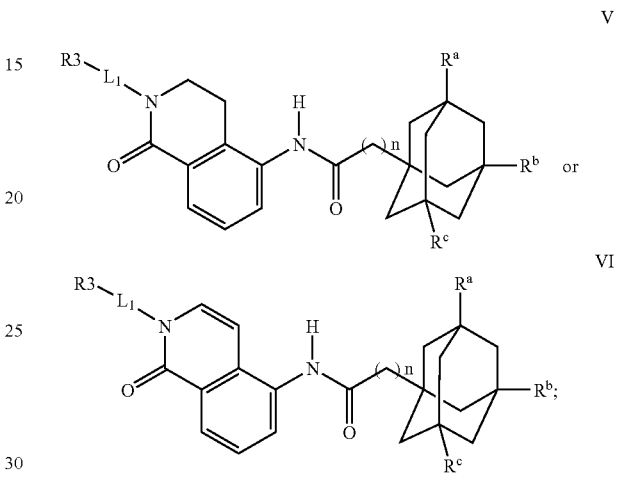

and wherein $L^1$, $R^3$, and n are as described for formula II; and wherein $R^a$, $R^b$ and $R^c$ are independently selected from H, halo, hydroxyl, substituted hydroxyl, alkyl, substituted alkyl, amino, substituted amino, aryl and substituted aryl.

In one embodiment, with respect to compounds of formulae II-VI, n is 0.

In another embodiment, with respect to compounds of formulae II-VI, n is 1.

In one embodiment, with respect to compounds of formulae II-VI, each of $R^a$, $R^b$ and $R^c$ is H.

In one embodiment, with respect to compounds of formulae II-VI, each of $R^a$, $R^b$ and $R^c$ is Me.

In one embodiment, with respect to compounds of formulae II-VI, one of $R^a$, $R^b$ and $R^c$ is halo and the rest are H.

In one embodiment, with respect to compounds of formulae II-VI, one of $R^a$, $R^b$ and $R^c$ is fluoro and the rest are H.

In one embodiment, with respect to compounds of formulae II-VI, one of $R^a$, $R^b$ and $R^c$ is OH and the rest are H.

In another embodiment, with respect to compounds of formulae II-VI, two of $R^a$, $R^b$ and $R^c$ is Me.

In one embodiment, with respect to compounds of formulae II-VI, $L^1$ is a bond and $R^3$ is H.

In another embodiment, with respect to compounds of formulae II-VI, $L^1$ is a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy; and $R^3$ is H.

In another embodiment, with respect to compounds of formulae II-VI, $L^1$ is $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_{1-6}$ alkoxy.

Further in accordance with compounds of formulae II-VI, $L^1$ may be a substituted or unsubstituted $C_1$-$C_6$ alkylene group, and particularly, may be $CH_2$, $-(CH_2)_2-$, $-(CH_2)_3-$, or $-(CH_2)_4-$.

In one embodiment, with respect to compounds of formulae II-VI, $R^3$ is substituted or unsubstituted alkyl.

In one particular embodiment, with respect to compounds of formulae II-VI, $R^3$ is substituted alkyl; and the substitution on alkyl is selected from aryl, heteroaryl, cycloalkyl, heterocycloalkyl, halo, alkoxy, hydroxy, cyano, and aryloxy. In another particular embodiment, the substitution on alkyl is selected from Ph, Cl, F, Br, CN, OH, OMe, OPh, $CF_3$, $CHF_2$, $OCF_3$, t-Bu, SMe, SOMe, $SO_2Me$, $SO_3H$, $SO_3Me$, pyridyl, cyclopropyl, cyclopentyl and cyclohexyl.

Still further in accordance with the invention, and with respect to the compounds of formalae II-VI, where present, -$L^1$-$R^3$ may be selected from H, Me, Et, benzyl, $-(CH_2)_3-OH$, $-(CH_2)_4-NHMe$, $-(CH_2)_4-OH$, $-(CH_2)_2-CH(OH)-CH_2OH$, $-(CH_2)_4-CO_2H$, $-(CH_2)_4-NHEt$, $-(CH_2)_3-NHEt$, $-(CH_2)_2-NH-(CH_2)_2OH$, $-(CH_2)_3-NH-(CH_2)_3OH$, $-(CH_2)_4-NH_2$, $-(CH_2)_3-NHCONHSO_2Me$, $-(CH_2)_3-NH-(CH_2)_2$-Me, or $-(CH_2)_2CO_2H$.

In one embodiment, with respect to compounds of formulae II-VI, $L^1$ is a $C_1$-$C_5$ alkylene group and $R^3$ is substituted or unsubstituted aryl.

In one particular embodiment, with respect to compounds of formulae II-VI, $L^1$ is a $C_1$-$C_5$ alkylene group and $R^3$ is

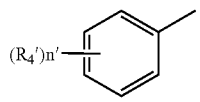

and wherein n' is selected from 1-5 and each $R^{4'}$ is independently selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

In one particular embodiment, n' is 1, 2 or 3. In another particular embodiment, n' is 1, or 2. In yet another particular embodiment, n' is 1.

In one particular embodiment, each $R^{4'}$ is independently selected from Me, Et, Ph, Cl, F, Br, CN, OH, OMe, OPh, COPh, $CF_3$, $CHF_2$, $OCF_3$, t-Bu, SMe, $CH=CH-CO_2H$, SOMe, $SO_2Me$, $SO_3H$, $SO_3Me$, and pyridyl.

In one particular embodiment, with respect to compound of formulae II-VI, $L^1$ is a $C_1$-$C_5$ alkylene group and $R^3$ is substituted or unsubstituted cycloalkyl, heterocycloalkyl, heteroaryl, bicycloaryl or bicycloheteroaryl. In another particular embodiment, the substitution is selected from Me, Et, Ph, Cl, F, Br, CN, OH, OMe, OPh, COPh, $CF_3$, $CHF_2$, $OCF_3$, t-Bu, SMe, $CH=CH-CO_2H$, SOMe, $SO_2Me$, $SO_3H$, and $SO_3Me$.

In one particular embodiment, with respect to compound of formulae II-VI, $L^1$ is a $C_1$-$C_5$ alkylene group and $R^3$ is substituted or unsubstituted naphthalene, furanyl, thiophenyl, pyrrolyl, pyrazolyl, imidazolyl, triazolyl, pyridyl, pyrimidinyl, quinoline, isoquinolinyl, tetrahydroquinolinyl, tetrahydroisoquinolinyl, indolyl, benzopyranyl, benzofuranyl, benzoxazinyl, or benzodioxanyl. In another particular embodiment, the substitution is selected from Me, Et, Ph, Cl, F, Br, CN, OH, OMe, OPh, COPh, $CF_3$, $CHF_2$, $OCF_3$, t-Bu, SMe, $CH=CH-CO_2H$, SOMe, $SO_2Me$, $SO_3H$, and $SO_3Me$.

With respect to the above embodiments the preference is for $R^4$ to be H and $R^{4'}$ to be Cl.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the $P2X_7$ receptor. Accordingly, the compounds and pharmaceutical compositions of this invention find use as therapeutics for preventing and/or treating autoimmune, inflammatory and cardiovascular conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, multiple sclerosis; diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present amine compounds for use as a pharmaceutical especially in the treatment or prevention of the aforementioned conditions and diseases. We also provide use of a present amine compound in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative bicycloheteroaryls that have been listed hereinabove. The compounds of the invention may be prepared from known or commercially available starting materials and reagents by one skilled in the art of organic synthesis.

Method A1

Intermediate 1

Preparation of
2-benzyl-5-nitroisoquinolin-1(2H)-one

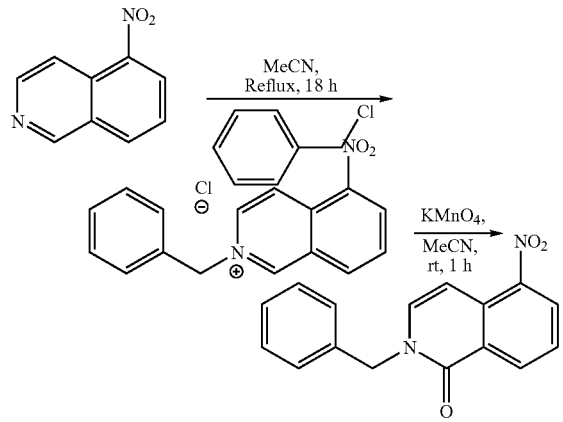

A solution of 5-nitroisoquinoline (5.0 g, 28.7 mmol) and benzyl chloride (3.45 mL, 30 mmol) in acetonitrile (100 mL) was stirred at reflux for 18 h. LCMS indicated the formation of the quaternary salt and almost complete disappearance of the starting material. The reaction mixture was cooled to room temperature, and KMnO$_4$ (13.61 g, 86.1 mmol) was added in four equal portions. The resulting suspension was stirred for 1 hour and then treated with saturated aqueous sodium meta-bisulfite (150 mL). After adding aqueous 10% HCl to pH=1, the reaction mixture was extracted with dichloromethane (4×100 mL). The combined organic layers were dried over anhydrous Na$_2$SO$_4$, filtered, and evaporated to give 8.3 g of a brown solid. A portion of the crude product was purified by flash chromatography using SiO$_2$, hexane/EtOAc (4:1) to afford 300 mg of the 2-benzyl-5-nitroisoquinolin-1 (2H)-one as a yellow solid.

$^1$H-NMR (300 MHz, CDCl$_3$) δ 8.78 (dd, J=8.1 Hz, J=1.2 Hz, 1H), 7.38 (d, J=8.1 Hz, J=1.2 Hz, 1H), 7.55 (t, J=8.1 Hz, 1H), 7.32 (m, 5H), 7.27 (s, 2H), 5.12 (s, 2H). HPLC ret. time 2.34 min, 10-100% CH$_3$CN, 3.5 min gradient; ESI-MS m/z 281.5 (M+H)$^+$. Additional information may be found in Venkov, A. P.; Statkova-Abeghe, S. M. *Tetrahedron* 1996, 52, 4, 1451, incorporated herein by reference.

Intermediate 2

Preparation of
5-amino-2-benzylisoquinolin-1(2H)-one

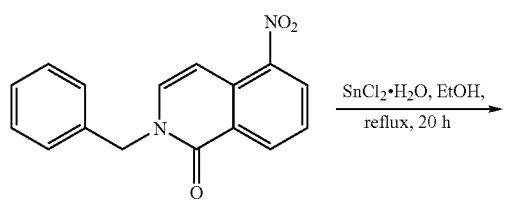

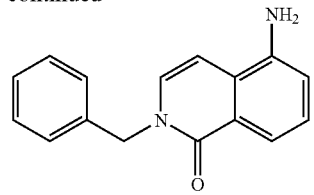

Tin(II) chloride dihydrate (1.21 g, 5.36 mmol) was added to a stirred solution of 2-benzyl-5-nitroisoquinolin-1(2H)-one (300 mg, 1.07 mmol) in anhydrous ethanol (20 mL). The reaction mixture was stirred at reflux for 20 h. The resulting mixture was cooled to room temperature, treated with saturated aqueous sodium bicarbonate to pH=11 and diluted with water (100 mL). The obtained mixture was extracted with ethyl acetate (3×70 mL). The combined organic fractions were dried over anhydrous Na$_2$SO$_4$, filtered and evaporated to give 5-amino-2-benzylisoquinolin-1(2H)-one (248 mg, 1.0 mmol, 93% yield) as an orange foam.

$^1$H-NMR (300 MHz, CDCl$_3$) δ 8.78 (dd, J=8.1 Hz, J=1.2 Hz, 1H), 7.38 (d, J=8.1 Hz, J=1.2 Hz, 1H), 7.55 (t, J=8.1 Hz, 1H), 7.32 (m, 5H), 7.27 (s, 2H), 5.12 (s, 2H). HPLC ret. time 2.34 min, 10-100% CH$_3$CN, 3.5 min gradient; ESI-MS m/z 281.5 (M+H)$^+$. Additional information may be found in Matassa, V. G.; et al. *J. Med. Chem.* 1990, 33, 9, 2621, incorporated herein by reference.

Preparation of 2-adamantan-1-yl-N-(2-benzyl-1-oxo-1,2-dihydro-isoquinolin-5-yl)-acetamide (Compound 701)

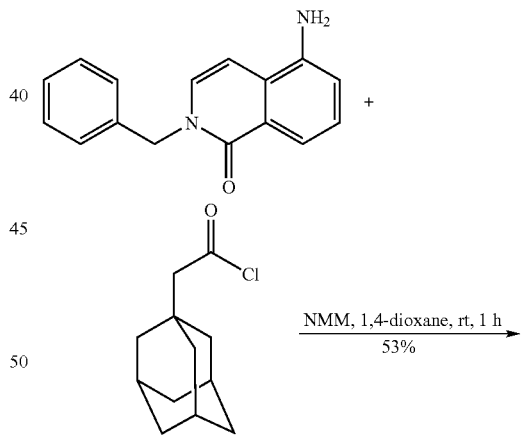

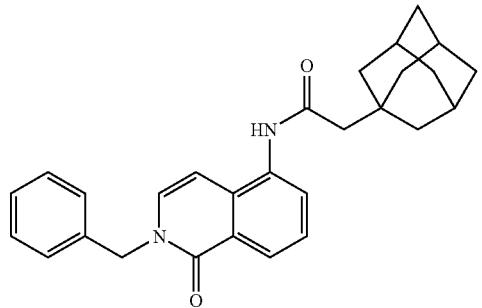

To a solution of 5-amino-2-benzylisoquinolin-1(2H)-one (50 mg, 0.2 mmol) and NMM (0.022 mL, 0.2 mmol) in 1,4-dioxane (3 mL) was added dropwise at room temperature a solution of 1-adamantaneacetic acid chloride (43 mg, 0.2 mmol) in 1,4-dioxane (5 mL). The reaction mixture was stirred at room temperature for 1 h. The volatiles were removed on a rotary evaporator. The crude product was purified by prep. HPLC affording 2-Adamantan-1-yl-N-(2-benzyl-1-oxo-1,2-dihydro-isoquinolin-5-yl)-acetamide (45.5 mg, 0.11 mmol, 53% yield) as a white solid.

$^1$H-NMR (300 MHz, CDCl$_3$) δ 8.29 (d, J=7.8 Hz, 1H), 7.92 (d, J=7.8 Hz, 1H), 7.43 (t, J=7.8 Hz, 1H), 7.27 (m, 5H), 7.05 (d, J=7.5 Hz, 1H), 6.41 (d, J=7.5 Hz, 1H), 5.17 (s, 2H), 2.17 (s, 2H), 1.99 (br s, 3H), 1.75-1.60 (m, 12H). HPLC ret. time 2.78 min, 10-100% CH$_3$CN, 3.5 min gradient; ESI-MS m/z 427.3 (M+H)$^+$.

Method A2

Preparation of 2-Adamantan-1-yl-N-(2-benzyl-1-oxo-1,2,3,4-tetrahydro-isoquinolin-5-yl)-acetamide (Compound 702)

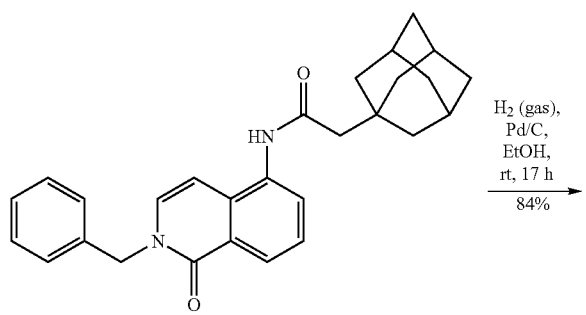

A 50 mL round-bottom flask was charged with a solution of 2-Adamantan-1-yl-N-(2-benzyl-1-oxo-1,2-dihydro-isoquinolin-5-yl)-acetamide (14 mg, 0.033 mmol) in absolute ethanol (6 mL) and 10% Pd/C (10 mg). The reaction vessel was evacuated and filled with hydrogen via balloon. The reaction suspension was stirred at room temperature under hydrogen (1 atm) for 17 h. The resulting mixture was filtered and the filtrate was concentrated on a rotary evaporator. The crude product was purified by prep. TLC using DCM/EtOAc (3:1) as the elutant affording the title compound (11.8 mg, 0.027 mmol, 84% yield) as a white solid.

$^1$H-NMR (300 MHz, CDCl$_3$) δ 8.02 (d, J=7.2 Hz, 1H), 7.62 (d, J=7.2 Hz, 1H), 7.33 (t, J=7.2 Hz, 1H), 7.28 (m, 5H), 6.92 (br s, 1H), 4.77 (s, 2H), 3.45 (t, J=6.3 Hz, 2H), 2.80 (t, J=6.3 Hz, 2H), 2.10 (s, 2H), 1.94 (br s, 3H), 1.75-1.54 (m, 12H). HPLC ret. time 2.74 min, 10-100% CH$_3$CN, 3.5 min gradient; ESI-MS m/z 429.3 (M+H)$^+$. Additional information can be found in Paulvannan, K.; Stille, J. R. *J. Org. Chem.* 1994, 59, 7, 1613, incorporated herein by reference. The various 2-benzyl-1-oxo-1,2,3,4-tetrahydro-isoquinolin-5-yl compounds included in Table 1 may be prepared in an analogous manner.

Method B

Intermediate 3

Preparation of (E)-methyl 2-(2-(dimethylamino)-vinyl)-3-nitrobenzoate

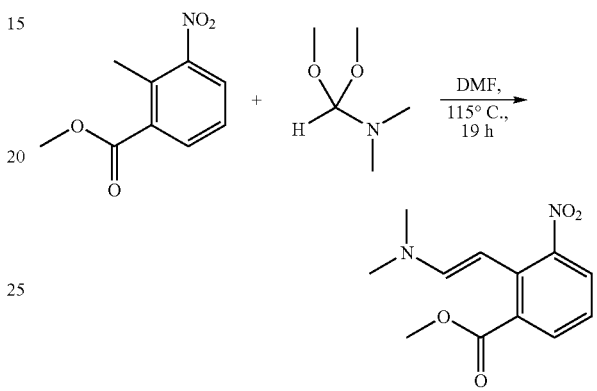

A mixture of methyl 2-methyl-3-nitrobenzoate (5.0 g, 25.6 mmol) and N,N-dimethylformamide dimethyl acetal (9.18 g, 77 mmol) in DMF (30 mL) was stirred at 115° C. for 17 h. The volatiles were removed under reduced pressure to give (E)-methyl 2-(2-(dimethylamino)-vinyl)-3-nitrobenzoate as brown oil.

$^1$H-NMR (300 MHz, CDCl$_3$) δ 7.68 (m, 2H), 7.07 (t 1H), 6.32 (d, 1H), 5.65 (d, 1H), 73.85 (s, 3H), 2.82 (s, 6H).

Intermediate 4

Preparation of 5-Nitro-1H-isochromen-1-one

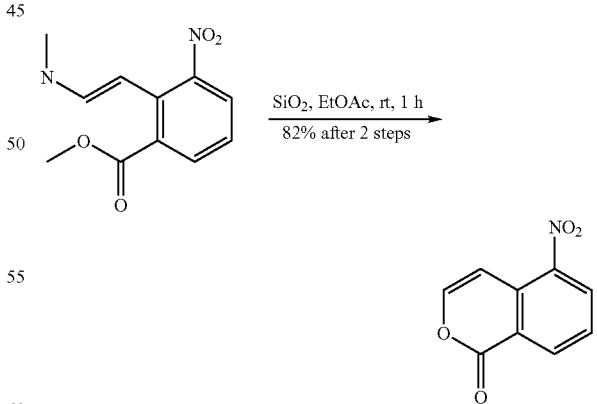

(E)-Methyl 2-(2-(dimethylamino)vinyl)-3-nitrobenzoate was re-dissolved in EtOAc (200 mL), and silica gel (200 g) was added. The resulting suspension was stirred at room temperature for 1 h. The EtOAc solution was filtered off. Silica gel was washed with EtOAc (2×150 mL) and the combined organics were evaporated and dried under reduced pressure to yield 5-nitro-1H-isochromen-1-one (4.0 g, 21.0 mmol, 82% after two steps) as a brown solid.

$^1$H-NMR (300 MHz, CDCl$_3$) δ 8.62 (d, 1H), 8.47 (d, 1H), 7.65 (m, 1H), 7.42 (d, 1H), 7.36 (d, 1H). HPLC ret. time 1.72 min, 10-100% CH$_3$CN, 3.5 min gradient; ESI-MS m/z 192.1 (M+H)$^+$. Additional information can be found in McDonald, M. C. et al. British J. Pharmacol. 2000, 130, 843, incorporated herein by reference.

Intermediate 5

Preparation of 5-Amino-1H-isochromen-1-one

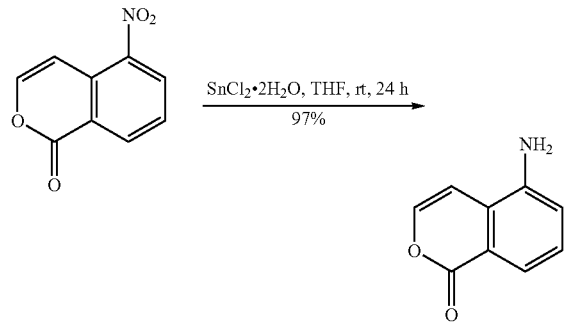

Tin(II) chloride dihydrate (41.9 g, 185.7 mmol) was added to a stirred solution of 5-nitro-1H-isochromen-1-one (7.1 g, 37.1 mmol) in anhydrous THF (120 mL). The reaction mixture was stirred at room temperature for 18 h. The resulting mixture was diluted with EtOAc (400 mL) and treated with saturated aqueous sodium bicarbonate to pH=10. Water (100 mL) was added and the layers were separated. The aqueous phase was extracted with ethyl acetate (2×150 mL) and the combined organic fractions were dried over Na$_2$SO$_4$, filtered and evaporated to yield 5-amino-1H-isochromen-1-one (5.8 g, 36.0 mmol, 97%) as a yellow solid.

$^1$H-NMR (300 MHz, CD$_3$OD) δ 7.52 (d, 1H), 7.32 (d, 1H), 7.27 (t, 1H), 7.07 (d, 1H), 6.80 (d, 1H). HPLC ret. time 1.16 min, 10-100% CH$_3$CN, 3.5 min gradient; ESI-MS m/z 162.3 (M+H)$^+$. Additional information can be found in Lee, B. S.; et al. J. Org. Chem. 2004, 69, 3319, incorporated herein by reference.

Intermediate 6

Preparation of 2-Adamantan-1-yl-N-(1-oxo-1H-isochromen-5-yl)-acetamide

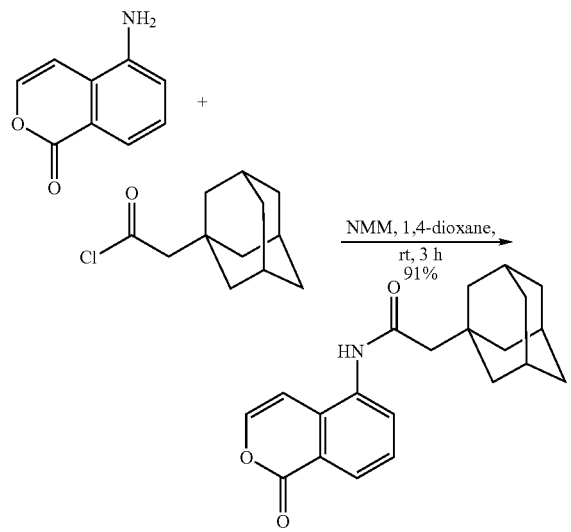

To a solution of 5-amino-1H-isochromen-1-one (2.95 g, 18.3 mmol) and NMM (2.02 mL, 18.3 mmol) in 1,4 dioxane (55 mL) was added dropwise at room temperature a solution of 1-adamantaneacetic acid chloride (3.9 g, 18.3 mmol) in 1,4-dioxane (40 mL). The reaction mixture was stirred at room temperature for 3 h and then partitioned between DCM (400 mL) and water (200 mL). The layers were separated. The aqueous phase was washed with DCM (100 mL). The combined organic layers were dried over sodium sulfate, filtered and evaporated. The crude product was suspended in hexane (100 mL) and filtered off. The solid was collected on the filter and dried in vacuo to yield 2-adamantan-1-yl-N-(1-oxo-1H-isochromen-5-yl)-acetamide as a yellow solid (5.6 g, 16.7 mmol, 91%).

$^1$H-NMR (300 MHz, CDCl$_3$) δ 8.13 (d, 1H), 7.99 (d, 1H), 7.49 (t, 1H), 7.26 (m, 1H), 7.21 (br s, 1H), 6.46 (d, 1H), 2.19 (s, 2H), 2.01 (br s, 3H), 1.75-1.63 (m, 12H). HPLC ret. time 2.47 min, 10-100% CH$_3$CN, 3.5 min gradient; ESI-MS m/z 338.4 (M+H)$^+$.

Preparation of 2-Adamantan-1-yl-N-[2-(4-fluoro-benzyl)-1-oxo-1,2-dihydro-isoquinolin-5-yl]-acetamide (Compound 703)

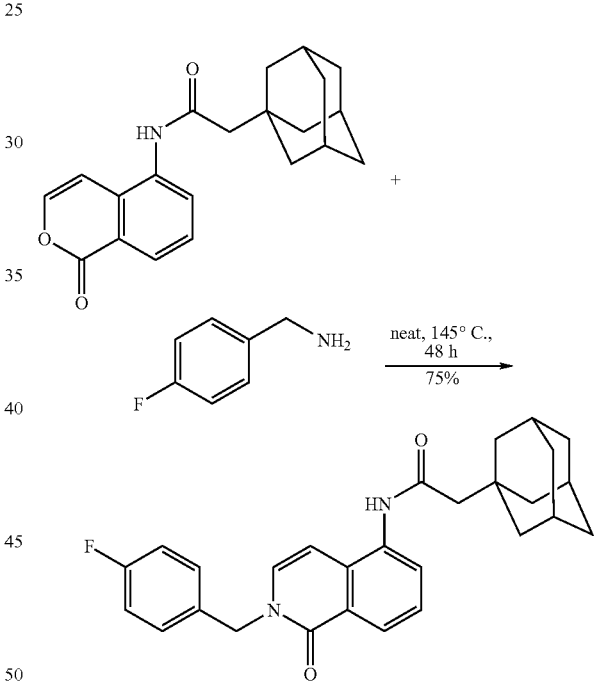

A mixture of 2-adamantan-1-yl-N-(1-oxo-1H-isochromen-5-yl)-acetamide (0.3 g, 0.89 mmol) and 4-fluorobenzylamine 0.668 g (5.33 mmol) in an 8 mL sealed vial was heated at 145° C. for 48 h. The reaction vessel was cooled to room temperature. The crude product was purified by prep. HPLC to yield 2-adamantan-1-yl-N-[2-(4-fluoro-benzyl)-1-oxo-1,2-dihydro-isoquinolin-5-yl]-acetamide (0.298 g, 0.67 mmol, 75%) as a pale yellow powder.

$^1$H-NMR (300 MHz, CDCl$_3$) δ 8.30 (d, 1H), 7.94 (d, 1H), 7.46 (t, 1H), 7.28 (m, 2H), 7.15 (br s, 1H), 7.08 (d, 1H), 6.99 (m, 2H), 6.43 (d, 1H), 5.15 (s, 2H), 2.18 (s, 2H), 2.00 (br s, 3H), 1.76-1.60 (m, 12H). HPLC ret. time 2.71 min, 10-100% CH$_3$CN, 3.5 min gradient; ESI-MS m/z 445.5 (M+H)$^+$.

The various N-benzyl substituted 1-oxo-1,2-dihydro-isoquinolin-5-yl derivatives included in Table 1 are or can be prepared in a manner analogous to that described in Method B, unless otherwise described.

Method B1

Alternate Representative Method for Preparation of N-substituted-1-oxo-1,2-dihydro-isoquinolin-5-yl Derivatives

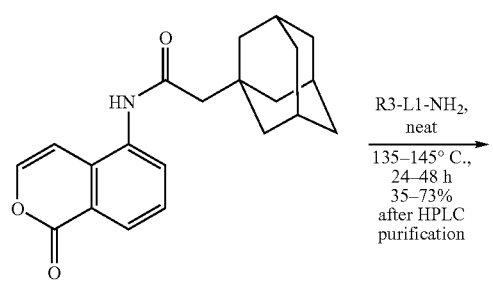

R3-L1-NH₂, neat
135–145° C.,
24–48 h
35–73%
after HPLC purification

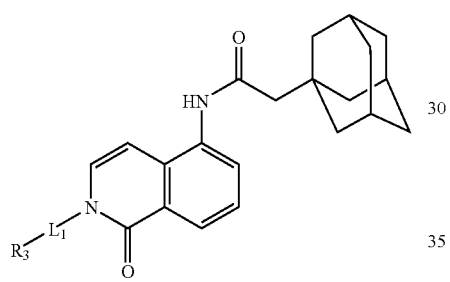

The reactions were performed using 0.089 mmoles of the pyrone and a 6-fold excess of the amine. All reactions were monitored by 1 cms for completion and upon completion were purified by preparative HPLC using 0.1% formic acid buffer. The N-L¹-R³ substituted compounds of this invention, wherein L¹-R³ is as described for formula II, are or can be prepared in a manner analogous to that described in Method B1, or some modification thereof, unless otherwise described.

Method C

Another Representative Method for Preparation of N-substituted-1-oxo-1,2-dihydro-isoquinolin-5-yl Derivatives

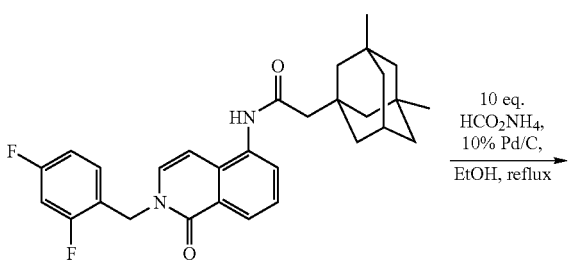

10 eq. HCO₂NH₄, 10% Pd/C, EtOH, reflux

-continued

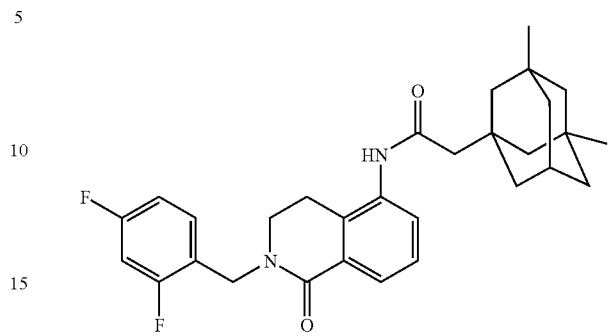

In a vial containing reactant (25 mg, 0.05 mmol) in EtOH (1 ml), ammonium formate (64 mg, 1 mmol) under nitrogen was placed the same amount by weight of 10% Pd/C. Reaction was heated to 80° C. for 16 h in a sealed vial. After filtering off the Pd/C and removal of the solvent, the crude product was purified by prep. TLC with 5% of MeOH in DCM to obtain the desired product (3.9 mg, 0.008 mmol, 16%).

Method D

Intermediate 7

Preparation of 5-Aminoisochroman-1-one

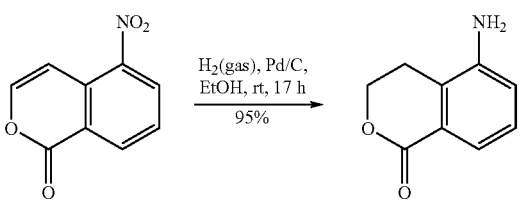

H₂(gas), Pd/C, EtOH, rt, 17 h
95%

A 250 mL round-bottom flask was charged with a solution of 5-nitro-1H-isochromen-1-one (3.0 g, 15.7 mmol) in absolute ethanol (60 mL) and 10% Pd/C (600 mg). The reaction vessel was evacuated and filled with hydrogen via balloon. The reaction suspension was stirred at room temperature in hydrogen atmosphere (via balloon) for 17 h. The resulting mixture was filtered and the solvent was removed on a rotary evaporator. After drying under reduced pressure, 2.40 g, (14.9 mmol, 95%) of 5-aminoisochroman-1-one were isolated as a white solid.

¹H-NMR (300 MHz, CD₃OD) 'δ' 7.36 (d, J=7.5 Hz, 1H), 7.13 (t, J=7.5 Hz, 1H), 7.97 (d, J=7.8 Hz, 1H), 4.48 (t, J=6.3 Hz, 2H), 2.83 (t, J=6.3 Hz, 2H). HPLC ret. time 0.87 min, 10-100% CH₃CN, 3.5 min gradient; ESI-MS m/z 164.3 (M+H)⁺.

Intermediate 8

Preparation of 2-Adamantan-1-yl-N-(1-oxo-isochroman-5-yl)-acetamide

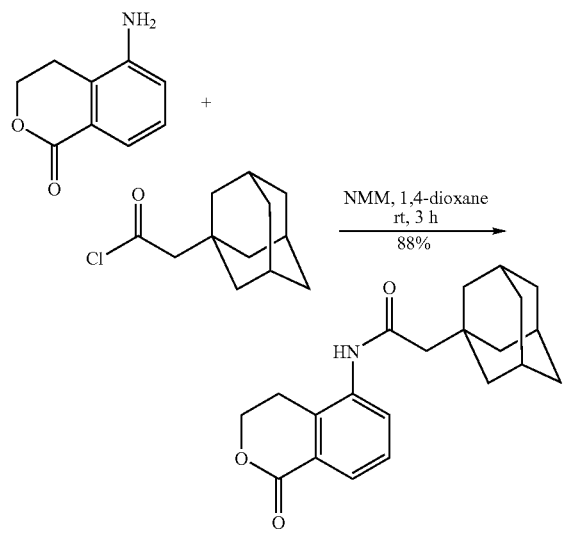

2-Adamantan-1-yl-N-(1-oxo-isochroman-5-yl)-acetamide was obtained in an analogous manner to 2-adamantan-1-yl-N-(1-oxo-1H-isochromen-5-yl)-acetamide from 5-aminoisochroman-1-one (2.0 g, 12.3 mmol), 1-adamantaneacetic acid chloride (2.61 g, 12.3 mmol) and NMM (1.35 mL, 12.3 mmol) in 1,4-dioxane (73 mL). Thus this procedure yielded, 3.66 g (10.8 mmol, 88%) of 2-Adamantan-1-yl-N-(1-oxo-isochroman-5-yl)-acetamide.

$^1$H-NMR (300 MHz, CDCl$_3$) 'δ' 7.97 (d, J=7.2 Hz, 1H), 7.76 (d, J=7.8 Hz, 1H), 7.38 (t, J=7.8 Hz, 1H), 7.11 (br s, 1H), 4.50 (t, J=6.0 Hz, 2H), 2.94 (t, J=6.0 Hz, 2H), 2.15 (s, 2H), 2.01 (br s, 3H), 1.76-1.69 (m, 12H). HPLC ret. time 0.87 min, 10-100% CH$_3$CN, 2.31 min gradient; ESI-MS m/z 340.3 (M+H)$^+$.

Preparation of 2-Adamantan-1-yl-N-[2-(2,4-difluoro-benzyl)-1-oxo-1,2,3,4-tetrahydro-isoquinolin-5-yl]-acetamide (Compound 725)

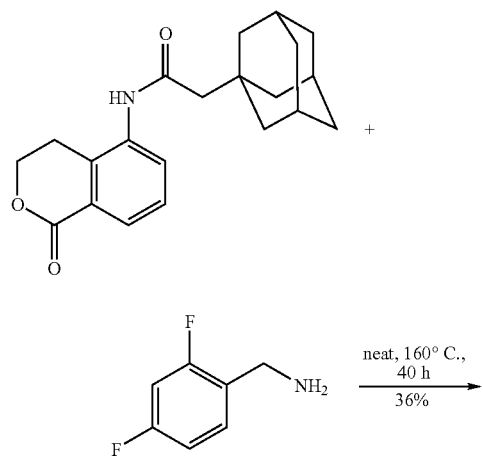

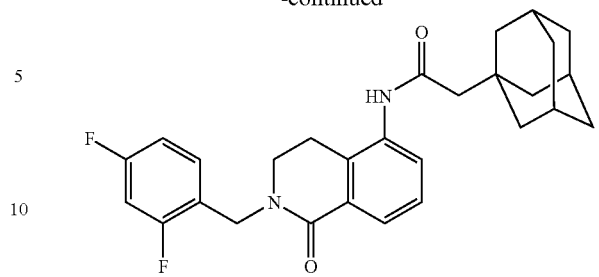

A mixture of 2-adamantan-1-yl-N-(1-oxo-isochroman-5-yl)-acetamide (39 mg, 0.115 mmol) and 2,4-difluorobenzylamine (99 mg, 0.689 mmol) was heated at 160° C. for 40 h. The reaction vessel was cooled to room temperature and the solvents removed under reduced pressure. The crude product was purified by prep. HPLC to afford 2-adamantan-1-yl-N-[2-(2,4-difluoro-benzyl)-1-oxo-1,2,3,4-tetrahydro-isoquinolin-5-yl]-acetamide (19.2 mg, 0.042 mmol, 36%) as a white solid.

$^1$H-NMR (300 MHz, CDCl$_3$) δ 7.98 (d, J=7.5 Hz, 1H), 7.60 (d, J=7.8 Hz, 1H), 7.47-7.29 (m, 2H), 6.94 (br s, 1H), 6.81 (m, 2H), 4.75 (s, 2H), 3.53 (t, J=6.6 Hz, 2H), 2.84 (t, J=6.6 Hz, 2H), 2.11 (s, 2H), 1.99 (br s, 3H), 1.75-1.63 (m, 12H). HPLC ret. time 2.71 min, 10-100% CH$_3$CN, 2.62 min gradient; ESI-MS m/z 465.2 (M+H)$^+$.

Method E

Preparation of 2-adamantyl-N-(1-oxo-1,2-dihydroisoquinolin-5-yl)acetamide (Compound 804)

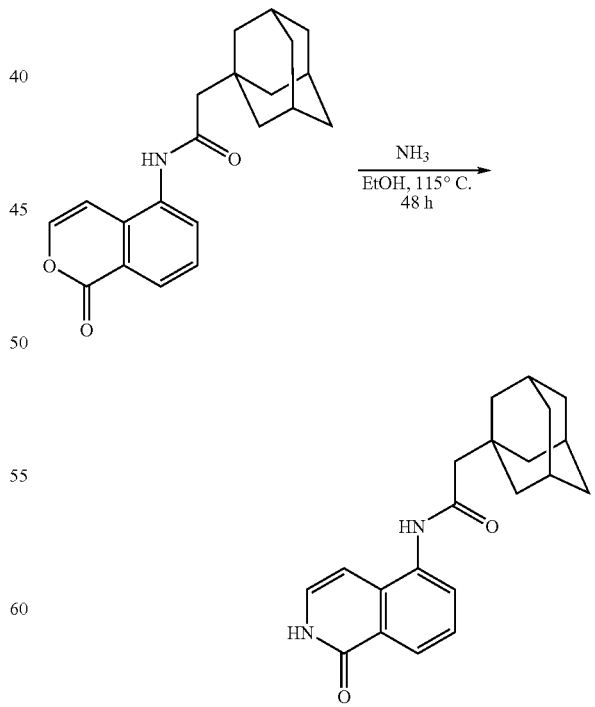

90 mg (0.27 mmol) of 2-adamantyl-N-(1-oxo-1H-isochromen-5-yl)acetamide (1) was treated with 10 mL (20 mmol)

of a 2 M ammonia solution in ethanol at room temperature in a resealable tube. The reaction vessel was sealed and heated at 115° C. for 48 h. After the reaction mixture was cooled down to room temperature, the solvent was evaporated and residue obtained was purified by prep. HPLC to yield 2-adamantyl-N-(1-oxo-1,2-dihydroisoquinolin-5-yl)acetamide (2a) (41 mg, 0.122 mmol, 45%) as an off-white powder. HPLC ret. time 2.07 min, 10-100% CH$_3$CN, 3.5 min gradient; ESI-MS m/z 337.2 (M+H)$^+$.

Method F

Preparation of adamantyl-N-(2-methyl-1-oxo-1,2-dihydroisoquinolin-5-yl)acetamide (Compound 805)

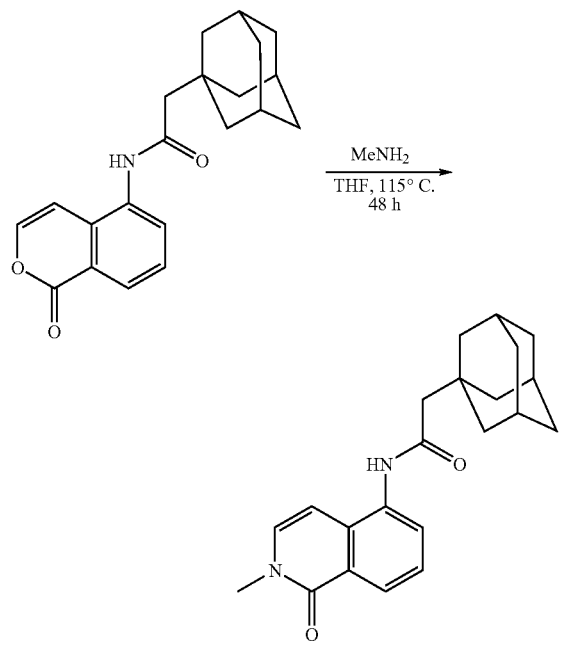

This analog was prepared using 90 mg (0.27 mmol) of 2-adamantyl-N-(1-oxo-1H-isochromen-5-yl)acetamide (1) and 10 mL (20 mmol) of 2 M methylamine solution in tetrahydrofuran. Adamantyl-N-(2-methyl-1-oxo-1,2-dihydroisoquinolin-5-yl)acetamide (12 mg, 0.034 mmol, 13%) was obtained after prep. HPLC purification. HPLC ret. time 2.23 min, 10-100% CH$_3$CN, 3.5 min gradient; ESI-MS m/z 351.3 (M+H)$^+$.

Intermediate 9

Preparation of (3,5-Dimethyl-adamantan-1-yl)-acetyl chloride

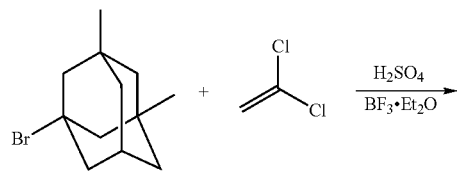

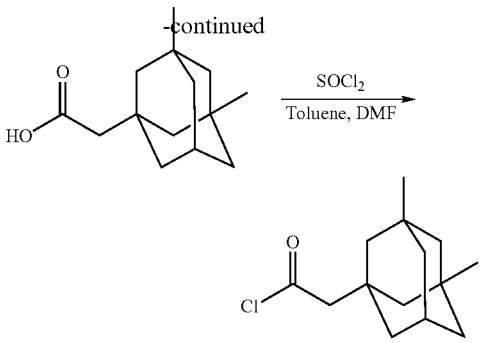

Preparation of (3,5-Dimethyl-adamantan-1-yl)-acetic acid

The bromide (24.32 g, 100 mmol) in dichloroethane was added into 90% H$_2$SO$_4$ solution at 10° C. (cold water bath). The reaction mixture was stirred at 10° C. for 1 hr. Then BF$_3$ etherate (2.84 g, mmol) was added dropwise in 30 minutes via a syringe. The reaction mixture was stirred at 10-15° C. for 2 more hours with additional BF$_3$ etherate was added until complete consumption of the starting bromide before pouring onto ice. The water was adjusted to pH=9 followed by extraction with ether. The aqueous layer was acidified with HCl to pH=3 followed by extraction with ether, dried, organic solvent removed to give solid product, which was taken on directly to the next step.

$^1$H NMR (CD$_3$Cl$_3$) δ 0.82(s, 6H), 1.02-1.38 (m, 12H), 1.74 (s, 1H), 2.13 (s, 2H).

Preparation of (3,5-Dimethyl-adamantan-1-yl)-acetyl chloride

Into a flask containing acid in toluene (50 ml) was added SOCl$_2$ and 1 drop of DMF. Reaction was then heated to 60° C. for 1 hour. After removal of solvent and co-evaporate with toluene (2 ml), the crude product was used without further purification.

Method G

Intermediate 10

Preparation of 5-aminodimethyl-1-adamantaneacetyl-1H-isochromen-1-one

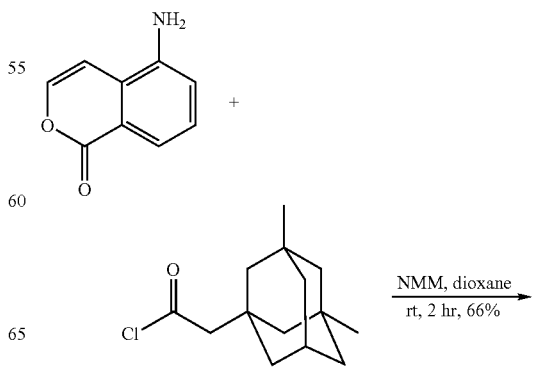

-continued

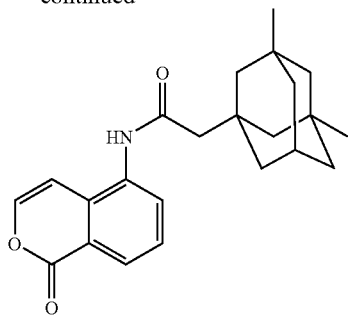

To a flask containing 5-amino-1H-isochromen-1-one (1.4 g, 8.7 mmol), cat DMAP and NMM (2.64 g, 26 mmol) in dioxane (50 ml) at 0° C. was added dimethyl-1-adamantaneacetic acid chloride (2.1 g, 8.7 mmol) in dioxane (5 ml). The reaction mixture was stirred at room temperature for 2 days. The volatiles were removed under reduced pressure. The crude product was partitioned between water and ethyl acetate. The organic was separated washed with brine, dried over anhydrous $Na_2SO_4$, filtered and concentrated. The crude product was recrystallized from ethyl ether to give the desired product (2.1 g, 5.74 mmol, 66%) as an off white solid. ESI-MS m/z 366.2 $(M+H)^+$.

Another Representative Method for Preparation of N-substituted-1-oxo-1,2-dihydro-isoquinolin-5-yl Derivatives

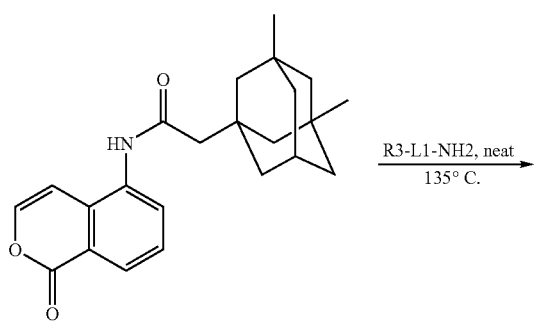

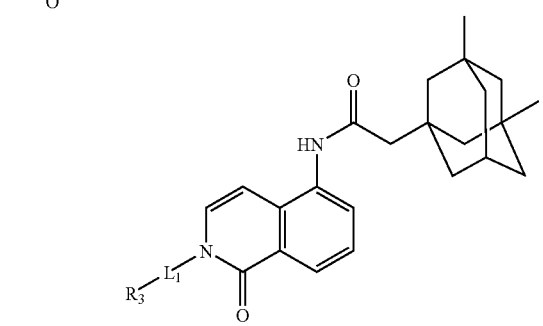

The various N-substituted-1-oxo-1,2-dihydro-isoquinolin-5-yl compounds, wherein the $L^1$-$R^3$ group is as described for formula II, included in Table 1 are or can be prepared according to method G. Thus, a 1-dram vial containing 5-aminodimethyl-1-adamantaneacetyl-1H-isochromen-1-one (50 mg, 0.14 mmol) and the appropriate amine (0.41 mmol) was heated neat at 135° C. for 1-2 days. The crude was purified by either preparative HPLC or preparative TLC to give products in yields that ranged from 8-80%.

Method H

Another Representative Method for Preparation of N-substituted-1-oxo-1,2,3,4-tetrahydro-isoquinolin-5-yl Derivatives Preparation of Compound 815

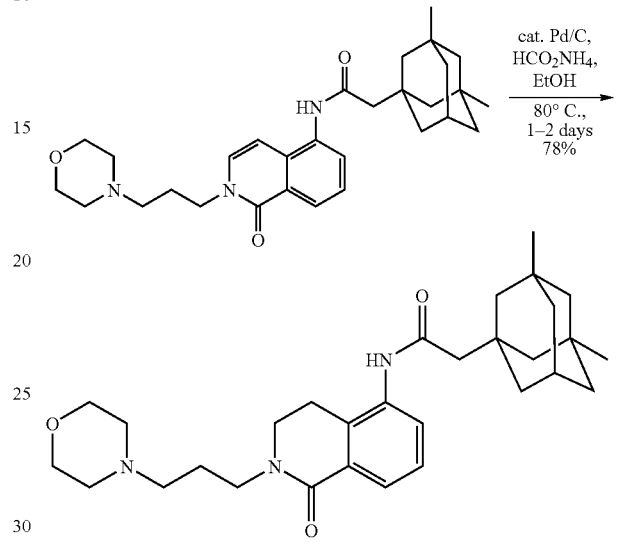

A mixture of Compound 892 (5 mg, 0.1 mmol), ammonium formate (6 mg, 1.0 mmol), absolute ethanol (3 mL) and 10% Pd/C (3 mg) in a vial was heated to 80° C. for 2 days. The resulting mixture was filtered and the filtrate was concentrated on a rotary evaporator. The crude product was purified by prep. TLC using MeOH in DCM (5%) as the elutant affording the Compound 5 (3.9 mg, 7.9 mmol, 78%) as a white solid.

1H-NMR (300 MHz, CDCl3) δ 7.91 (d, J=6.9 Hz, 1H), 7.60 (d, J=7.5 Hz, 1H), 7.32 (t, J=7.8 Hz, 1H), 6.88 (s, 1H), 3.70 (t, J=4.8 Hz, 4H), 3.57 (m, 4H), 2.87(d, J=6.0 Hz, 2H), 2.44 (m, 6H), 1.84 (t, J=5.4 Hz, 2H), 1.25(m, 11H), 0.90 (m, 4H), 0.83 (s, 6H). HPLC ret. time 2.59 min, 10-100% CH3CN, 3.5 min gradient; ESI-MS m/z 493.2 (M+H)+.

Method I

Preparation of 3-Fluoro-Adamantan-1-yl-N-(2-benzyl-1-oxo-1,2-dihydro-isoquinolin-5-yl)-formamide (Compound 816)

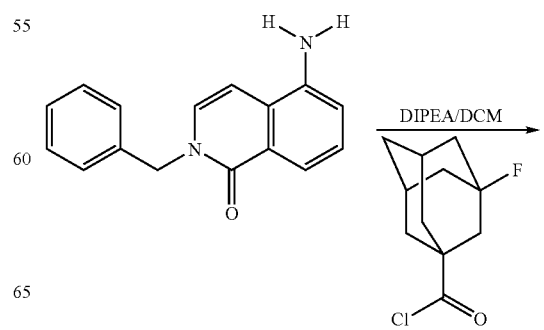

-continued

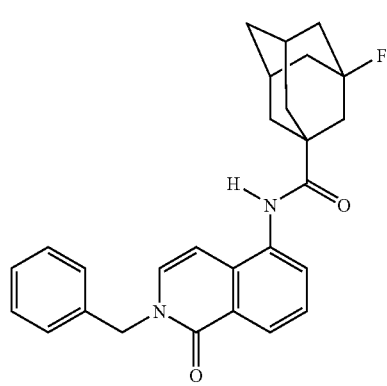

To a solution of (50 mg, 0.2 mmol) and DIPEA (0.15 mL) in DCM (2 mL) was added a solution of 3-fluoro-1-adamantanecarboxylic acid chloride (65 uL, ~65 mg, 0.30 mmol) at room temperature. The reaction mixture was stirred at room temperature for 17 h. The volatiles were removed on a rotary evaporator. The crude product was purified by prep. HPLC to yield the title compound (41 mg, 0.095 mmol, 48%) as a white solid.

1H-NMR (300 MHz, CDCl3) δ 8.32 (d, 1H), 7.87 (d, 1H), 7.46 (t, 1H), 7.27 (m, 5H), 7.09 (d, 1H), 6.30 (d1H), 5.20 (s, 2H), 2.44 (s, 2H), 2.15 (d, 2H), 1.95 (br s, 8H), 1.67 (br s, 2H). ESI-MS m/z 431.1 (M+H)+.

Additional Representative Methods for Preparing N-substituted-1-oxo-1,2-dihydro-isoquinolin-5-yl Derivatives Method K Representative Example Preparation of (Compound 870)

-continued

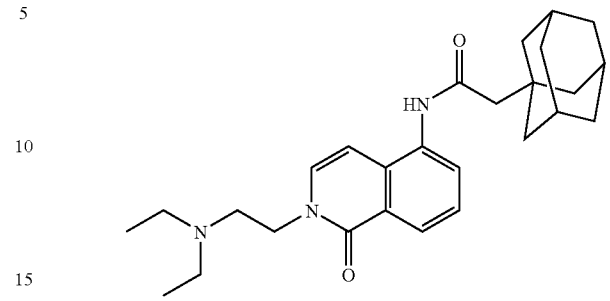

Intermediate 6 (0.27 mmol) was suspended in appropriate amine (20 mmol) and the reaction mixture was heated by microwave at 200° C. for 10–20 hours. EtOAc was added and the solution was washed by water, brine, and dried over Na₂SO₄. Volatiles were removed under reduced pressure and the residue was subjected to silica gel purification to yield the product.

Method L

Representative Example

Preparation of (Compound 826)

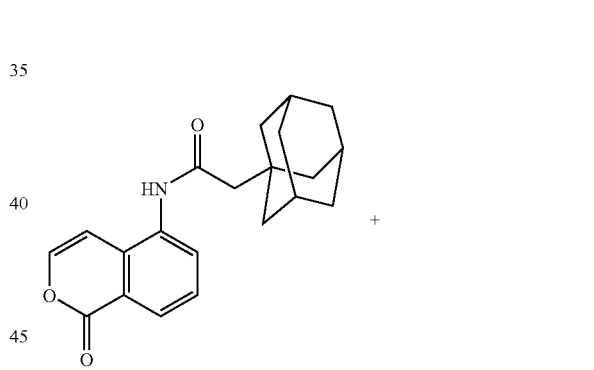

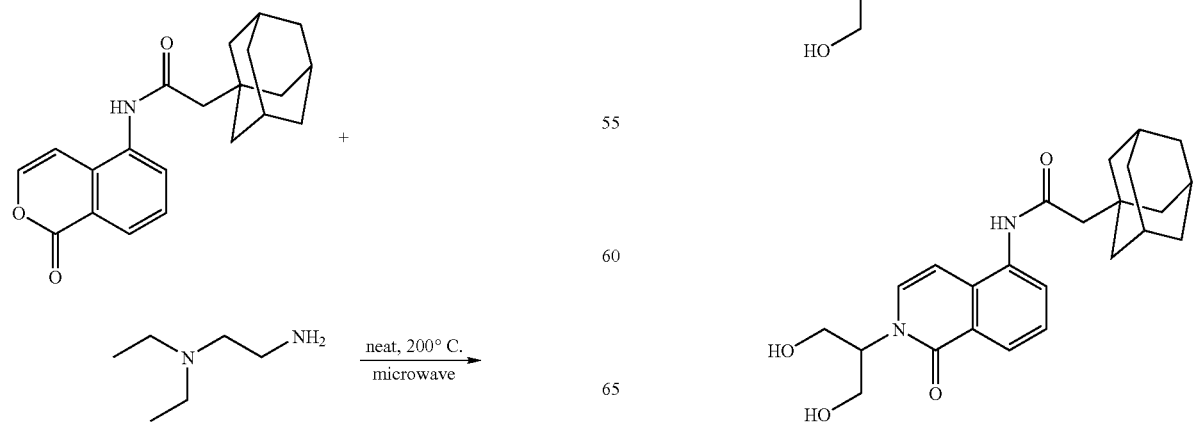

Intermediate 6 (0.27 mmol) was suspended in appropriate amine (33 mmol) and stirred at 140° C. in a sealed tube for 48 h. The volatile portion was removed and the residue was subjected to silica gel purification to yield the product as a solid.

Method M

Representative Example

Preparation of (Compound 827)

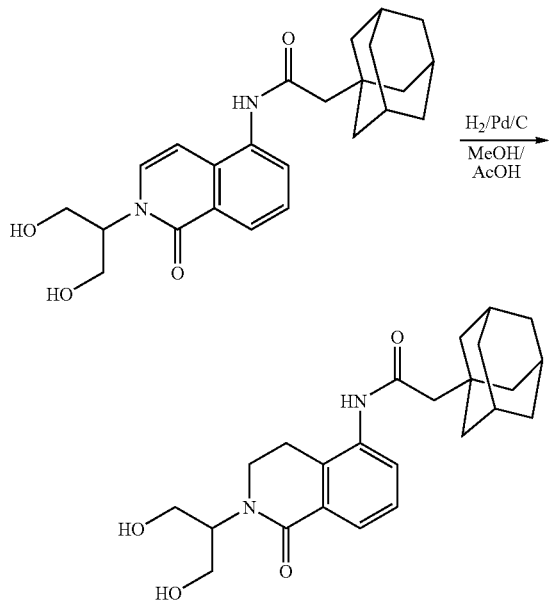

2-Adamantan-1-yl-N-[2-(2-hydroxy-1-hydroxymethyl-ethyl)-1-oxo-1,2-dihydro-isoquinolin-5-yl]-acetamide (215 mg, 0.508 mmol) was dissolved in MeOH (10 mL), AcOH (1 mL) and Pd/C (10%) were added and the reaction mixture was hydrogenated at 70 psi for 4 days, filtered through celite, solvent was removed, white solid was washed by Et$_2$O, and product was obtained as a white solid (206 mg, 98%).

Method N

Representative Example

Preparation of (Compound 890)

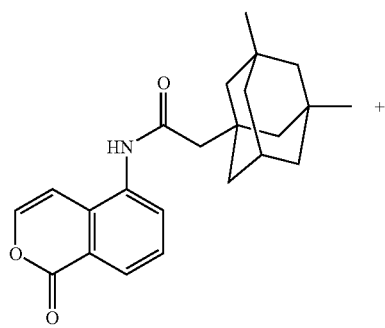

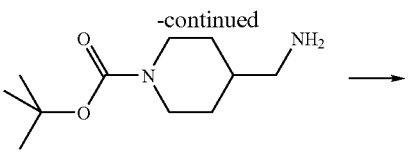

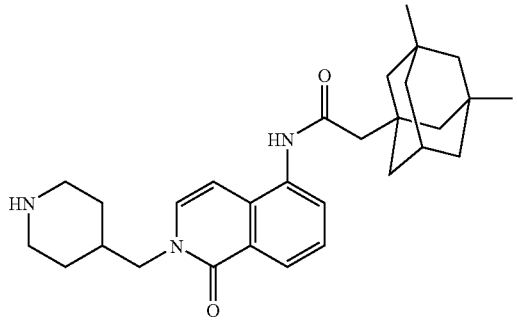

2-(3,5-Dimethyl-adamantan-1-yl)-N-(1-oxo-1H-isochromen-5-yl)-acetamide (200.0 mg, 0.49 mmol) was suspended in tert-butyl 4-(aminomethyl)piperidinecarboxylate (1.00 g, 4.67 mmol) and the reaction mixture was stirred at 140° C. overnight. EtOAc was added and the solution was washed by water and brine, dried over Na$_2$SO$_4$. Solvent was removed and the residue was dissolved in 1,2-dichloroethane (20 mL), 5 mL TFA was added and the solution was stirred at room temperature for 1 h. Volatiles were removed, residue was dissolved in the aqueous solution of NaOH and Na$_2$CO$_3$, extracted by EtOAc and purified by PTLC, compound was washed out from silica gel by MeOH. Solvent was removed, residue was triturated by Et$_2$O and the product was obtained as a beige solid (65 mg, 27%).

Method O

Representative Example

Preparation of (Compound 891)

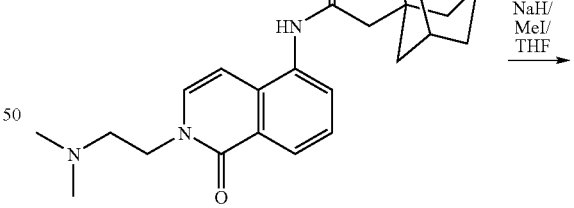

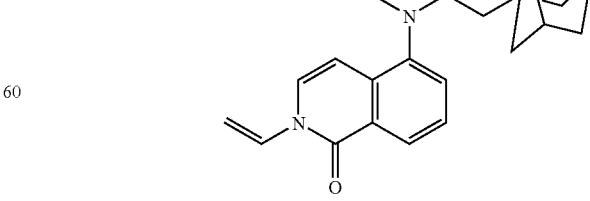

2-Adamantan-1-yl-N-[2-(2-dimethylamino-ethyl)-1-oxo-1,2-dihydro-isoquinolin-5-yl (60.0 mg, 0.14 mmol) was dissolved in THF (dry, 5 mL), NaH (95%, 30 mg) was added and the reaction mixture was stirred at room temperature for 10 min before methyl iodide (23.8 mg, 0.17 mmol) was added. The reaction mixture was stirred at room temperature overnight before quenching the reaction with MeOH. Volatiles were removed in vacuo and the residue subjected to silica gel purification. Product was obtained as a low-melting solid (35 mg, 66%).

Method P

Representative Example

Preparation of (Compound 893)

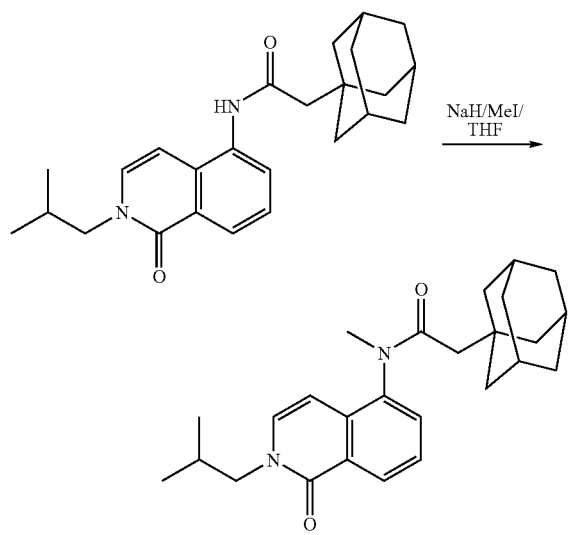

2-Adamantan-1-yl-N-(2-isobutyl-1-oxo-1,2-dihydro-isoquinolin-5-yl)-ace tamide (34.0 mg, 0.083 mmol) was dissolved in THF (1 mL), NaH (95%, ~10 mg) was added and the reaction mixture was stirred at room temperature for 10 min before methyl iodide (14.1 mg, 0.099 mmol) was added. The reaction mixture was stirred at room temperature for 2 h. Water was added and the mixture was extracted by EtOAc. Organic phase was washed by brine and dried over $Na_2SO_4$. Solvent was removed and residue was purified by HPLC to yield the product as a white solid (18.4 mg, 54%).

Method Q

Representative Example

Preparation of (Compound 894)

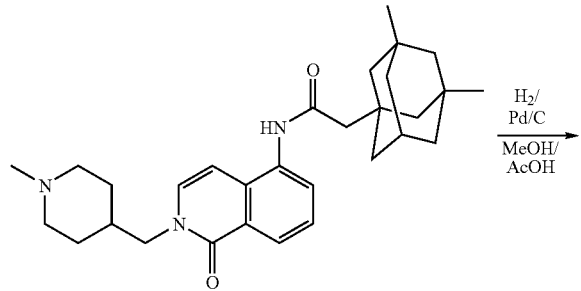

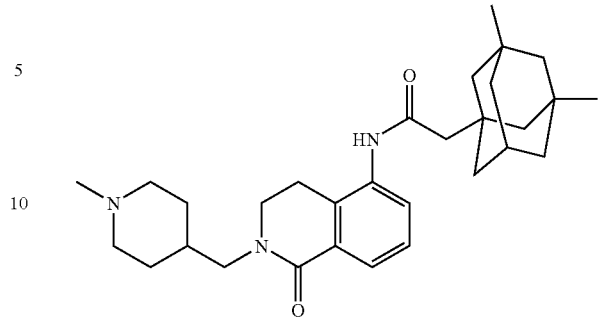

Appropriate starting material was dissolved in MeOH (10 mL) and AcOH (1 mL), Pd/C (10%) was added and the suspension was hydrogenated at 80 psi for 5~10 days. $Et_3N$ was added till pH ~10, then the suspension was filtered through celite®. Solvent was removed and residue was dissolved in EtOAc, washed with water and brine, dried over $Na_2SO_4$, solvent removed, and product obtained as a beige solid.

In addition to the compounds exemplified above and in Table 1, various other compounds, which comprise different substituted amides of this invention, can be prepared using the procedure and synthetic methods described above, or some modification thereof, and the corresponding starting materials, appropriate reagents, and purification methods known to those skilled in the art.

The following biological examples, Examples 1-9, are offered to illustrate the present invention and are not to be construed in any way as limiting its scope. In the examples below, all temperatures are in degrees Celsius (unless otherwise indicated).

EXAMPLE 1

The $P2X_7$ receptor is strongly expressed in macrophage-derived cell lines, including, but not limited to, J774 (mouse macrophage line, American Type Culture Collection (ATCC), Rockville, Md., ATCC TIB-67), P388 (mouse cell line, ATCC CCL-46), P815 (mouse mast cell mastocytoma-derived line, ATCC TIB-64), THP-1 (Human monocyte-derived cell line, ATCC TIB202) and U937 (human cell line derived from histiocytic lymphoma, induceable to monocyte differentiation, ATCC CRL-1593.2) and in isolated macrophage cultures. Human or non-human animal macrophages are isolated using the procedure noted below.

The $P2Z/P2X_7$ receptor can be characterized by measuring channel opening, for instance ion flux, and/or by assessing pore formation, including by monitoring dye uptake or cell lysis in cells naturally expressing this receptor. Compounds such as ATP, 2' and 3'-(O)-(4-benzoyl benzoyl) ATP (BzATP) effect the formation of pores in the plasma membrane of these cells, particularly at low extracellular divalent ion concentrations (Buisman et al, Proc. Natl. Acad. Sci. USA 85:7988 (1988); Zambon et al, Cell. Immunol 156:458 (1994); Hickman et al Blood 84:2452 (1994)). Large molecular size dyes, including propidium dye YO-PRO-1, can be seen entering macrophage-derived cell lines during cell recordings (Hickman et al, Blood 84:2452 (1994); Wiley et al, Br J Pharmacol 112:946 (1994); Steinberg et al, J Biol Chem 262:8884 (1987)). Ethidium bromide (a fluorescent DNA probe) can also be monitored, where an increase in the fluorescence of intracellular DNA-bound ethidium bromide is observed.

Expression of recombinant rat or human rP2X$_7$ in cells, including HEK293 cells, and in *Xenopus* oocytes demonstrates influx and pore formation by whole cell recordings and YO-PRO-1 fluorescence (Suprenant et al, Science 272:735 (1996); Rassendren et al, J Biol Chem 272:5482 (1997)).

The compounds of the invention may be tested for antagonist activity at the P2X$_7$ receptor. Tests that may be performed include and are selected from: (i) electrophysiological experiments; (ii) YO-PRO1 fluorescence; (iii) ethidium bromide fluorescence; and (iv) IL-1β release from stimulated macrophages, including as described below. Compounds can be tested in vivo in animal models including for inflammation models (e.g. paw edema model, collagen-induced arthritis, EAE model of MS).

Isolation of Human Macrophages

Monocyte-derived human or non-human animal macrophage cultures are prepared as described by Blanchard et al (Blanchard et al, J Cell Biochem 57:452 (1995); Blanchard et al, J Immunol 147:2579 (1991)). Briefly, monocytes are isolated from leukocyte concentrates obtained from a healthy volunteer. Leukocytes are suspended in RPMI 1460 medium (Life Technologies, Inc.) with 20% serum (human for human cells), 2 mM glutamine, 5 mM HEPES, and 100 µg/ml streptomycin. Cells are allowed to adhere to culture flasks for 1-2 h, after which nonadherent cells are washed away. Adherent cells are cultured for 7-14 d in this medium plus interferon-γ (human for human cells) (1000 units/ml). Macrophages are recovered from the culture flask by pipetting with cold phosphate-buffered saline and plated onto glass coverslips for electrophysiological or other experiments carried out 12-24 h later.

EXAMPLE 2

Electrophysiological Experiments

Whole cell recordings are made using the EPC9 patch-clamp amplifier and Pulse acquisition programs (HEKA, Lambrecht, Germany). Whole-cell recordings are obtained from cells, e.g. J774A.1 cells (American Type Culture Collection, Rockville, Md., ATCC TIB-67)); agonists are applied for periods of 1 to 3 s by a fast-flow U-tube delivery system [E. M. Fenwick, A. Marty, E. Neher, J. Physiol, (London) 331, 577 (1982)]. The internal pipette solution is 140 mM cesium-aspartate or potassium-aspartate, 20 mM NaCl, 10 mM EGTA, and 5 mM Hepes; normal external solution is 145 mM NaCl, 2 mM KCl, 2 mM CaCl$_2$, 1 mM MgCl$_2$, 10 mM Hepes, and 12 mM glucose. Low divalent external solution is nominally magnesium-free with 0.3 mM CaCl$_2$. Concentration-response curves are constructed in low divalent solution by recording currents in response to 1 s applications of agonist at 8 min intervals with normal external solution present for 6 min before each application. This protocol is necessary to prevent the development of sustained inward currents.

Reversal potentials (E$_{rev}$) are obtained by application of ATP (300 µM) or BzATP (30 µM) (controls), or the compound being tested, while the membrane is held at various potentials or by application of voltage ramps from −120 to 30 or 50 mV. Permeability ratios are calculated from E$_{rev}$ by first computing α(=P$_{Na}$/P$_K$, where P is permeability) for internal (i) and external (o) concentrations [Na]$_1$=20 mM, [Na]$_o$=145 mM, [K]$_o$=0 mM, and [K]$_1$=140 mM from α=([145/exp(E$_{rev}$FIRT)]−20)/140 (where F is the Faraday, R is the gas constant, and T is the absolute temperature). Other P$_x$/P$_{Na}$ values, when [X]$_o$=145 mM, [Na]$_1$=20 mM, [K]$_1$=140 mM, and [Na]$_o$=[K]$_o$=[X]$_1$=0 mM, are computed from P$_x$/P$_{Na}$=[(exp)E$_{rev}$/RT)](20+140α))/145. In order of size, X is cesium, methylamine, tris(hydroxymethyl)-aminomethane, tetraethylammonium, and N-methyl-D-glucamine. The internal solution also contains 10 mM EGTA and 5 mM Hepes. External solutions also contain 10 mM glucose and normal or low concentrations of divalent cations; pH is maintained at 7.3 with HCl, histidine, or Hepes as required, and the osmolarity of all solutions is 295 to 315.

EXAMPLE 3

YO-PRO1 Fluorescence

The Photonics Imaging (IDEA) system for microscopic fluorescence measurements (Photonics, Planegg, Germany) is used. Coverslips are placed at the stage of a Zeiss Axiovert 100 or equivalent inverted microscope and viewed under oil immersion with a 40× Fluor objective. YO-PRO-1 (10 µM; Molecular Probes, Eugene, Oreg.) is added to the superfusion fluid during electrophysiological recordings 3 to 6 min before switching to low divalent solution and washed out upon switching back to normal divalent solution, after which the fluorescent lamp is turned on and cells are examined with a fluorescein isothiocyanate filter. YO-PRO1 fluorescence is measured using 491/509 nm excitation/emission wavelengths. Images are obtained at 5-20 s intervals during continuous superfusion (2 ml/min) with YO-PRO1 and varying concentrations of control ATP, BzATP or compound to be tested. For each experiment, the time course of YO-PRO1 fluorescence is obtained for 10-20 individual cells and then averaged to obtain the mean fluorescence signal. Results are expressed as mean signal at 3 min for rP2X$_7$, and the signal at 10 min is used for P2X$_7$ and human macrophage cells. All experiments are carried out at room temperature.

EXAMPLE 4

Ethidium Bromide

Compounds of the invention are tested for antagonist activity at the P2X$_7$ receptor by monitoring Ethidium Bromide entering P2X$_7$ receptor-expressing cells on pore formation. The test is performed in 96-well flat bottomed microtitre plates, the wells being filled with 250 µl of test solution comprising 200 µl of a suspension of P2X$_7$-expressing cells (e.g. THP-1 cells, J774 cells, etc.)(2.5×10$^6$ cells/ml) containing 10$^{-4}$M ethidium bromide, 25 µl of a high potassium buffer solution containing 10$^{-5}$M BzATP, and 25 µl of a high potassium buffer solution containing test compound. The plate is covered with a plastic sheet and incubated at 37° C. for one hour. The plate is then read in a Perkin-Elmer fluorescent plate reader, excitation 520 nm, emission 595 nm, slit widths: Ex 15 nm, EM 20 nm. For the purposes of comparison, BzATP (a P2X$_7$ receptor agonist) and pyridoxal 5-phosphate (a P2X$_7$ receptor agonist) are used separately in the test as controls. From the readings obtained, a pIC$_{50}$ figure is calculated for each test compound. This figure is the negative logarithm of the concentration of test compound necessary to reduce the BzATP agonist activity by 50%.

EXAMPLE 5

IL-1β Release

This Example demonstrates the testing of the compounds of this invention for efficacy as inhibitors of P2X$_7$-mediated release of IL-1β from human macrophages activated by the Alzheimer's beta amyloid peptide 1-42.

Cell Isolation

Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (generally, 5 to 6 washes). Monocytes are then purified from the PBMCs by negative selection using a monocyte isolation kit (Miltenyi Biotec, Inc.) that contains antibodies to non-monocytic cells, running the cells over a magnetic column to remove antibody-bound cells, and collecting the flow through volume of monocytes. Monocytes are washed once with wash buffer and seeded at 10E5 cells per well in 100 µl serum-free RPMI 1640 in 96-well plates and incubated for 1 hour at 37° C. in a 5% $CO_2$/95% humidified tissue culture incubator. After 1 hour, the medium is replaced with 100 µl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing Regimen

The next day, the culture medium is replaced with 100 µl fresh complete culture medium in the absence or presence of human beta amyloid 1-42 peptide (5 µM) and incubated at 37° C. in a 5% $CO_2$/95% humidified tissue culture incubator for 5 hours. Medium is then removed and discarded. Each well is washed once with Hanks buffered saline (HBSS) containing 1 mM $CaCl_2$ followed by the addition of 80 µl of HBSS/$CaCl_2$-inhibiting compound of the present invention (10× stock in HBSS/$CaCl_2$ for a final concentration of 23 nM and 206 nM) and incubated 15 minutes in the tissue culture incubator followed by the addition of either 10 µl of HBSS/$CaCl_2$ or 10 µl of benzoyl ATP (BzATP; 3 mM stock in HBSS/$CaCl_2$ for a 300 µM final concentration) and incubated for a further 30 minutes in the tissue culture incubator. Medium is then removed to new 96-well plates for storage at −70° C. until the IL-1β content is quantitated by ELISA (from R&D Systems). The cells are washed once with HBSS/$CaCl_2$ followed by lysing the cells with 100 µl ice cold lysis buffer (100 mM Tris, pH 7.6, 1% Triton X-100, and 1 tablet per 30 ml Complete TM protease inhibitor from Roche Biochemicals, Inc). Cell lysates are stored at −70° C. until the IL-1β is quantitated by ELISA.

EXAMPLE 6

In Vivo Animal Models

A. This example illustrates the efficacy of the compounds of this invention in the treatment of multiple sclerosis. As described herein, an experimental autoimmune encephalomyelitis (EAE) model is used to show such efficacy. The following procedures are employed in this model.

Animals

SJL/J female mice, 8 wks. old, are obtained from Jackson Laboratories.

Antigens

Myelin Proteolipid Protein (PLP 139-151) (HSLGK-WLGHPDKF) (Cat #H-2478) is obtained from BACHEM, Bioscience, Inc., King of Prussia, Pa.

Complete Freund's Adjuvant H37 Ra [1 mg/ml *Mycobacterium Tuberculosis* H37 Ra] is obtained from Difco (Cat #3114-60-5, 6×10 ml).

*Mycobacterium Tuberculosis* is also obtained from Difco, (Cat #3114-33-8, 6.times.100 mg).

*Pertussis* Toxin

*Bordetella Pertussis*, (Lyophilized powder containing PBS and lactose) is obtained from List Biological Laboratories, (Product #180, 50 ug).

Induction of EAE in Mice

PLP139-151 peptide is dissolved in $H_2O$:PBS (1:1) solution to a concentration 7.5 mg/10 ml (for 75 µg PLP per group) and emulsified with an equal volume of CFA supplemented with 40 mg/10 ml heated-killed *mycobacterium tuberculosis* H37Ra. Mice are injected s.c. with 0.2 ml of peptide emulsion in the abdominal flank (0.1 ml on each side). On the same day and 72 hours later, mice are injected i.v. with 100% of 35 ng and 50 ng of *Bordetella Pertussis* toxin in saline respectively.

Clinical Assessment

STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE Clinical Courses of EAE Acute phase: First clinical episode (Day 10-18)

Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

B. This Example illustrates a protocol for determining the efficacy of the compounds of the present invention for the treatment of stroke using an animal model.

Male Sprague Dawley rats (Charles River) weighing 280-320 g are given free access to food and water and acclimatized for a minimum of 4 days before use in experiments. All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.

Surgical Procedure

A temporalis muscle probe is placed into the right temporalis muscle and "brain" temperature" is monitored. A midline neck incision is made in the upper thorax of the rat. Careful dissection, isolation and retraction of the stemomastoideus, digastricus, and sternohyoideus muscles is made to expose the right common, internal and external carotid arteries. The right common carotid artery is isolated with a 5-0 silk suture. During surgery the suture is released allowing reperfusion every 2-4 minutes. The right external carotid and superior thyroid arteries are also isolated and the superior thyroid is cauterized, while the external carotid is ligated distally with a 5-0 silk suture. Another 5-0 silk suture is loosely tied around the external carotid artery. The occipital artery is isolated, ligated and incised. The internal carotid is isolated.

With the common and external carotid arteries immobilized, an aneurysm clip is placed onto the internal carotid artery. A small incision is made at the distal end of the external carotid. A 3-0 nylon suture coated with poly-L-lysine is then inserted into the external carotid and up into the common carotid artery. The loosely tied 5-0 silk suture around the external carotid is now gently tightened around the filament. The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing <300 gm, 19 mm for rats weighing 300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture. The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%. The neck incision is reopened to expose the external carotid artery. The restoration of blood flow is accomplished by completely withdrawing the intraluminal suture from the carotid arteries. The incision is then closed with 3-0 silk in an interrupted stitch.

Compound Administration

Five groups of 15 animals are subjected to the above methodology. Compounds are infused (I.V.) at various doses (dose response) over different time periods post MCAo. A predetermined concentration is infused over a pre-selected time period beginning at various intervals post MCAo. Vehicle-treated controls receive an infusion of normally 0.9 ml/hr. A positive control compound is run at the same time.

Neurological Tests

Prior to surgery, 2 hours following the onset of ischaemia and 24 hours after ischaemia, a battery of neurological tests are performed. The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation.

The rats' response to a gentle lateral push with a finger behind the shoulders is observed and noted. A normal rat would resist such a push, whereas a rat with an infarction will not. The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

C. This Example illustrates the anti-inflammatory activity of the compounds of this invention using a model of 2,4-dinitrobenzenesulfonic acid (DNBS) induced distal colitis (a model of inflammatory bowel disease).

Test Substance and Dosing Pattern

A compound of this invention is dissolved in vehicle of 2% Tween 80 in distilled water for oral administration at a dose of 50 mg/kg or dissolved in vehicle of 2% Tween 80 and 0.9% NaCl for intraperitoneal injection at 30 mg/kg. The dose is given once daily for 7 consecutive days. Dosing volume was 10 ml/kg. DNBS is challenged 2 hours after dosing on the second day.

Animals

In these studies, male Wistar, Long Evans rats provided by the animal breeding center of MDS Panlabs Taiwan, Ltd. and Balb/cByJ derived male mice (weighing 20±2 gms), provided by National Laboratory Animals Breeding Research center (NALBRC, Taiwan), may be used. Space allocation of 6 animals may be 45×23×5 cm. Animals are housed in APEC® cages (Allentown Caging, Allentown, N.J. 08501, USA) in a positive pressure isolator (NuAire®, Mode: Nu-605, airflow velocity 50±5 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water is granted. All aspects of this work including housing, experimentation and disposal of animals would be performed in general accordance with the International Guiding Principles for Biomedical Research Involving Animals (CIOMS Publication No. ISBN 92 90360194, 1985).

Chemicals

DNBS is obtained from TCI, Tokyo, Japan, ethanol is from Merck, Germany and Sulfasalazine is purchased from Sigma, USA.

Equipment

Electriconic scale (Tanita, Model 1140, Japan), Electriconic scale (Sartorius, R160P, Germany), Glass syringe (2 ml, Mitsuba, Japan), Rat oral needle, Hypodermic needle (25 G×1" TOP Corporation, Japan), Stainless Scissors (Klappenclear, Germany), Stainless Forceps (Klappenclear, Germany).

Method

Groups of 3 Wistar derived male rats weighing 180±20 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instilled into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon is removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW×100%. The "Net" increase in ratio of Vehicle-control+DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

D. This Example illustrates the anti-inflammatory activity of the present compounds using a model of carrageenan induced paw edema (a model of inflammation, carrageenan).

Test Substance and Dosing Pattern

A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.

Animals

Animals are conditioned in accordance with the procedures set forth in the previous Example.

Chemicals

Carrageenan is obtained from TCI, Japan; Pyrogen free saline is from Astar, Taiwan; and Aspirin is purchased from ICN BioMedicals, USA.

Equipment

Glass syringe (1 ml and 2 ml Mitsuba, Japan), Hypodermic needle 24 G×1" (Top Corporation, Japan), Plethysmometer #7150 (Ugo Basile, Italy), and Water cell 25 mm Diameter, #7157 (UGO Basile, Italy).

Method

Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. #7150) with water cell (25 mm diameter, Cat. #7157). Reduction of hind paw edema by 30 percent or more (30%) indicated significant acute anti-inflammatory activity.

E. This Example illustrates the anti-inflammatory activity of the present compounds using a model of Balb/c mice subjected to monoclonal antibody (mAb) type II collagen induced arthritis.

Test Substance and Dosing Pattern

A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen is injected. Dosing volume is 20 ml/kg.

Animals

Animals are conditioned in accordance with the procedures set forth in the previous Example.

Chemicals

Lipopolysaccharide is obtained from Sigma, USA; Indomethacin is from Sigma, USA; Arthrogen-CIA™ Monoclonal Antibodies D8, F10, DI-2G and A2 are obtained from IBL, Japan; Phosphated-Buffer Saline is purchased from Sigma, USA; and Tween 80 is from Wako, Japan.

Equipment

Plethysmometer (Ugo Basile, Italy) and Water Cell (Ugo Basile, Italy).

Method

Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mAbs in a total of 4 mg/mouse at day 0, and followed by intravenous 25 µg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administered once daily for 3 consecutive days. A plethysmometer (Ugo Basile Cat #7150) with water cell (12 mm diameter) is used for the measurement of increase in volume of the two hind paws at day 0, 5, 7, 10, 14, and 17. The percent inhibition of increase in volume is calculated by the following formula:

$$\text{Inhibition (\%)}: [1-(T_n-T_0)/(C_n-C_0)] \times 100$$

Where:

Co (Cn): volume of day 0 (day n) in vehicle control

To (Tn): volume of day 0 (day n) in test compound-treated group

The reduction of both of two hind paws edema by more than 30% is considered significant.

EXAMPLE 7

Neuropathic Pain Model

This example illustrates the analgesic activity of the compounds of this invention using a Sciatic Nerve ligation model of mononeuropathic pain.

Test System

Adult male Sprague Dawley (SD) rats weighing 250-300 gm (Charles River Laboratories, San Diego, Calif.) are used. The animal room is lighted artificially at a 12-hr light-dark cycle (e.g. from 7:00 A.M. to 7:00 P.M) with water and food supply ad libitum. Animals are allocated randomly into groups.

Model Induction

Sciatic nerve ligation (SNL, Seltzer's model):

Under anesthesia with pentobarbital (50 mg/kg, i.p.) and aseptic techniques, the selective nerve injury is created by tightly ligating the selective portion of the common sciatic nerve according to the method of Seltzer (1990). Briefly, the high-thigh level of the left sciatic nerve is exposed after skin incision and blunt separation of muscles at a site near the trochanter just distal to the point at which the posterior biceps semitendious nerve branches from the common sciatic nerve. The nerve is then fixed in this position with fine forceps by pinching the epineurium on its dorsal aspect, taking care not to press the nerve against underlying structures. An 8-0 silicon-treated silk suture is inserted into the nerve with a ⅜ curved, reversed-cutting mini-needle, and tightly ligated so that the dorsal ⅓-½ of the nerve is trapped in the ligature. The muscles are sutured in layers, and the skin closed with wound clips. Animals are then returned to their home cages. Rats exhibiting postoperative neurological deficits or poor grooming are excluded from the experiments.

Equipment

The following equipment is used in the current studies: von Frey filament set (Touch-test Sensory Evaluator, North Coast Medical Inc., Morgan Hill, Calif.).

Statistical Methods:

Within each experiment mean, standard error of the mean (SEM) and statistical significance are calculated using the average, standard error of the mean and unpaired, two-tailed t-Test functions, respectively, using Microsoft Excel®. Statistical significance of effects observed between individual experiments is determined, using Prism (GraphPad Software Inc., San Diego, Calif.). for the one-way or two-way analysis of variance (ANOVA) function. Statistical analyses are performed with a confidence limit of 0.95 and a significance level of 0.05.

EXAMPLE 8

Pore Formation

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 IU/mL penicillin, 100 ug/mL streptomycin, 100 ng/mL LPS and 100 ng/mL IFN-γ for 16 hours. Following differentiation, the cells are pretreated with the compound of interest at the appropriate concentration for 30 minutes in RPMI-1640 media containing 100 IU/mL penicillin, 100 ug/mL streptomycin. The pretreatment media is then replaced with assay buffer (20 mM HEPES, 10 mM D-glucose, 118 mM NMDG, 5 mM KCl, 0.4 mM $CaCl_2$) containing 5 uM Yo-Pro 1 (Molecular Probes Cat #Y3603) and the compound of interest at the appropriate concentration and the cells are incubated for an additional 10 minutes. 2',3'-O-(4-benzoylbenzoyl)-adenosine 5'-triphosphate (Sigma Aldrich Cat #B6396) is then added to a final concentration of 40 uM and fluorescence readings measured at 491/509 excitation/emission every minute for 50 minutes using a Tecan Safire plate reader. During this time temperature is maintained at of 37° C. Background adjusted fluorescence levels between drug treated and non-treated cells are used to calculate the percent inhibition.

EXAMPLE 9

IL-1, Release Assay (Alternate Method)

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 U/mL penicillin, 100 ug/mL streptomycin, 100 ng/mL LPS and 100 ng/mL IFN-γ for 16 hours. Following differentiation, the cells are treated for an additional 2 hours in RPMI-1640 media containing 100 IU/mL penicillin, 100 ug/mL streptomycin and fresh LPS at 100 ng/mL. The cells are then pretreated for 30 minutes with the compound of interest at the appropriate concentration in RPMI media containing 100 IU/mL penicillin, 100 ug/mL streptomycin. Following the pretreatment 2',3'-O-(4-benzoylbenzoyl)-adenosine 5'-triphosphate (Sigma Aldrich Cat #B6396) is added to a final concentration of 250 uM and the cells incubated for an additional 45 minutes. 30 uL of cell supernatant is then collected and IL-1β levels determined via ELISA (R&D systems Cat. #HSLB50) according to manufacturer's recommendations using the Tecan Safire plate reader. Background adjusted IL-1β levels of drug treated and non-treated cells are used to calculate the percent inhibition.

The synthetic and biological examples described in this application are offered to illustrate this invention and are not to be construed in any way as limiting the scope of this invention. In the examples, all temperatures are in degrees Celsius (unless otherwise indicated). The compounds that have been prepared in accordance with the invention along with their biological activity data are presented in the following Table (Table 1). The syntheses of compounds of this invention are carried out in accordance with the methods set forth above.

Exemplary Compounds of the Invention

The following compounds have been or can be prepared according to the methods of the invention. For purposes of the Table 1 below, activity of each compound is expressed as follows:

TABLE 1

Amide Compounds

| ID | Structure | MW (calcd) | MS (obs) | Synthetic Method | Synthetic Method Comments | IL-1β % Inhibition |
|---|---|---|---|---|---|---|
| 701 | 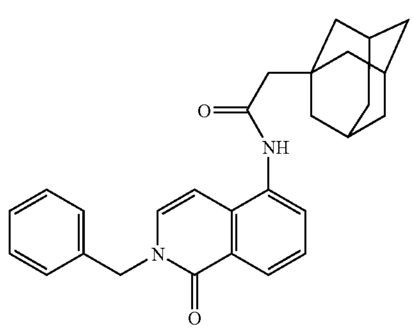 | 426.56 | 427.59 | A1 | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 702 | 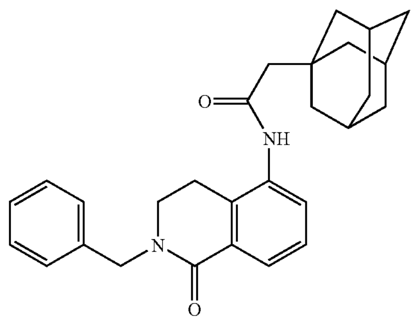 | 428.57 | 429.41 | A2 | | ++++ |
| 703 | 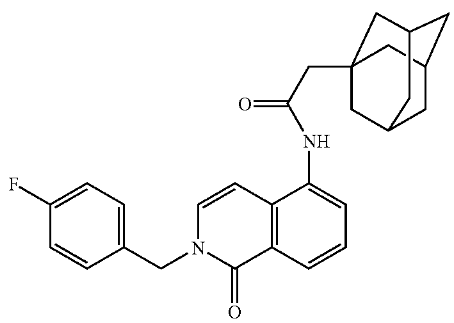 | 444.55 | 445.65 | B | | ++++ |
| 704 | 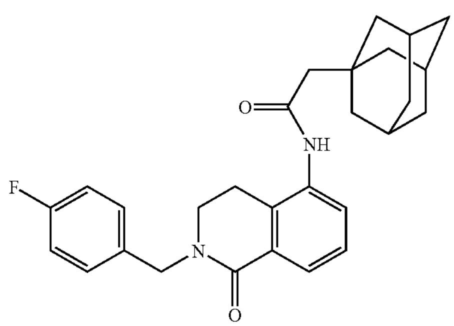 | 446.56 | 447.50 | A2 | | ++++ |
| 705 | 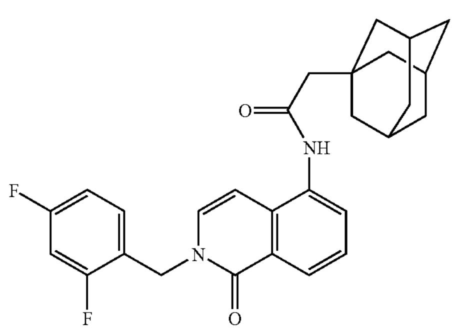 | 462.54 | 463.36 | B1 | | ++++ |

TABLE 1-continued
Amide Compounds
| ID | Structure | MW (calcd) | MS (obs) | Synthetic Method | Synthetic Method Comments | IL-1β % Inhibition |
|---|---|---|---|---|---|---|
| 706 | 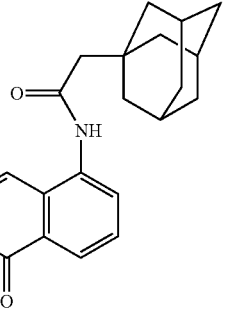 | 444.55 | 445.32 | B1 | | ++++ |
| 707 | 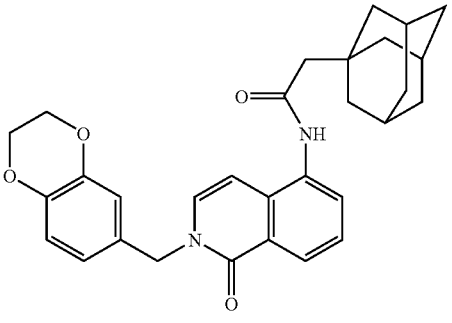 | 484.59 | 485.30 | B1 | | ++++ |
| 708 | 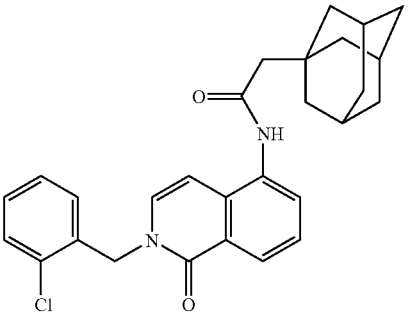 | 461.00 | 461.44 | Other, see Comment Column | Pyrone (30 mg, 0.089 mmol) + Amine (13 mg, 0.089 mmol) in DMA(0.1 mL), 135° C., 6 h | ++++ |
| 709 | 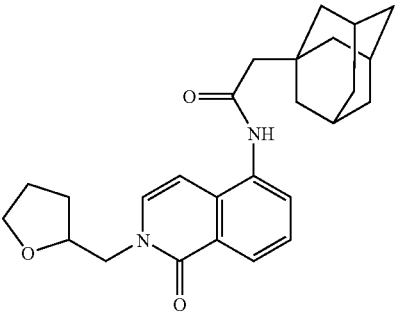 | 420.55 | 421.25 | B1 | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 710 | 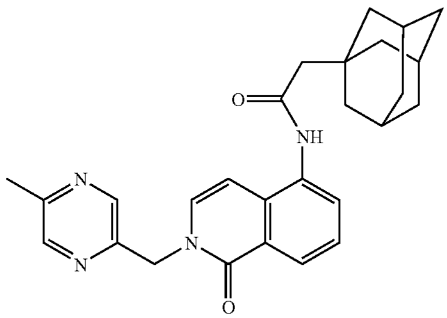 | 442.56 | 443.50 | B1 | | ++++ |
| 711 | 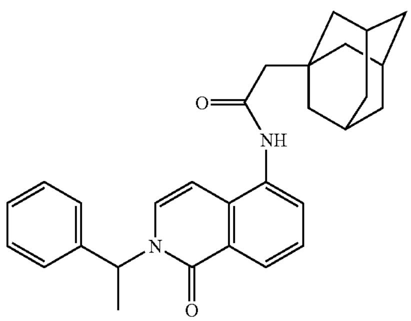 | 440.58 | 441.39 | B1 | | ++++ |
| 712 | 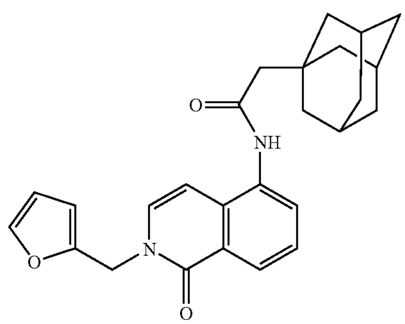 | 416.52 | 417.27 | B1 | | ++++ |
| 713 | 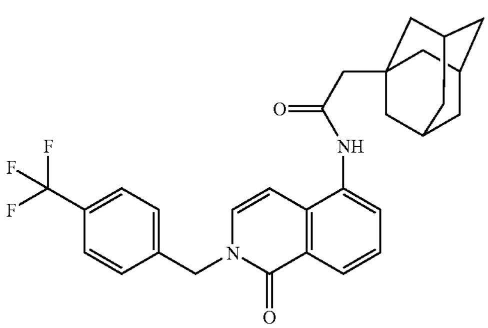 | 494.55 | 495.33 | Modified B1, see comments column | Similar to B1, reaction temperature was 140° C. | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 714 | 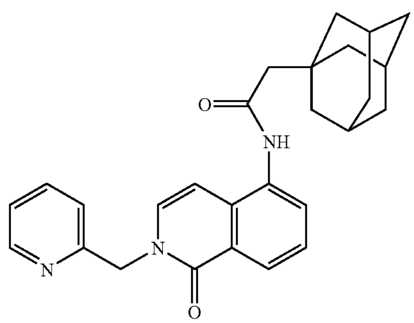 | 427.55 | 428.22 | Modified B1, see comments column | Similar to B1, reaction temperature was 140° C. | ++++ |
| 715 | 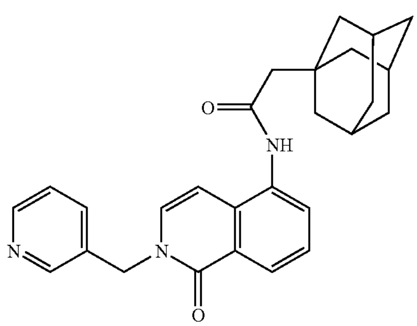 | 427.55 | 428.22 | B1 or Modified B1 | Similar to B1, reaction temperature was 140° C. | ++++ |
| 716 | 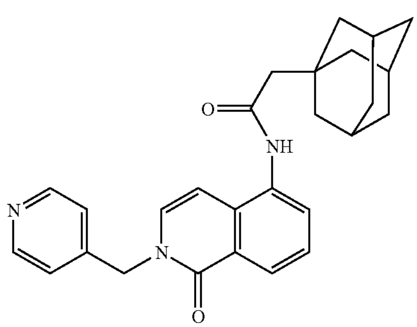 | 427.55 | 428.21 | B1, see comments column | Similar to B1, reaction temperature was 140° C. | ++++ |
| 717 | 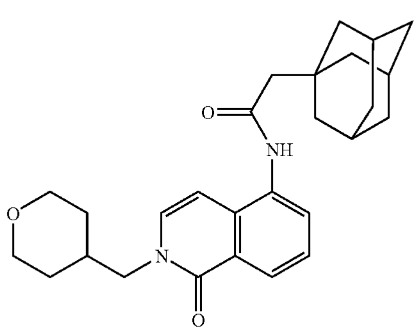 | 434.58 | 435.32 | B1 or Modified B1 | Similar to B1, reaction temperature was 140° C. | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 718 | 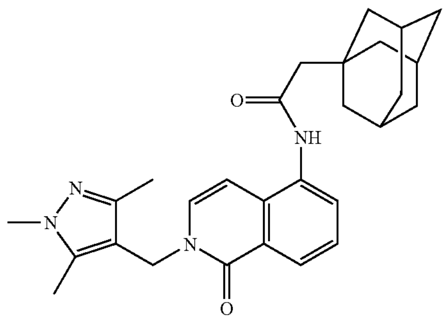 | 458.60 | 459.37 | B1, see comments column | Similar to B1, reaction temperature was 140° C. | ++++ |
| 719 | 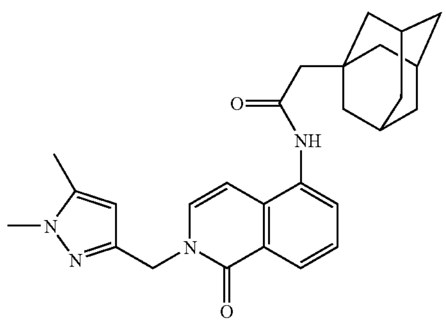 | 444.58 | 445.41 | B1, see comments column | Similar to B1, reaction temperature was 140° C. | ++ |
| 720 | 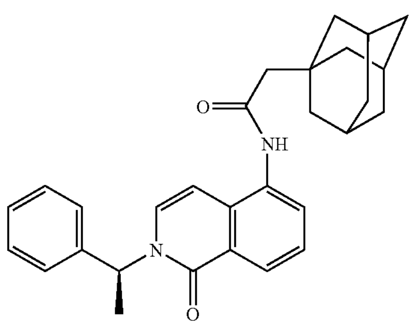 | 440.58 | 441.32 | Modified B1, see comments column | Similar to B1, reaction temperature was 140° C. | ++++ |
| 721 | 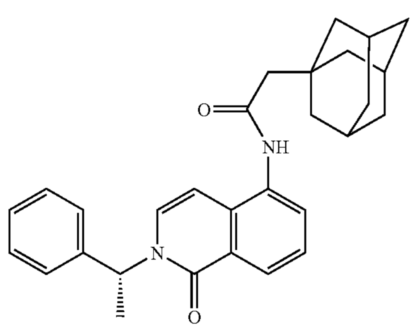 | 440.58 | 441.32 | Modified B1, see comments column | Similar to B1, reaction temperature was 140° C. | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 722 | 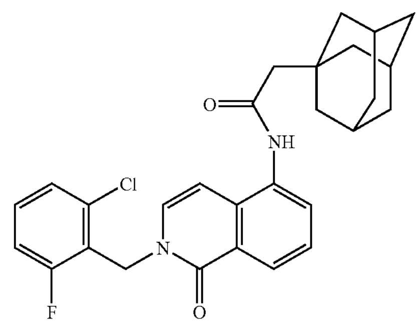 | 478.99 | 478.91 | Modified B1, see comments column | Similar to B1, reaction temperature was 140° C., reaction time 70 h | ++++ |
| 723 | 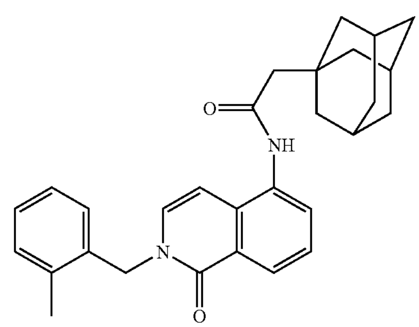 | 440.58 | 441.13 | Modified B1, see comments column | Similar to B1, reaction temperature was 140° C., reaction time 70 h | ++++ |
| 724 | 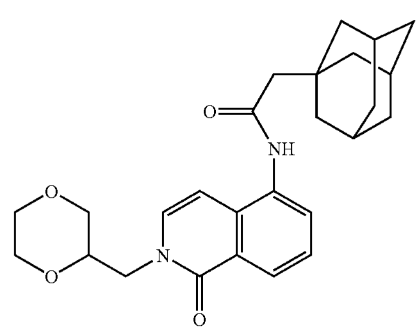 | 436.55 | 437.27 | Modified B1, see comments column | Similar to B1, reaction temperature was 140° C., reaction time 70 h | ++++ |
| 725 | 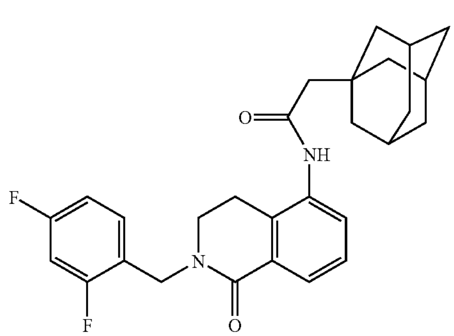 | 464.55 | 465.28 | D | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 726 | 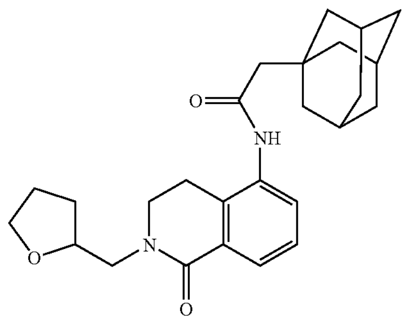 | 422.57 | 423.14 | D | | ++++ |
| 727 | 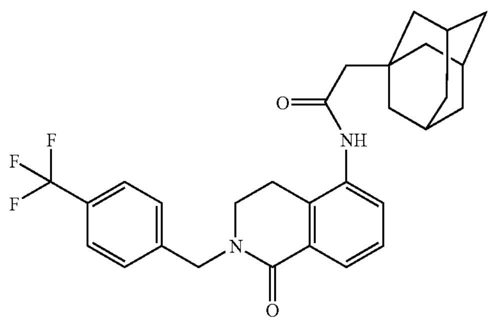 | 496.57 | 497.17 | D | | ++++ |
| 728 | 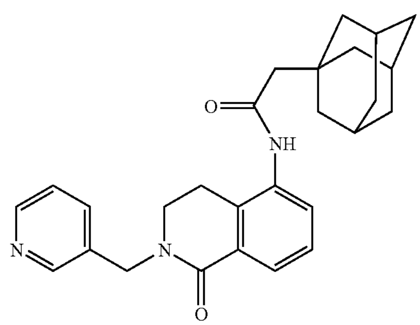 | 429.56 | 430.18 | D | | ++++ |
| 729 | 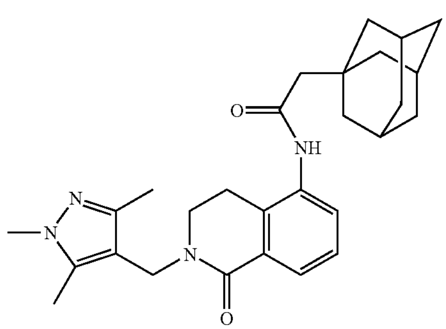 | 460.62 | 461.41 | D | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 730 | 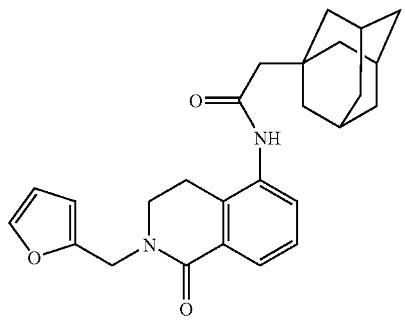 | 418.53 | 419.27 | D | | ++++ |
| 731 | 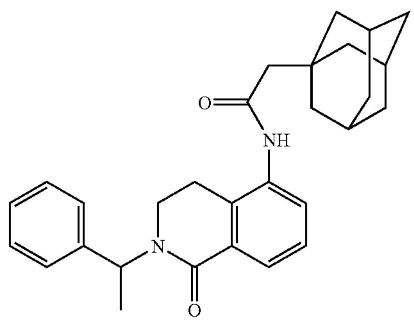 | 442.60 | 443.26 | D | | ++++ |
| 732 | 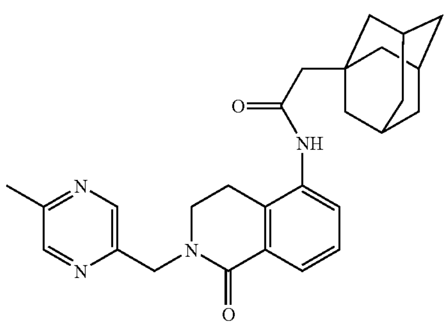 | 444.58 | 445.45 | D | | ++++ |
| 733 | 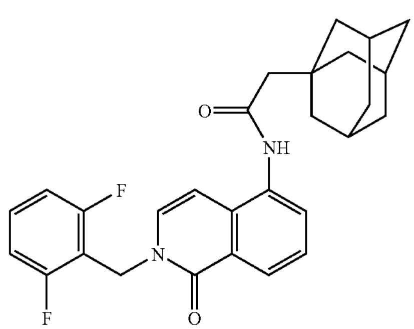 | 462.54 | 463.24 | Modified B1, see comments column | Similar to B1, reaction temperature was 140° C., reaction time 70 h | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 734 | 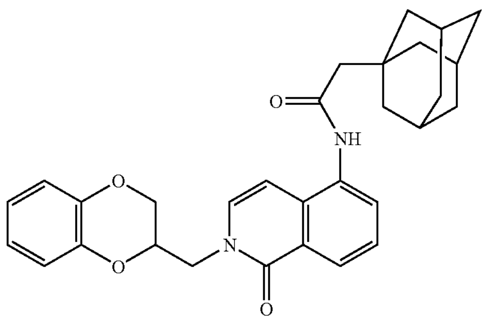 | 484.59 | 485.17 | Modified B1, see comments column | Similar to B1, reaction temperature was 140° C., reaction time 70 h | ++++ |
| 735 | 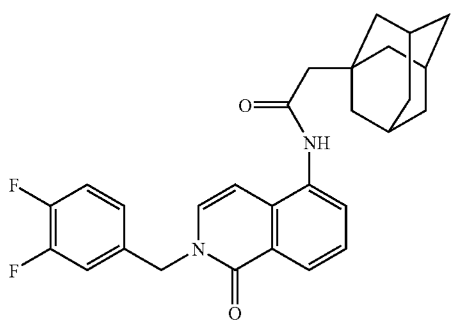 | 462.54 | 463.24 | Modified B1, see comments column | Similar to B1, reaction temperature was 140° C., reaction time 70 h | ++++ |
| 736 | 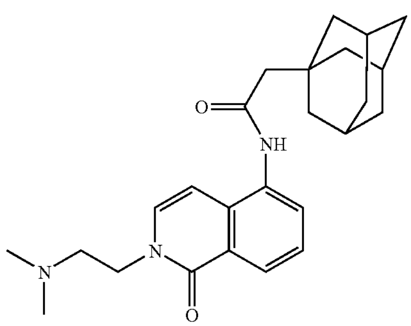 | 407.55 | 408.31 | B1 or Modified B1 | Similar to B1, reaction temperature was 140° C., reaction time 70 h | ++++ |
| 737 | 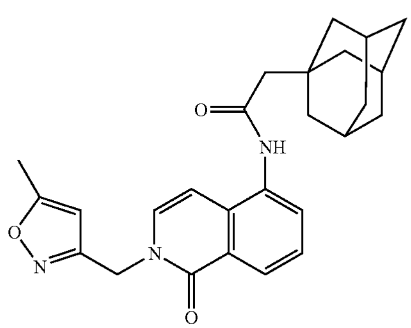 | 431.53 | 432.30 | Modified B1, see comments column | Similar to B1, reaction temperature was 140° C., reaction time 70 h | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 738 | 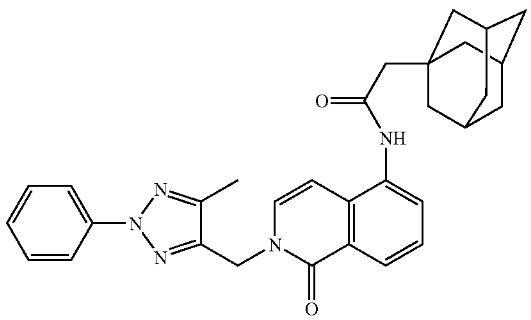 | 507.63 | 508.19 | Modified B1, see comments column | Similar to B1, reaction temperature was 140° C., reaction time 70 h | ++++ |
| 739 | Chiral | 420.55 | 421.13 | Modified B1, see comments column | Similar to B1, reaction temperature was 140° C., reaction time 70 h | ++++ |
| 741 | 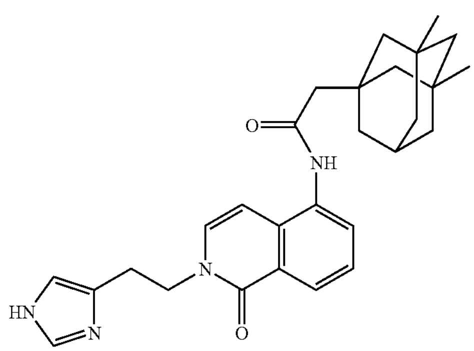 | 458.60 | 459.47 | B1 | | ++++ |
| 742 | 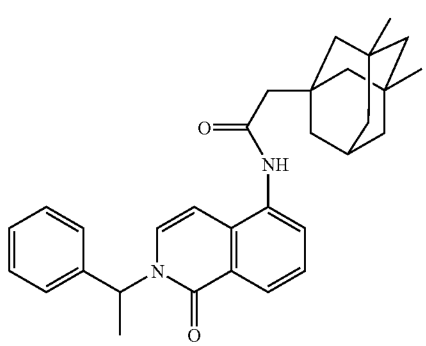 | 468.64 | 469.48 | B1 | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 743 | 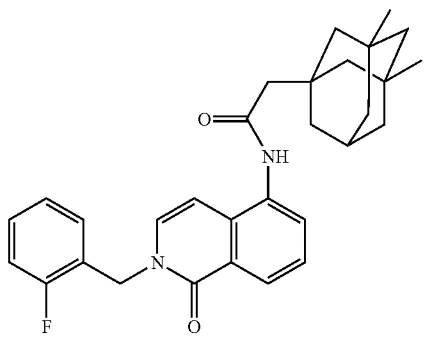 | 472.60 | 473.19 | B1 | | ++++ |
| 744 | 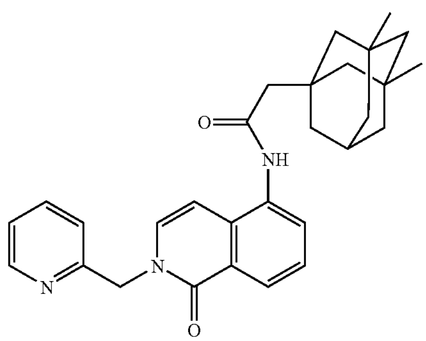 | 455.60 | 455.25 | B1 | | ++++ |
| 745 | 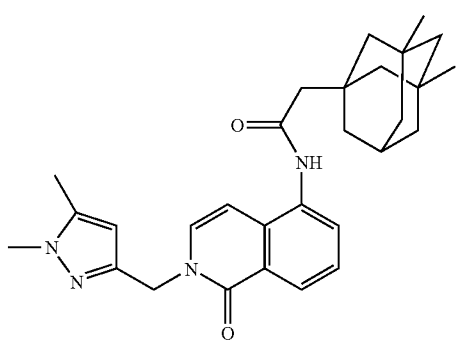 | 472.63 | 473.25 | B1 | | ++++ |
| 746 | 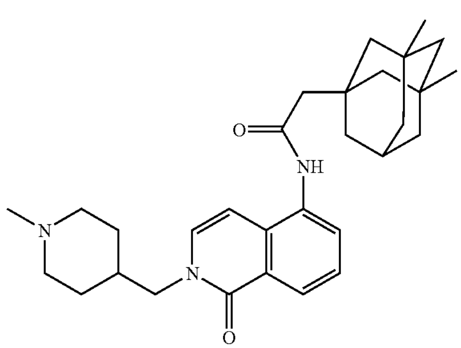 | 475.67 | 476.32 | B1 | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 747 | 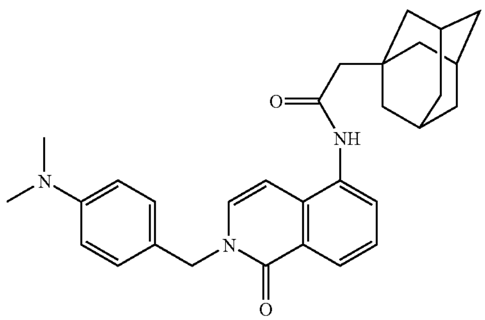 | 469.63 | 470.14 | Modified B1, see comments column | Similar to B1, reaction temperature was 140° C., reaction time 70 h | ++++ |
| 748 | 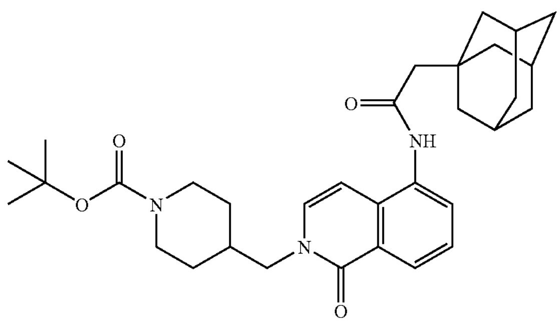 | 533.71 | 534.15 | Modified B1, see comments column | Similar to B1, reaction temperature was 140° C., reaction time 70 h | ++++ |
| 749 | 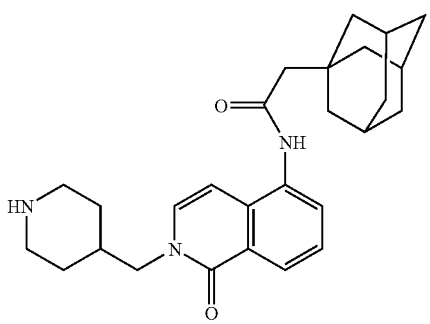 | 433.59 | 434.42 | Modified B1, see comments column | Similar to B1, reaction temperature was 140° C., reaction time 70 h | ++++ |
| 750 | 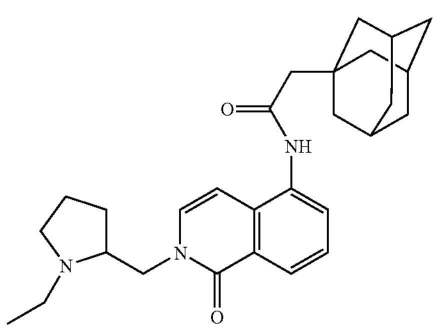 | 447.62 | 448.19 | Modified B1, see comments column | Similar to B1, reaction temperature was 140° C., reaction time 70 h | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 751 | 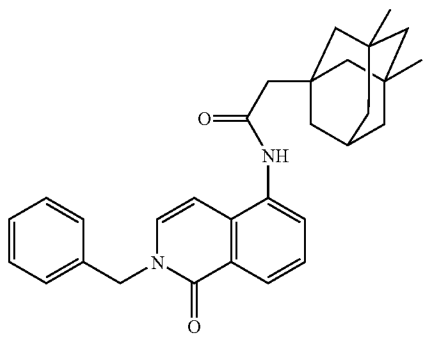 | 454.61 | 455.28 | B1 | | *** |
| 752 | 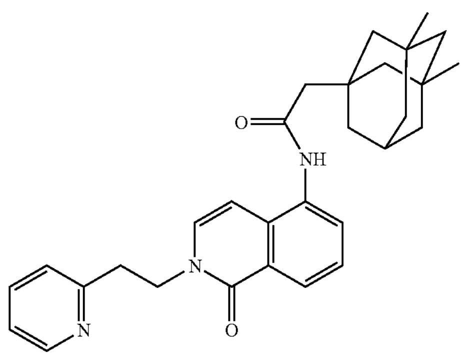 | 469.63 | 470.42 | B1 | | *** |
| 753 | 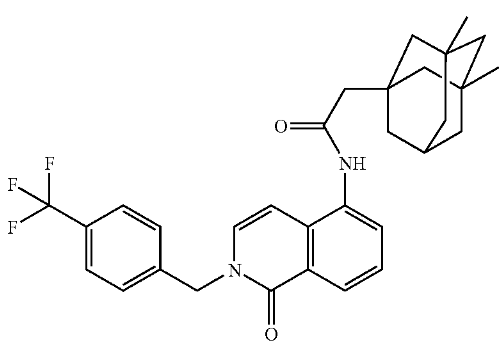 | 522.61 | 523.50 | B1 | | **** |
| 754 | 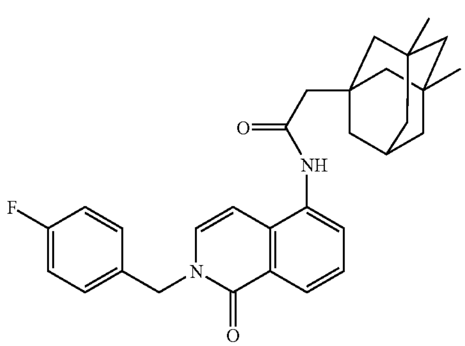 | 472.60 | 473.22 | B1 | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 755 | 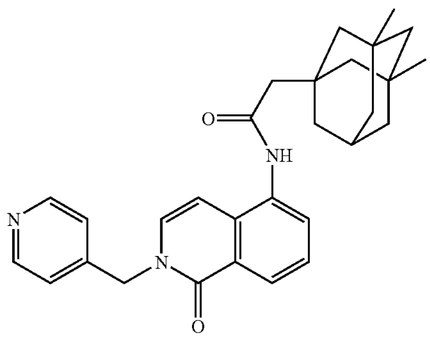 | 455.60 | 456.30 | B1 | | **** |
| 756 | 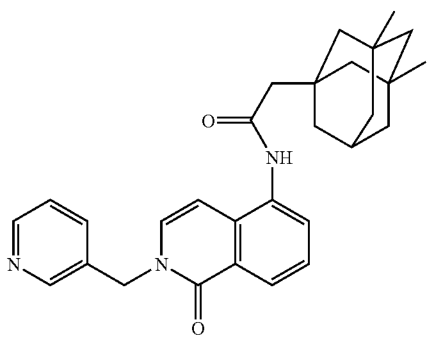 | 455.60 | 456.30 | B1 | | *** |
| 757 | 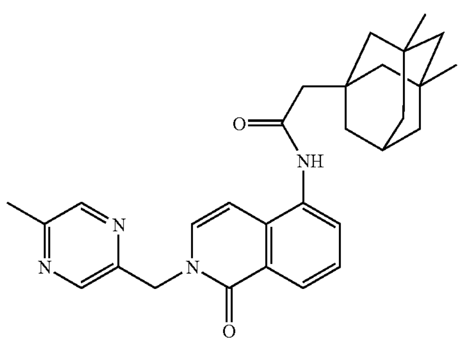 | 470.61 | 471.55 | B1 | | **** |
| 758 | 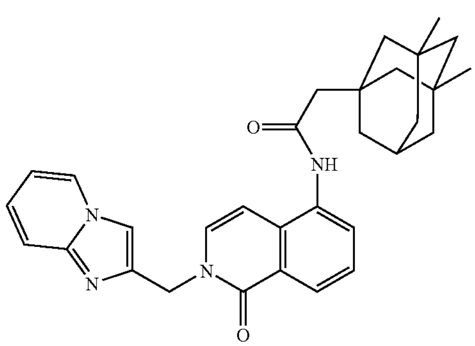 | 494.64 | 495.30 | B1 | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 759 | 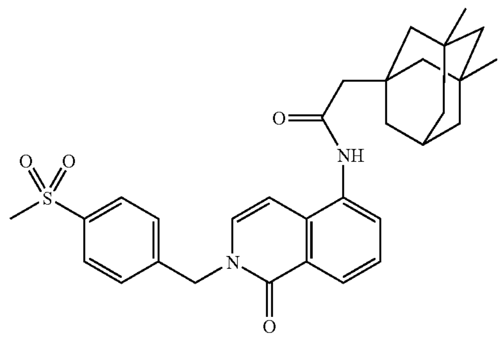 | 532.70 | 533.20 | B1 | | *** |
| 760 | 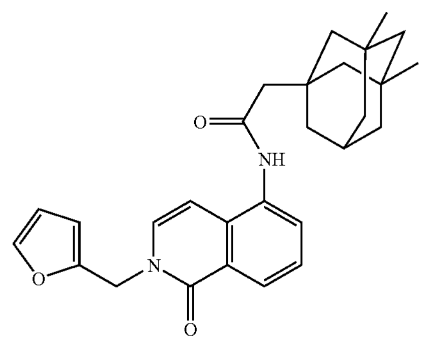 | 444.57 | 445.50 | B1 | | ** |
| 761 | 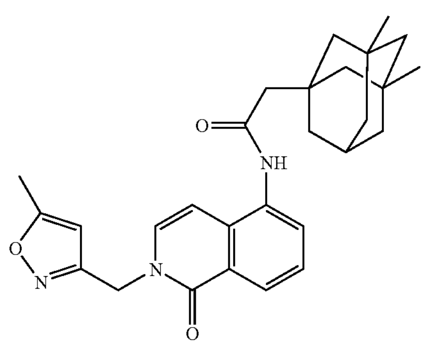 | 459.59 | 460.42 | B1 | | *** |
| 762 | 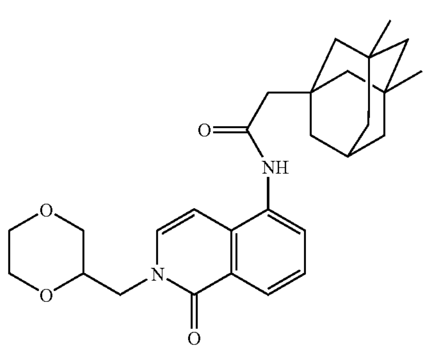 | 464.60 | 465.29 | B1 | | *** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 763 | 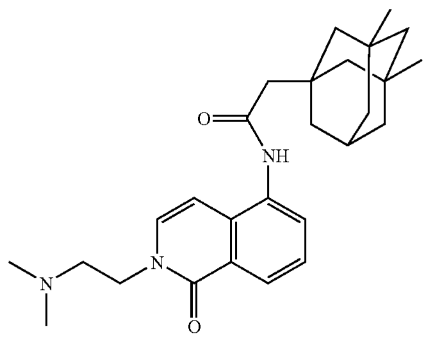 | 435.61 | 436.34 | B1 | | ** |
| 764 | 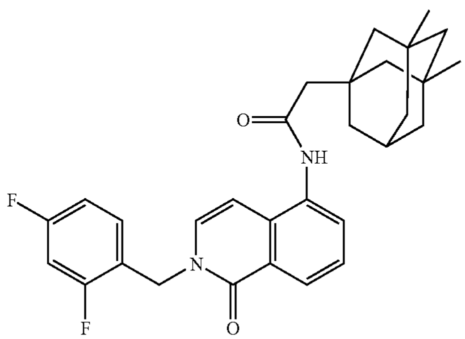 | 490.59 | 491.39 | B1 | | **** |
| 765 | 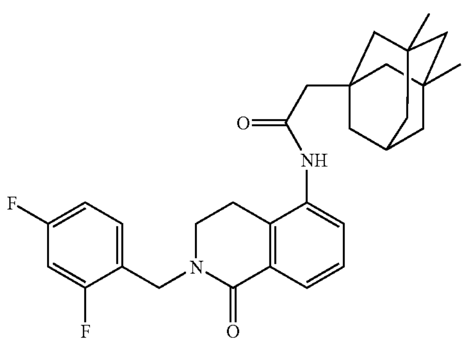 | 492.61 | 493.23 | C | | ** |
| 766 | 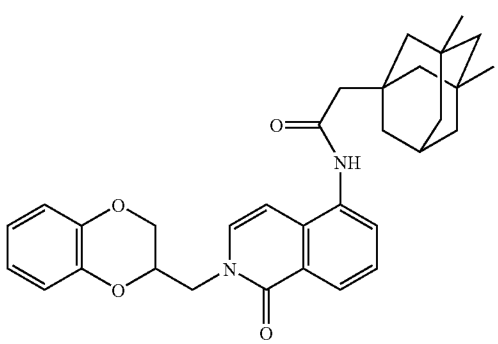 | 512.65 | 513.52 | B1 | | *** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 767 | 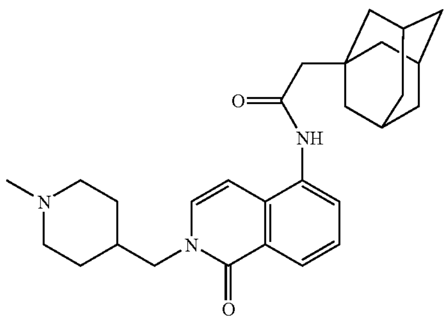 | 447.62 | 448.22 | Modified B1, see comments column | Similar to B1, reaction temperature was 140° C., reaction time 70 h | **** |
| 768 | 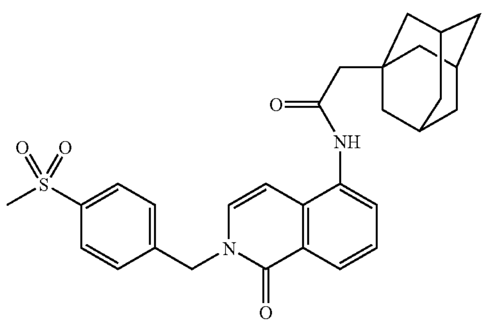 | 504.65 | 505.01 | Modified B1, see comments column | Similar to B1, reaction temperature was 140° C., reaction time 70 h | *** |
| 769 | 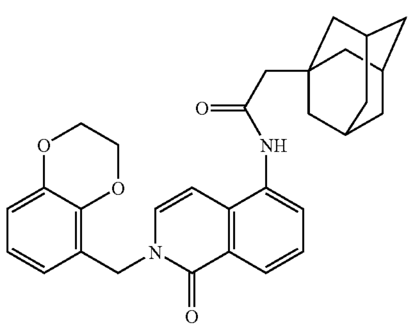 | 484.59 | 485.20 | Modified B1, see comments column | Similar to B1, reaction temperature was 140° C., reaction time 70 h | **** |
| 770 | 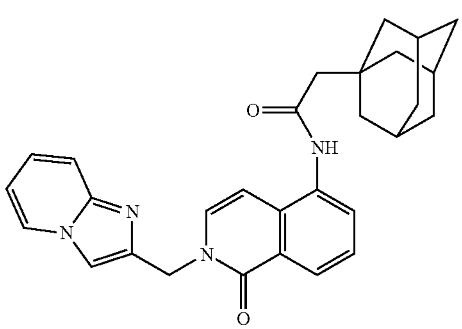 | 466.58 | 467.17 | Modified B1, see comments column | Similar to B1, reaction temperature was 140° C., reaction time 70 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 771 | Chiral | 420.55 | 421.13 | Modified B1, see comments column | Similar to B1, reaction temperature was 140° C., reaction time 70 h | **** |
| 772 | 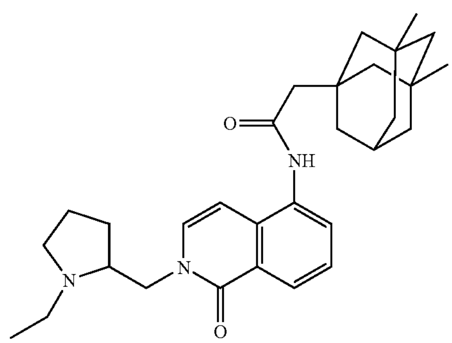 | 475.67 | 476.33 | B1 | | *** |
| 773 | 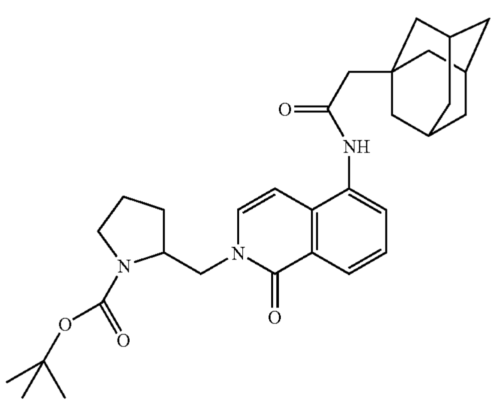 | 519.68 | 520.34 | Modified B1, see comments column | Similar to B1, reaction temperature was 140° C., reaction time 70 h | **** |
| 774 | Chiral | 519.68 | 520.34 | Modified B1, see comments column | Similar to B1, reaction temperature was 140° C., reaction time 70 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 775 | Chiral | 519.68 | 520.34 | Modified B1, see comments column | Similar to B1, reaction temperature was 140° C., reaction time 70 h | **** |
| 776 | Chiral | 483.61 | 484.15 | Modified B1, see comments column | Similar to B1, reaction temperature was 140° C., reaction time 70 h | *** |
| 777 | 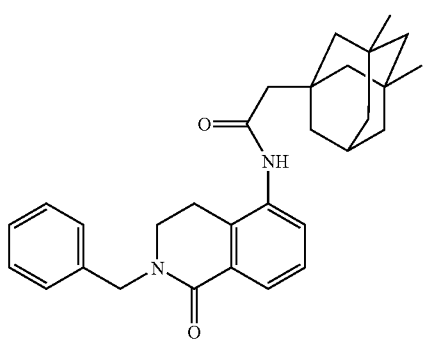 | 456.63 | 457.18 | C |  | **** |
| 778 | 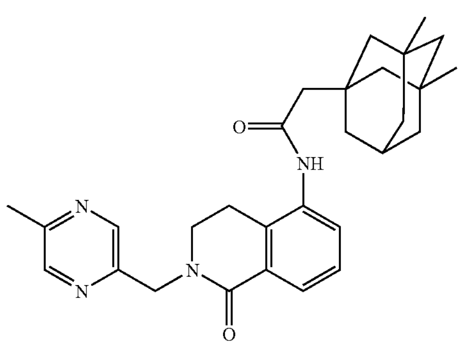 | 472.63 | 473.25 | C |  | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 779 | 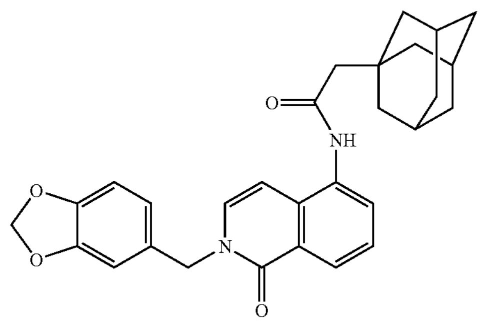 | 470.57 | 471.15 | Modified B1, see comments column | Similar to B1, reaction temperature was 140° C., reaction time 70 h | **** |
| 780 | 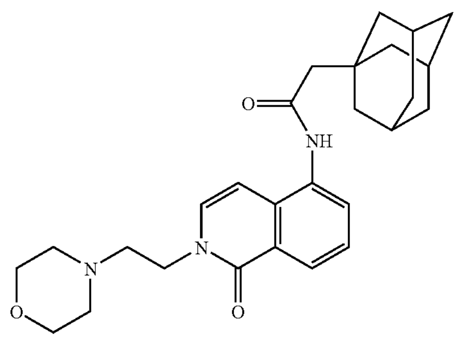 | 449.59 | 450.13 | Method B1 or Modified B1 | Similar to B1, reaction temperature was 140° C., reaction time 70 h | **** |
| 781 | 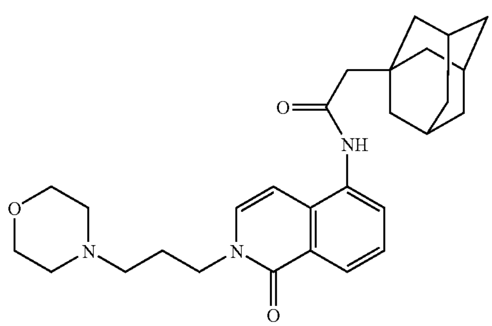 | 463.62 | 464.24 | Method B1 or Modified B1 | Similar to B1, reaction temperature was 140° C., reaction time 70 h | **** |
| 782 | 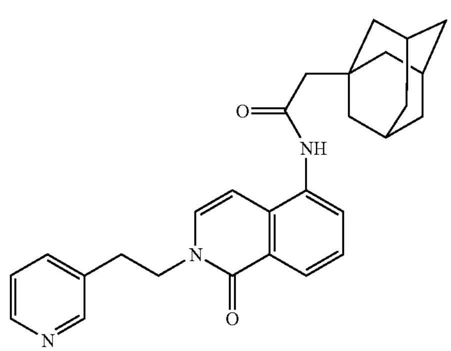 | 441.57 | 442.17 | Modified B1, see comments column | Similar to B1, reaction temperature was 140° C., reaction time 70 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 783 | 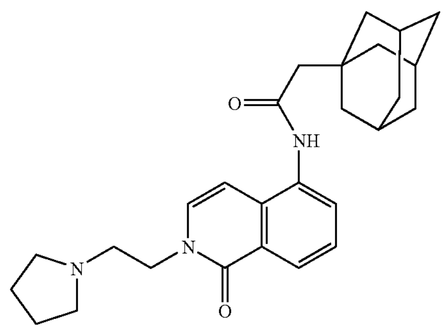 | 433.59 | 434.42 | Modified B1, see comments column | Similar to B1, reaction temperature was 140° C., reaction time 70 h | **** |
| 784 | 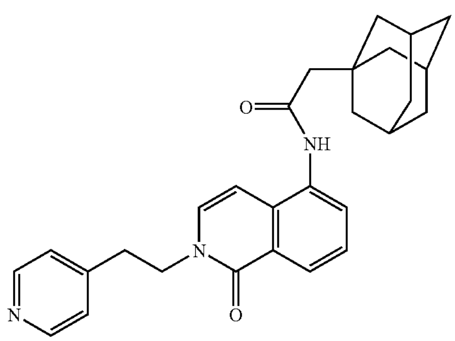 | 441.57 | 442.18 | Modified B1, see comments column | Similar to B1, reaction temperature was 140° C., reaction time 70 h | **** |
| 785 | 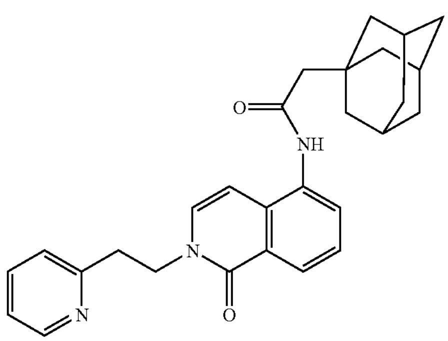 | 441.57 | 442.18 | Modified B1, see comments column | Similar to B1, reaction temperature was 140° C., reaction time 70 h | *** |
| 786 | 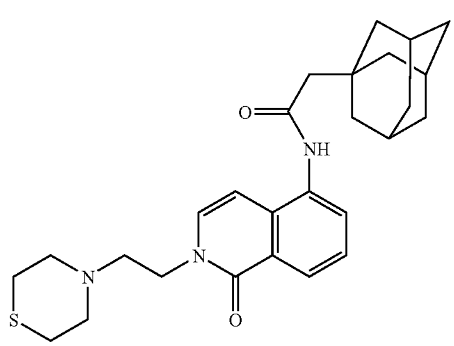 | 465.66 | 466.32 | B1 | Similar to B1, reaction temperature was 140° C., reaction time 70 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 787 | 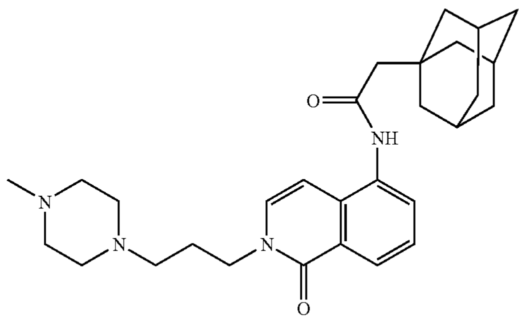 | 476.66 | 477.15 | Modified B1, see comments column | Similar to B1, reaction temperature was 140° C., reaction time 70 h | **** |
| 788 | 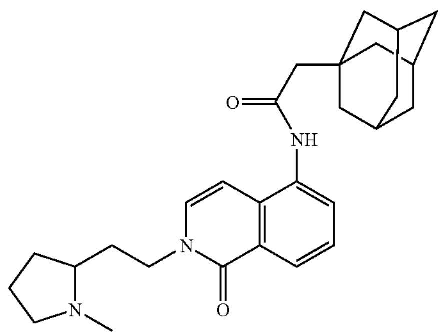 | 447.62 | 448.23 | Modified B1, see comments column | Similar to B1, reaction temperature was 140° C., reaction time 70 h | **** |
| 789 | 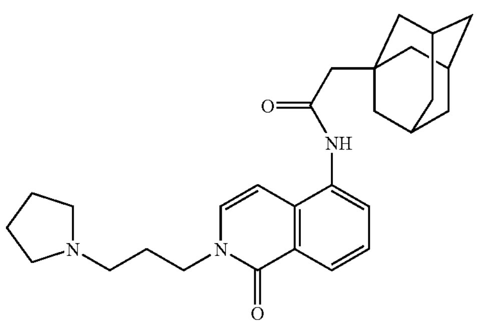 | 447.62 | 448.22 | Modified B1, see comments column | Similar to B1, reaction temperature was 140° C., reaction time 70 h | **** |
| 790 | 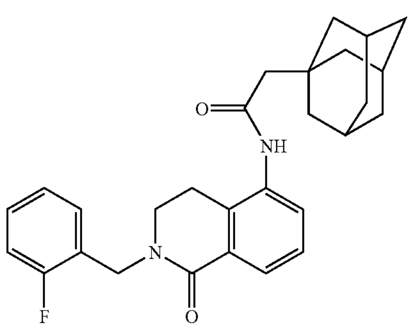 | 446.56 | 447.17 | B1 | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 791 | 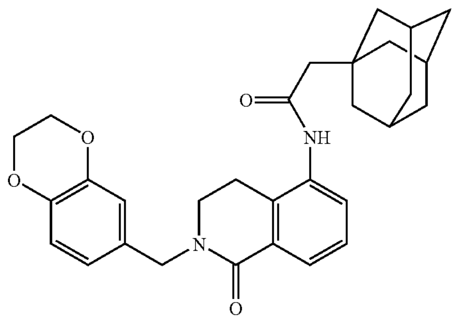 | 486.61 | 487.23 | D | | **** |
| 792 | 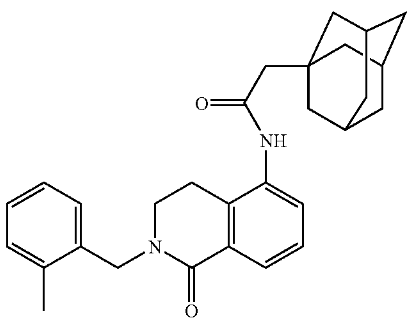 | 442.60 | 443.18 | | | **** |
| 793 | 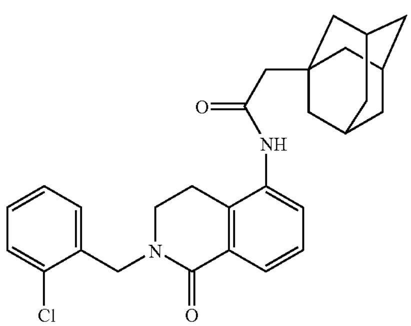 | 463.02 | 463.21 | | | **** |
| 794 | 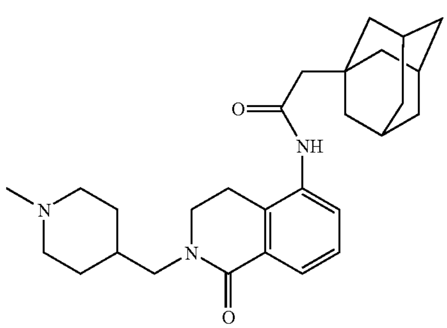 | 449.64 | 450.14 | D | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 795 | 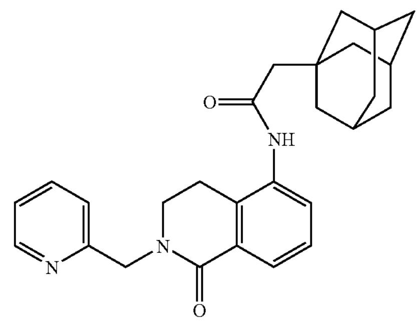 | 429.56 | 430.07 | D | | **** |
| 796 | 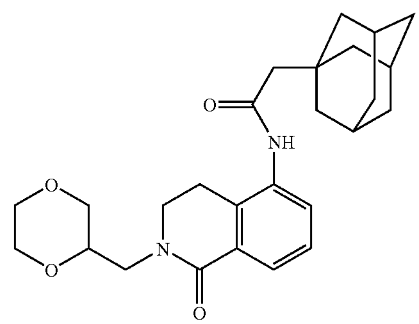 | 438.56 | 439.31 | D | | **** |
| 797 | 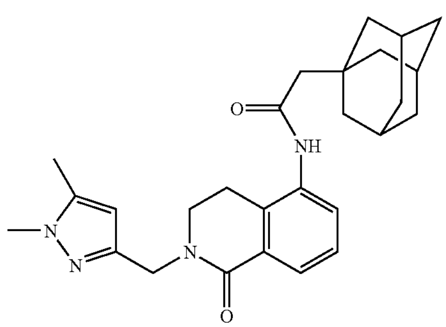 | 446.59 | 447.21 | D | | **** |
| 798 | 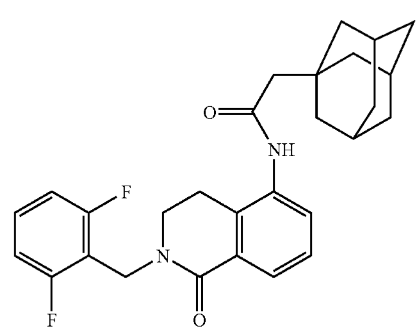 | 464.55 | 465.26 | D | | **** |

TABLE 1-continued
Amide Compounds
| ID | Structure | MW (calcd) | MS (obs) | Synthetic Method | Synthetic Method Comments | IL-1β % Inhibition |
|---|---|---|---|---|---|---|
| 799 | 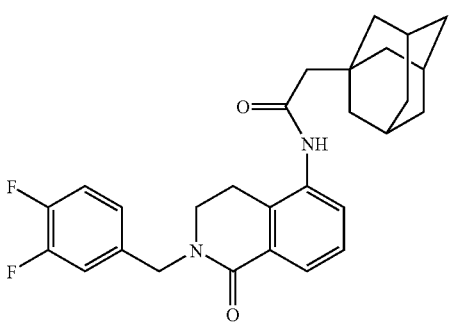 | 464.55 | 465.26 | D | | **** |
| 800 | 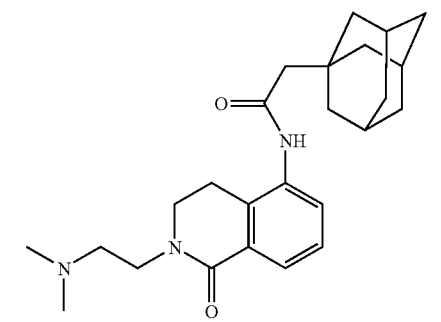 | 409.57 | 410.32 | D | | *** |
| 801 | 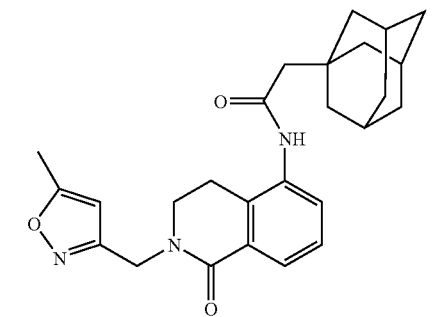 | 433.55 | 434.20 | D | | **** |
| 802 | 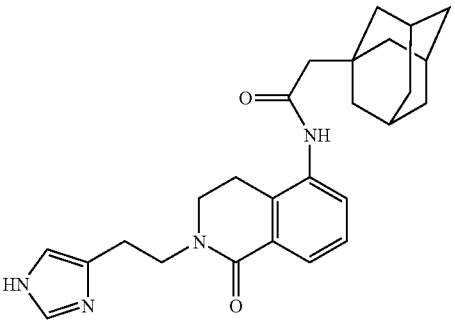 | 432.56 | 433.20 | D | | **** |

TABLE 1-continued
Amide Compounds
| ID | Structure | MW (calcd) | MS (obs) | Synthetic Method | Synthetic Method Comments | IL-1β % Inhibition |
|---|---|---|---|---|---|---|
| 803 | 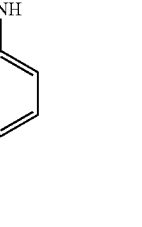 | 512.65 | 513.27 | B1 | | **** |
| 804 | 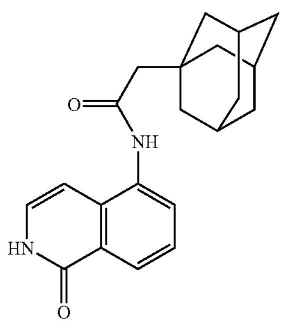 | 336.43 | 337.25 | E | | **** |
| 805 | 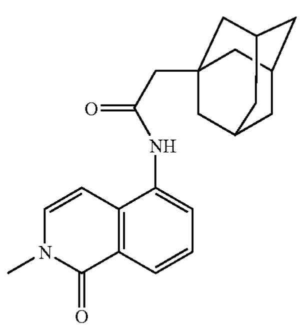 | 350.46 | 351.29 | F | | **** |
| 806 | 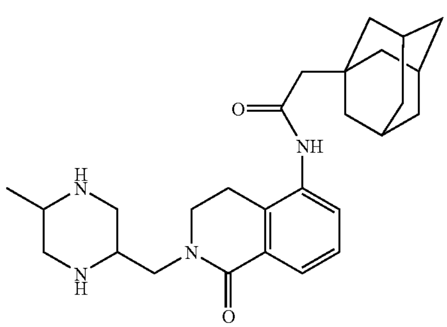 | 450.62 | 451.07 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 807 | 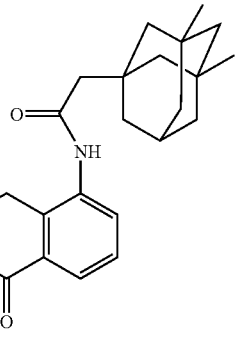 | 457.61 | 458.18 | D | | * |
| 808 | 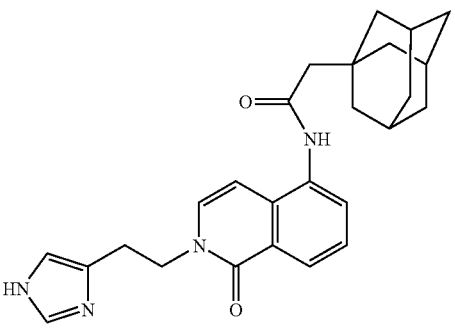 | 430.55 | 431.21 | Modified B1, see comments column | Similar to B1, reaction temperature was 140° C., reaction time 70 h | **** |
| 809 | 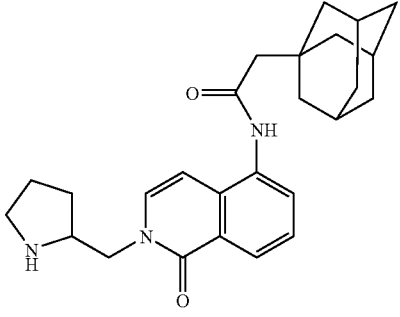 | 419.57 | 420.21 | Modified B1, see comments column | Similar to B1, reaction temperature was 140° C., reaction time 70 h | **** |
| 810 | 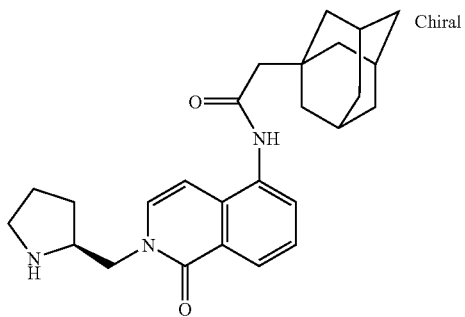 | 419.57 | 420.21 | Modified B1, see comments column | Similar to B1, reaction temperature was 140° C., reaction time 70 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 811 | 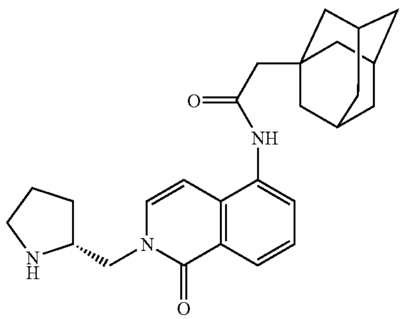 | 419.57 | 420.20 | Modified B1, see comments column | Similar to B1, reaction temperature was 140° C., reaction time 70 h | **** |
| 812 | 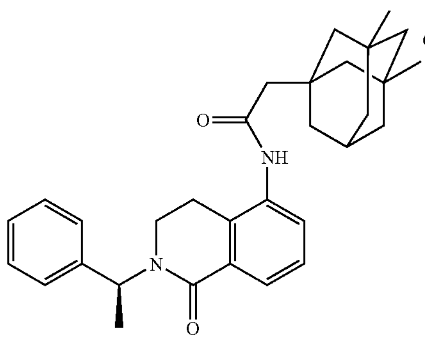 | 470.65 | 471.41 | C | | *** |
| 813 | 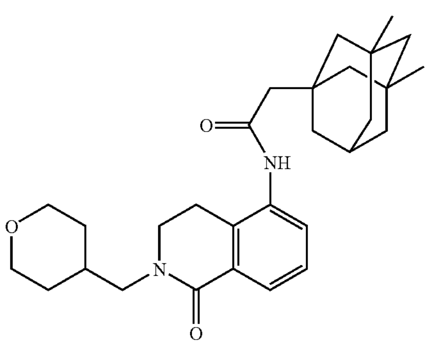 | 464.65 | 465.19 | C | | **** |
| 814 | 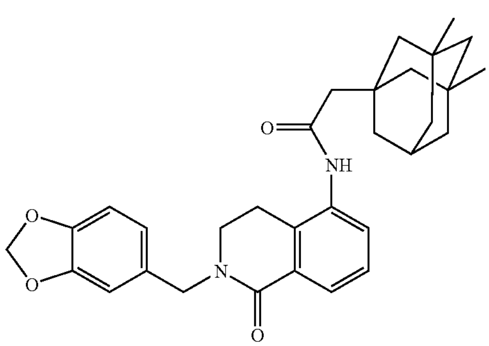 | 500.64 | 501.20 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 815 | 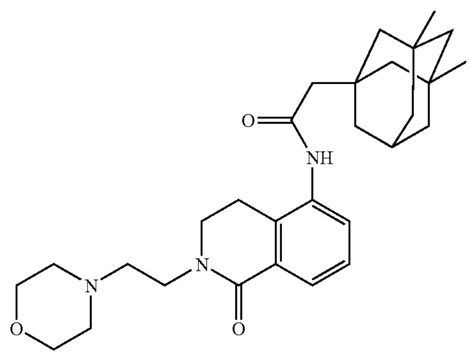 | 479.66 | 480.12 | C | | *** |
| 816 | 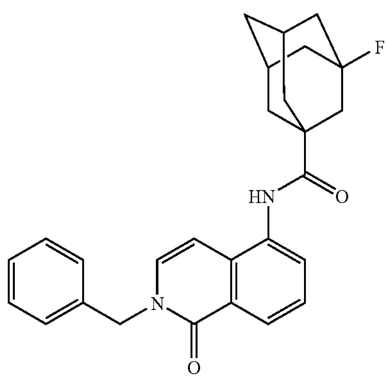 | 430.52 | 431.13 | I | | ** |
| 817 | 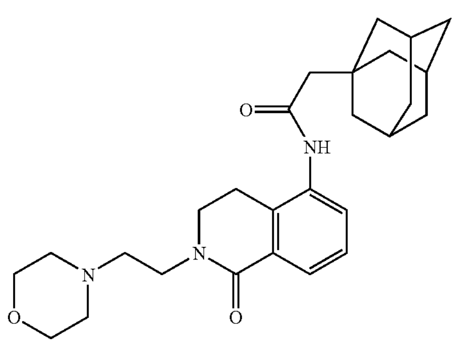 | 451.61 | 452.00 | B2 or Modified B2 | Reaction temperature 165° C., reaction time 48 h | **** |
| 818 | 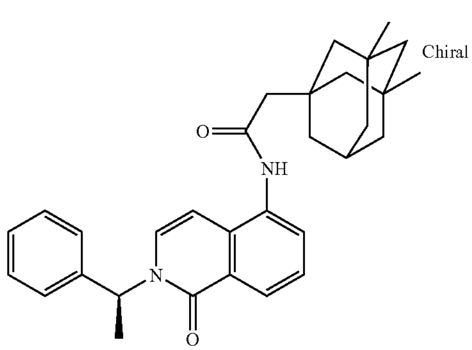 | 468.64 | 469.43 | B1 | | *** |

TABLE 1-continued
Amide Compounds
| ID | Structure | MW (calcd) | MS (obs) | Synthetic Method | Synthetic Method Comments | IL-1β % Inhibition |
|---|---|---|---|---|---|---|
| 819 | 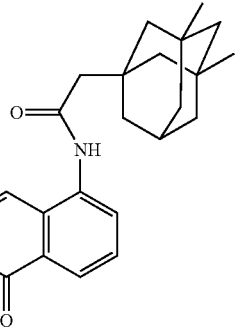 | 490.59 | 491.35 | B1 | | *** |
| 820 | 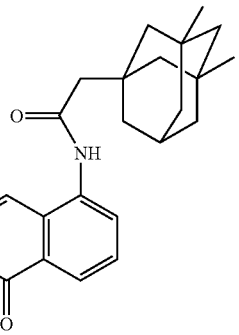 | 462.63 | 463.33 | B1 | | **** |
| 821 | 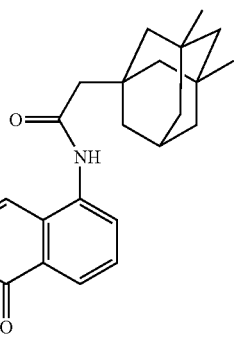 | 498.62 | 499.46 | B1 | | **** |
| 822 | 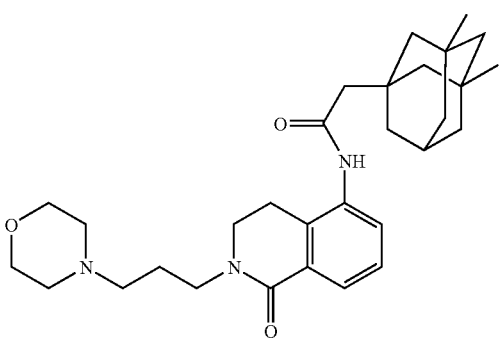 | 493.69 | 492.22 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 823 | 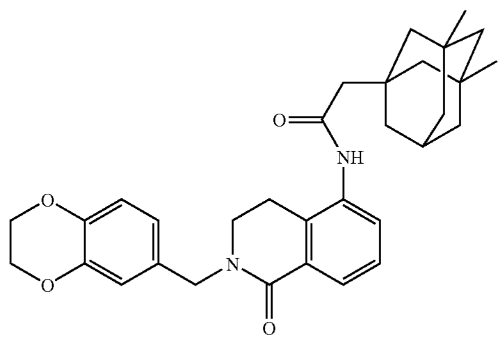 | 514.66 | 513.47 | C | | **** |
| 824 | 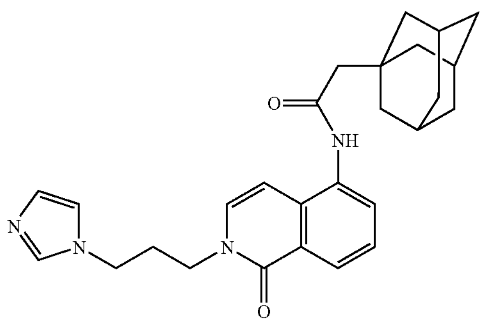 | 444.58 | 445.50 | B1 | | *** |
| 825 | 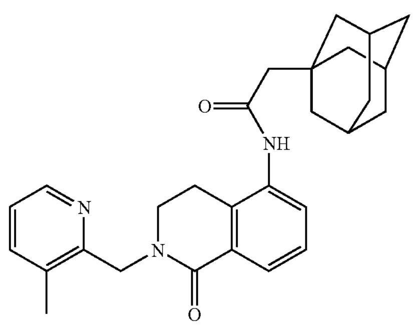 | 443.59 | 442.37 | B1 | | **** |
| 826 | 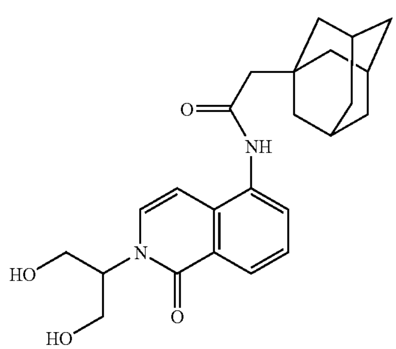 | 410.51 | 411.31 | L | | **** |

TABLE 1-continued

Amide Compounds

| ID | Structure | MW (calcd) | MS (obs) | Synthetic Method | Synthetic Method Comments | IL-1β % Inhibition |
| --- | --- | --- | --- | --- | --- | --- |
| 827 | 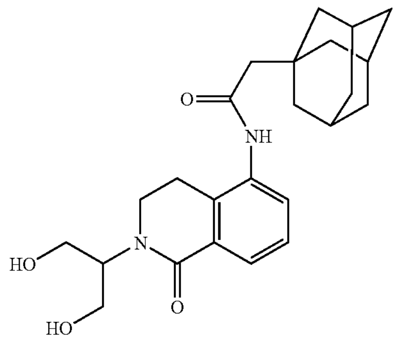 | 412.53 | 413.18 | M | | **** |
| 828 | 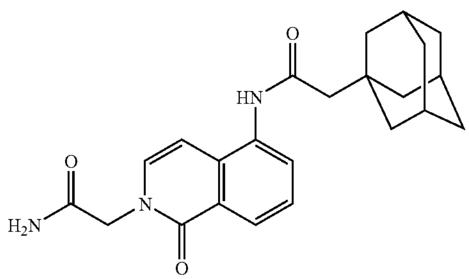 | 393.48 | 394.20 | Modified B1 See comment column | Pyrone (0.089 mmol) + Amine hydrochloride (0.533 mmol), NMM (0.176 mL, 1.16 mmol), 140° C., 96 h | **** |
| 829 | 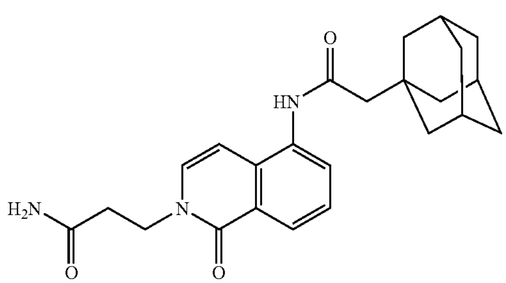 | 407.51 | 408.37 | Other see Comment Column | Pyrone (0.089 mmol) + Amine hydrochloride (0.533 mmol), NMM (0.176 mL, 1.16 mmol), 140° C., 96 h | **** |
| 830 | 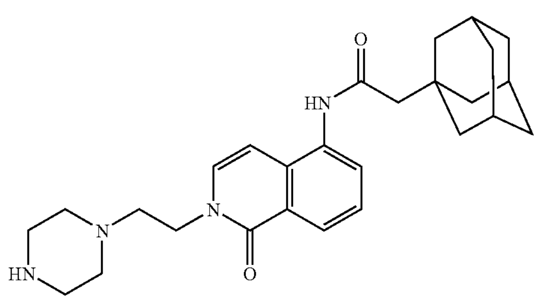 | 448.61 | 449.29 | B1 | | **** |
| 831 | 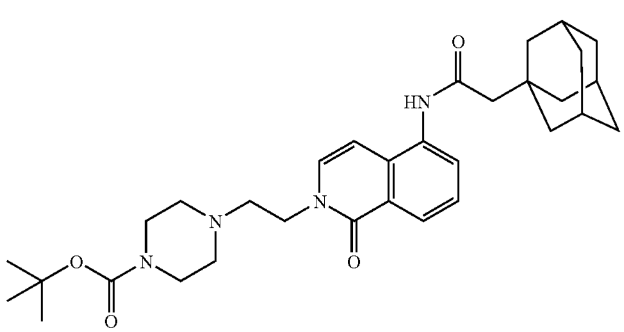 | 548.72 | 549.07 | Modified B1, see comments column | Reaction temperature 145° C. 24-72 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 832 | 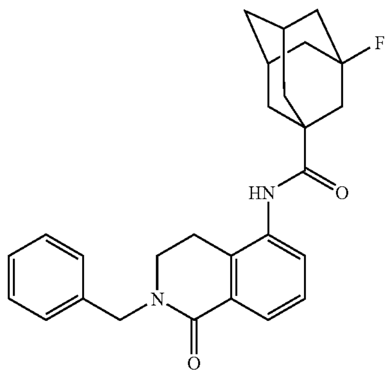 | 432.54 | 433.41 | I, and followed by A2 | | ** |
| 833 | 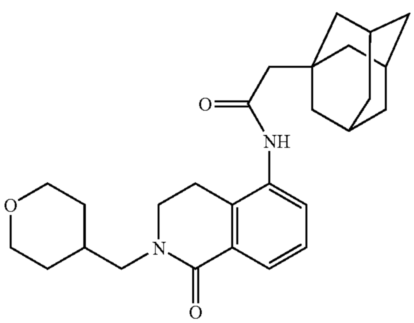 | 436.59 | 437.20 | A2 | 7 days | **** |
| 834 | 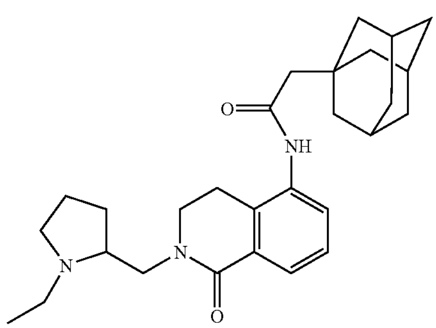 | 449.64 | 450.14 | Other see Comment Column | H2(gas), Pd/C, acetic acid, room temperature, 48 h | **** |
| 835 | 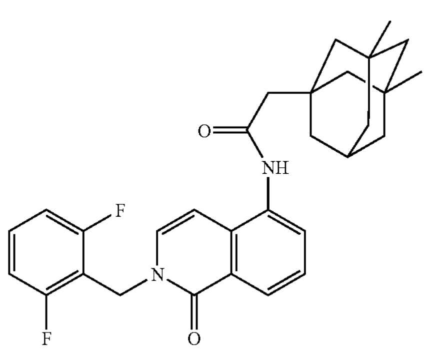 | 490.59 | 491.34 | B1 | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 836 | 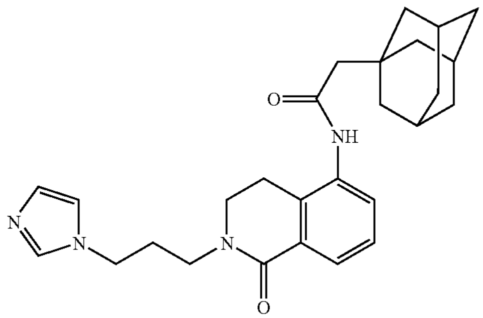 | 446.59 | 447.20 | Other see Comment Column | H2(gas), Pd/C, acetic acid, room temperature, 72 h | **** |
| 837 | 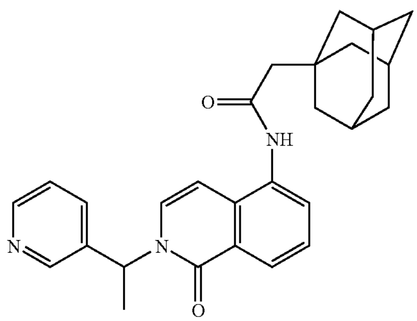 | 441.57 | 442.11 | Modified B1, see comments column | Reaction temperature 145° C. 24-72 h | **** |
| 838 | 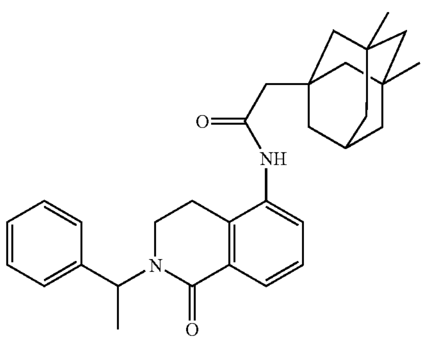 | 470.65 | 471.39 | C | | **** |
| 839 | 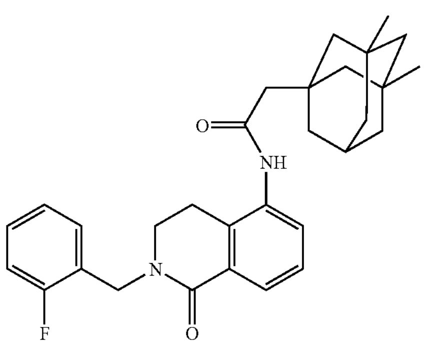 | 474.62 | 475.18 | C | | *** |

TABLE 1-continued
Amide Compounds
| ID | Structure | MW (calcd) | MS (obs) | Synthetic Method | Synthetic Method Comments | IL-1β % Inhibition |
|---|---|---|---|---|---|---|
| 840 | 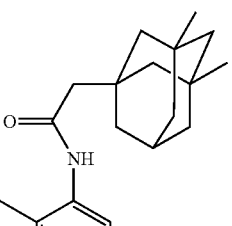 | 492.61 | 493.29 | C | | **** |
| 841 | 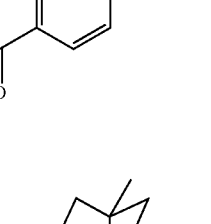 | 364.49 | 365.40 | B1 | | **** |
| 842 | 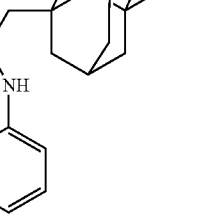 | 462.63 | 463.24 | Modified B1, see comments column | Reaction temperature 145° C. 24-72 h | **** |
| 843 | 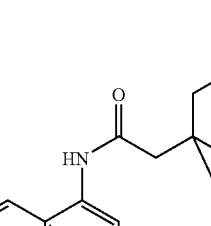 | 477.65 | 478.05 | Modified B1, see comments column | Reaction temperature 145° C. 24-72 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 845 | 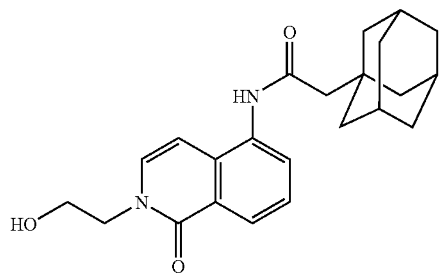 | 380.49 | 381.00 | L | Intermediate 6 (100 mg), ethanolamine (2 mL) | **** |
| 857 | 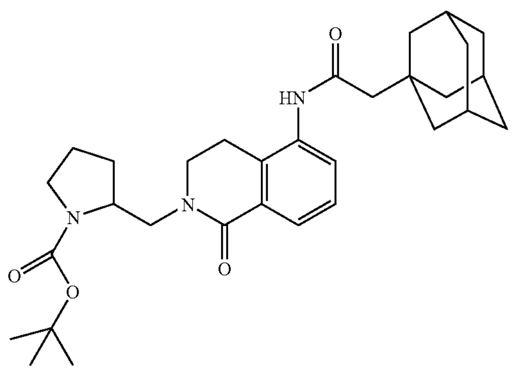 | 521.70 | 522.34 | A2 | 7 day reaction time | **** |
| 858 | 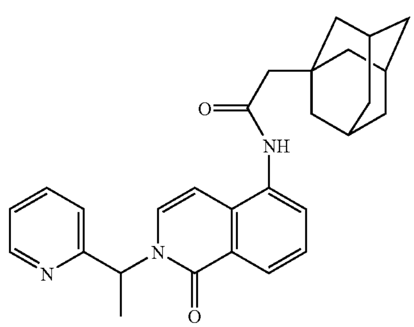 | 441.57 | 442.09 | Modified B1, see comments column | Reaction temperature 145° C. 24-72 h | **** |
| 859 | 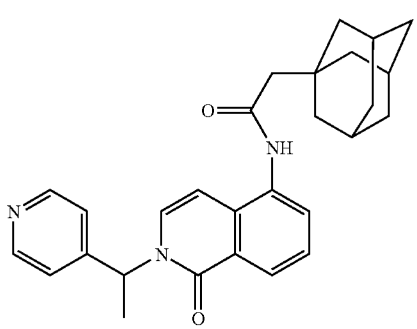 | 441.57 | 442.10 | Modified B1, see comments column | Reaction temperature 145° C. 24-72 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 869 | 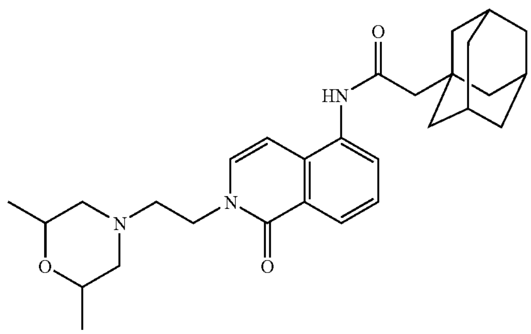 | 477.65 | 477.90 | K | | *** |
| 870 | 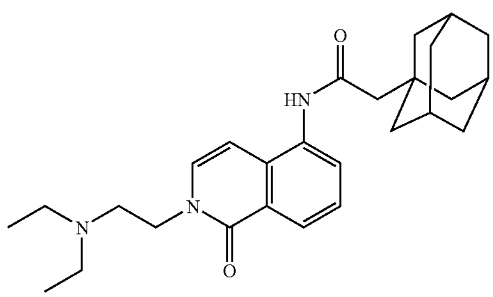 | 435.61 | 435.60 | K | | **** |
| 871 | 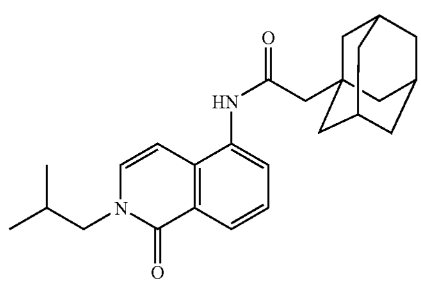 | 392.54 | 393.00 | K | | **** |
| 872 | 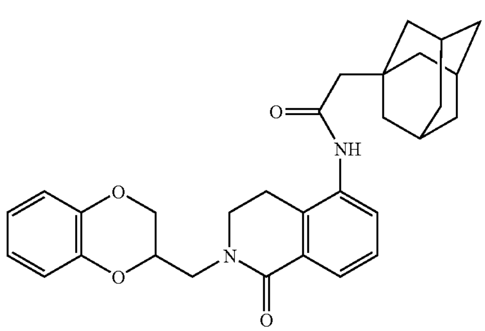 | 486.61 | 487.26 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 873 | 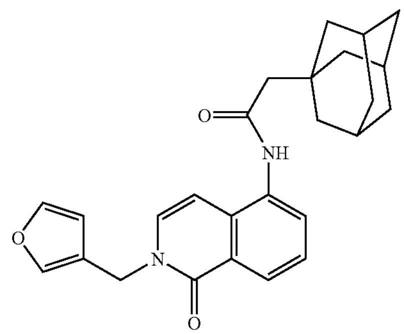 | 416.52 | 417.14 | Other see Comment Column | Pyrone (0.178 mmol) + Amine hydrochloride (0.89 mmol), NMM (0.352 mL, 3.2 mmol), 145° C., 72 h | **** |
| 874 | 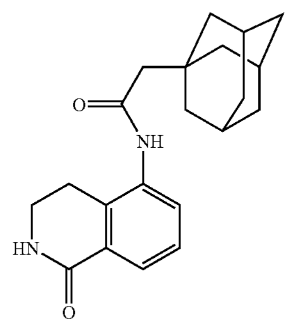 | 338.45 | 339.20 | A2 | | **** |
| 875 | 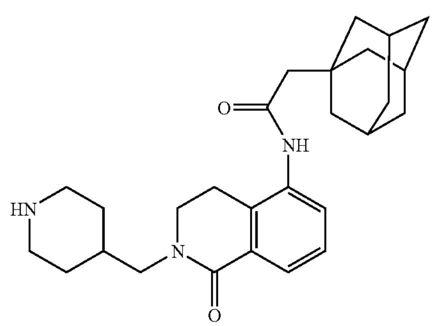 | 435.61 | 436.31 | C | | **** |
| 876 | 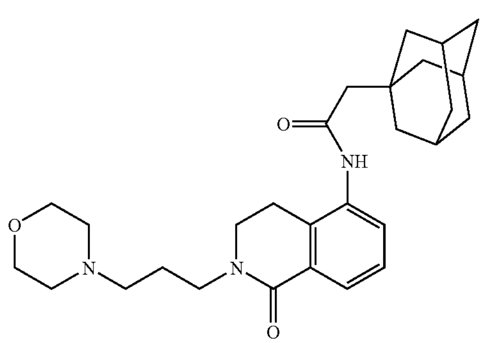 | 465.63 | 466.32 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 878 | 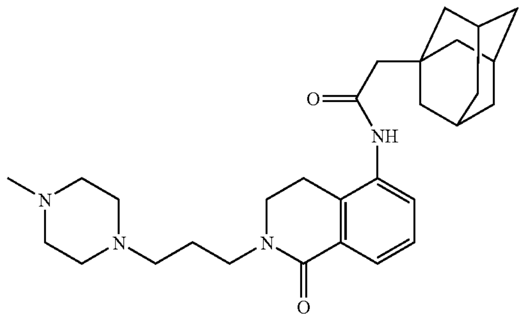 | 478.68 | 479.03 | C | | **** |
| 879 | 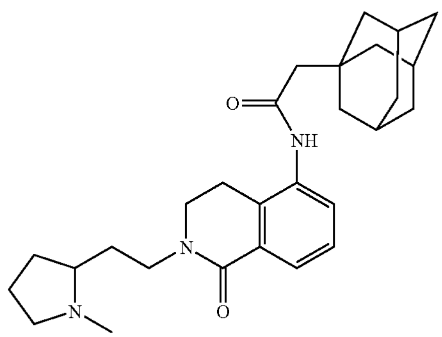 | 449.64 | 450.14 | C | | **** |
| 880 | 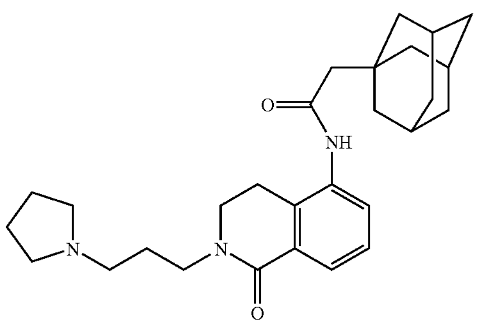 | 449.64 | 450.08 | C | | **** |
| 881 | Chiral | 489.66 | 490.31 | Other see Comment Column | Pyrone (0.178 mmol) + Amine hydrochloride (0.89 mmol), NMM (0.352 mL, 3.2 mmol), 145° C., 72 h | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 882 | Chiral | 473.57 | 474.12 | Modified B1 See comment column | Pyrone (0.178 mmol) + Amine hydrochloride (0.89 mmol), NMM (0.352 mL, 3.2 mmol), 145° C., 72 h | **** |
| 883 | Chiral | 460.57 | 461.33 | Modified B1 See comment column | Pyrone (0.178 mmol) + Amine hydrochloride (0.89 mmol), NMM (0.352 mL, 3.2 mmol), 145° C., 72 h | **** |
| 885 | 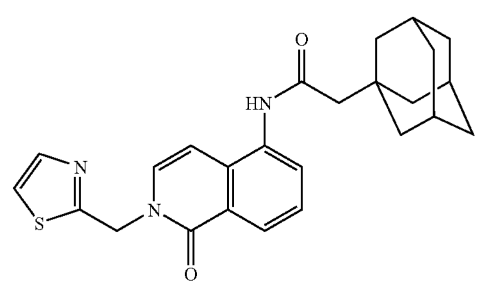 | 433.57 | 434.28 | Other see Comment Column | Pyrone (0.178 mmol) + Amine hydrochloride (0.89 mmol), NMM (0.352 mL, 3.2 mmol), 145° C., 72 h | **** |
| 886 | 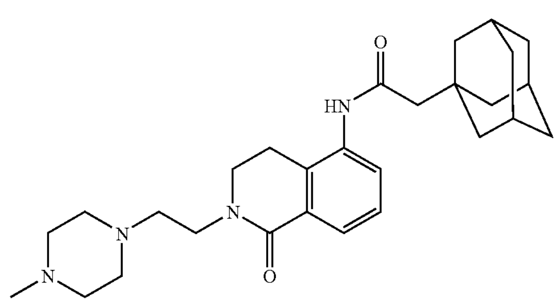 | 464.65 | 465.36 | C | | **** |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 887 | 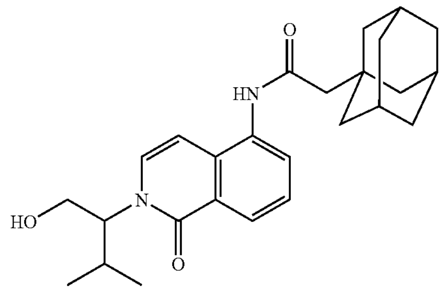 | 422.57 | 423.50 | B1 | | **** |
| 888 | 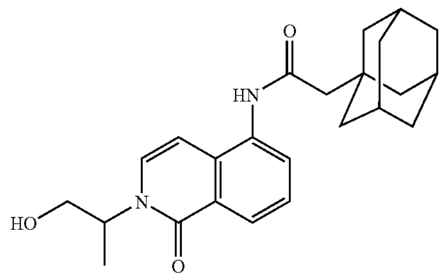 | 394.51 | 395.10 | A1 | | ++++ |
| 890 | 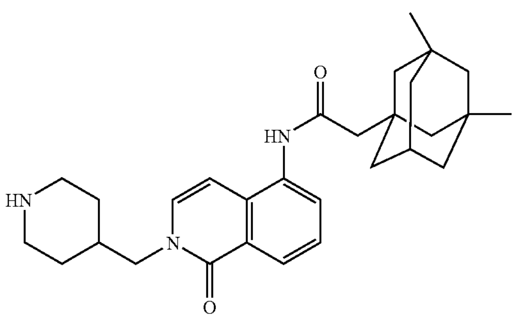 | 461.65 | 461.80 | N | | ++++ |
| 891 | 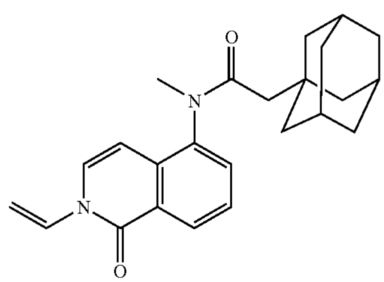 | 376.50 | 377.20 | O | | +++ |
| 892 | 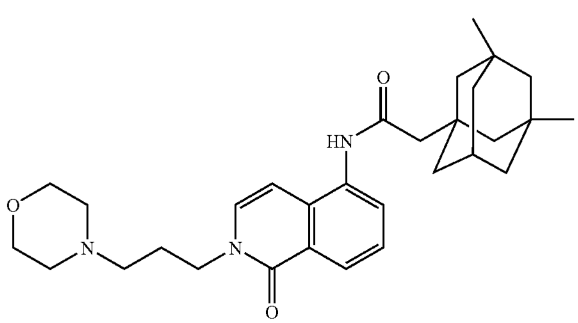 | 491.67 | 491.60 | A2 | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 893 | 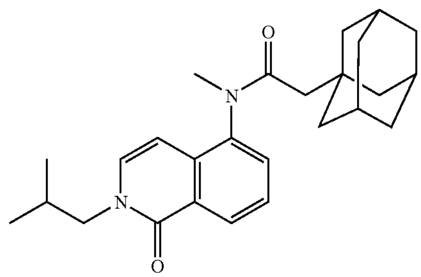 | 406.57 | 407.30 | P | | ++ |
| 894 | 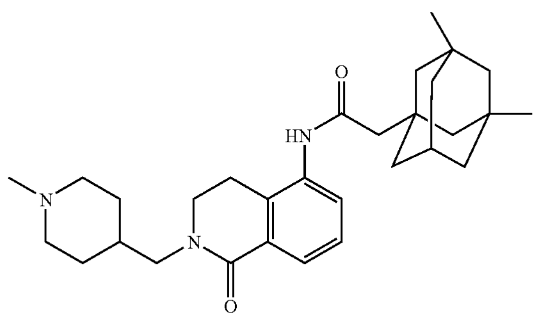 | 477.69 | 477.80 | Q | | ++++ |
| 895 | 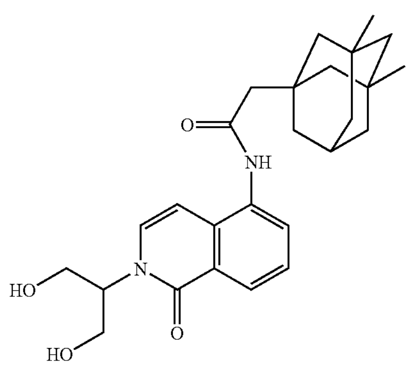 | 438.56 | 439.27 | B1 | | ++++ |
| 896 | 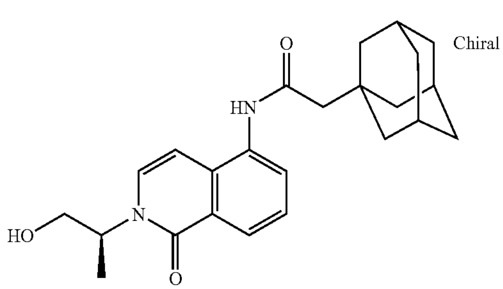 | 394.51 | 395.4 | B | | ++++ |

TABLE 1-continued

Amide Compounds

| ID | Structure | MW (calcd) | MS (obs) | Synthetic Method | Synthetic Method Comments | IL-1β % Inhibition |
|---|---|---|---|---|---|---|
| 897 | (Chiral structure) | 394.51 | 395.2 | B | | ++++ |

"+" compound exhibited 0-25% inhibition at 0.3 μM
"++" compound exhibited 25-50% inhibition at 0.3 μM
"+++" compound exhibited 50-75% inhibition at 0.3 μM
"++++" compound exhibited 75% or greater inhibition at 0.3 μM
"*" compound exhibited 0-25% inhibition at 0.1 μM
"**" compound exhibited 25-50% inhibition at 0.1 μM
"***" compound exhibited 50-75% inhibition at 0.1 μM
"****" compound exhibited 75% or greater inhibition at 0.1 μM
Compounds with a percent inhibition represented by "++++" or "****" are of particular interest.

TABLE 2

NMR for Exemplary Compounds of the Invention

| ID | NMR |
|---|---|
| 701 | (d6-DMSO) δ 9.68(s, 1H), 8.07(d, 1H), 7.87-7.84(m, 1H), 7.64(d, 1H), 7.48(t, 1H), 7.36-7.25(m, 5H), 6.72(d, 1H), 5.19(s, 2H), 2.18(s, 2H), 1.95(s, 3H), 1.68-1.59(m, 12H). |
| 702 | (CDCl3) δ 8.01(d, 1H), 7.61(d, 1H), 7.39-7.21(m, 6H), 6.93(s, 1H), 4.77(s, 2H), 3.45(t, 2H), 2.81(t, 2H), 2.11(s, 2H), 1.90(brs, 3H), 1.80-1.55(m, 12H). |
| 703 | (CDCl3) δ 8.30(d, 1H), 7.94(d, 1H), 7.47(t, 1H), 7.34-6.95(m, 5H), 6.43(d, 1H), 5.15(s, 2H), 2.20(s, 2H), 2.0(brs, 3H), 1.80-1.55(m, 12H). |
| 704 | (CDCl3) δ 8.0(d, 1H), 7.59(d, 1H), 7.19-6.95(m, 5H), 4.72(s, 2H), 3.44(t, 2H), 2.81(t, 2H), 1.99(s, 3H), 1.85-1.50(m, 12H). |
| 707 | (CDCl3) δ 8.29(d, 1H), 7.96(d, 1H), 7.45(t, 1H), 7.16(brs, 1H), 7.08(d, 1H), 6.80(brs, 3H), 6.40(d, 1H), 5.07(s, 2H), 4.21(s, 4H), 2.19(s, 2H), 2.0(brs, 2H), 1.78-1.58(m, 13H). |
| 719 | (CDCl3) δ 8.29(d, 1H), 7.95(d, 1H), 7.44(t, 1H), 7.26-7.18(m, 2H), 6.40(d, 1H), 6.01(s, 1H), 5.14(s, 2H) 3.73(s, 3H) 2.19(s, 3H), 2.18(s, 2H), 2.0(brs, 3H), 1.79-1.60(m, 12H). |
| 725 | (CDCl3) δ 7.99(d, 1H), 7.59(d, 1H), 7.49-7.24(m, 2H), 6.97(brs, 1H), 6.90-6.60(m, 2H), 4.76(s, 2H), 3.53 (t, 2H), 2.84(t, 2H), 2.12(s, 2H), 1.99(brs, 3H), 1.85-1.50(m, 12H). |
| 734 | (CDCl3) δ 8.24(d, 1H), 8.0(d, 1H), 7.46(t, 1H), 7.22(brs, 1H), 7.10(d, 1H), 6.90-6.80(m, 3H), 6.44(d, 1H), 4.64(brs, 1H), 4.45-4.30(m, 2H), 4.14-3.99(m, 2H), 2.2(s, 2H), 2.0(brs, 3H), 1.65-1.55(m, 12H). |
| 736 | (d6-DMSO) δ 9.66(s, 1H), 8.05(d, 1H), 7.85-7.83(m, 1H), 7.50-7.43(m, 2H), 6.65(d, 1H), 4.04(t, 2H), 2.54(t, 2H), 2.18(s, 8H), 1.96(s, 3H), 1.68-1.60(m, 12H). |
| 737 | (CDCl3) δ 8.28(d, 1H), 7.97(d, 1H), 7.47(t, 1H), 7.16(d, 1H), 6.44(d, 1H), 6.05(s, 1H), 5.19(s, 2H), 2.40(s, 3H), 2.20(s, 2H), 2.0(brs, 3H), 1.80-1.50(m, 12H). |
| 746 | (d6-DMSO) δ 9.65(s, 1H), 8.05(d, 1H), 7.84-7.82(m, 1H), 7.51-7.44(m, 2H), 6.66(d, 1H), 3.85(d, 2H), 2.77-2.74(m, 2H), 2.21(s, 2H), 2.14(s, 3H), 2.04-2.03(m, 1H), 1.80-1.75(m, 2H), 1.50-1.47(m, 4H), 1.36-1.26(m, 10H), 1.19-1.05 |
| 749 | (d6-DMSO) δ 9.65(s, 1H), 8.05(d, 1H), 7.85-7.83(m, 1H), 7.50-7.43(m, 2H), 6.66(d, 1H), 3.82(d, 2H), 3.31(brs, 1H), 2.89(d, 2H), 2.38-2.32(m, 2H), 2.18(s, 2H), 1.96(s, 3H), 1.87-1.83(m, 1H), 1.68-1.60(m, 12H), 1.43(d, 2H), 1.16-1. |
| 791 | (CDCl3) δ 8.0(d, 1H), 7.61(d, 1H), 7.35(t, 1H), 7.0(brs, 1H), 6.82-6.76(m, 3H), 4.65(s, 2H), 4.24(s, 4H), 3.44(t, 2H), 2.80(t, 2H), 2.10(s, 2H), 2.0(brs, 3H), 1.80-1.52(m, 12H). |
| 797 | (CDCl3) δ 8.0(d, 1H), 7.65(d, 1H), 7.32(t, 1H), 6.88(s, 1H), 5.98(s, 1H), 4.68(s, 2H), 3.72(s, 3H), 3.54(t, 2H), 2.81(t, 2H), 2.21(s, 3H), 2.12(s, 2H), 2.0(brs, 3H), 1.80-1.51(m, 12H). |
| 822 | (d6-DMSO) δ 9.43(s, 1H), 7.72-7.70(m, 1H), 7.50-7.47(m, 1H), 7.31(t, 1H), 3.56-3.47(m, 8H), 2.94-2.89(m, 1H), 2.82(t, 2H), 2.35-2.30(m, 5H), 2.12(s, 2H), 2.04-2.02(m, 1H), 1.75-1.71(m, 2H), 1.47(d, 2H), 1.33-1.03(m, 10H), 0.80(s, 1H). |
| 826 | (d6-DMSO) δ 9.65(s, 1H), 8.07(d, 1H), 7.83-7.80(m, 1H), 7.50-7.42(m, 2H), 6.65(d, 1H), 4.96-4.93(m, 1H), 4.89(t, 2H), 3.76-3.71(m, 4H), 2.19(s, 2H), 1.96(s, 3H), 1.69-1.60(m, 12H). |
| 827 | (d6-DMSO) δ 9.45(s, 1H), 7.73-7.71(m, 1H), 7.47-7.45(m, 1H), 7.30(t, 1H), 4.73(brs, 2H), 4.60-4.53(m, 1H), 3.58-3.53(m, 4H), 3.48-3.34(m, 2H), 2.78(t, 2H), 1.95(s, 2H), 1.76(s, 3H), 1.69-1.55(m, 12H). |
| 845 | (d6-DMSO) δ 9.65(s, 1H), 8.06(d, 1H), 7.84(d, 1H), 7.47-7.43(m, 2H), 6.65(d, 1H), 4.88(t, 1H), 4.04-4.00(m, 2H), 3.68(t, 2H), 2.19(s, 2H), 1.96(s, 3H), 1.68-1.60(m, 12H). |
| 869 | (d6-DMSO) δ 9.66(s, 1H), 8.05(d, 1H), 7.86-7.83(m, 1H), 7.52-7.43(m, 2H), 6.66(d, 1H), 4.06(t, 2H), 3.50-3.46(m, 2H), 2.82(d, 2H), 2.57(t, 2H), 2.51-2.49(m, 2H), 2.19(s, 2H), 1.96(s, 3H), 1.68-1.60(m, 12H), 1.03(d, 6H). |
| 870 | (d6-DMSO) δ 9.65(s, 1H), 8.05(d, 1H), 7.85-7.83(m, 1H), 7.49-7.42(m, 2H), 6.65(d, 1H), 3.98(t, 2H), 2.67(t, 2H), 2.51-2.46(m, 4H), 2.19(s, 2H), 1.96(s, 3H), 1.73-1.60(m, 12H), 0.88(t, 6H). |

TABLE 2-continued

NMR for Exemplary Compounds of the Invention

| ID | NMR |
|---|---|
| 871 | (d6-DMSO) δ 9.66(s, 1H), 8.05(d, 1H), 7.86-7.84(m, 1H), 7.50-7.44(m, 2H), 6.67(d, 1H), 3.78(d, 2H), 2.19(s, 2H), 2.13-2.10(m, 1H), 1.96(s, 3H), 1.11-1.07(m, 12H), 0.87(d, 6H). |
| 874 | (CD3OD) δ 7.84(d, 1H), 7.47(d, 1H), 7.35(t, 1H), 4.60(s, 1H), 3.43(t, 2H), 2.88(t, 2H), 2.12(s, 2H), 1.99(brs, 3H), 1.81-1.60(m, 12H). |
| 887 | (d6-DMSO) δ 9.66(s, 1H), 8.06(d, 1H), 7.84-7.82(m, 1H), 7.52(d, 1H), 7.44(t, 1H), 6.68(d, 1H), 4.83(t, 1H), 4.65(brs, 1H), 3.86-3.79(m, 1H), 3.74-3.69(m, 1H), 2.22-2.09(m, 3H), 1.96(s, 3H), 1.68-1.60(m, 12H), 1.04(d, 3H), 0.68(d, 3H) |
| 888 | (d6-DMSO) δ 9.66(s, 1H), 8.07(d, 1H), 7.82(d, 1H), 7.54(d, 1H), 7.45(t, 1H), 6.68(t, 1H), 5.07-5.02(m, 1H), 4.94(t, 1H), 3.70-3.57(m, 2H), 2.19(s, 2H), 1.60(s, 3H), 1.68-1.60(m, 12H), 1.29(d, 3H). |
| 890 | (d6-DMSO) δ 9.66(s, 1H), 8.05(d, 1H), 7.83(d, 1H), 7.50-7.44(m, 2H), 6.65(d, 1H), 3.82(d, 2H), 2.90-2.87(m, 2H), 2.34(t, 2H), 2.21(s, 2H), 2.04(s, 1H), 1.88-1.83(m, 1H), 1.51-1.23(m, 13H), 1.15-1.03(m, 4H), 0.80(s, 6H). |
| 891 | (d6-DMSO) δ 8.28(d, 1H), 7.89(d, 1H), 7.73-7.70(m, 1H), 7.64-7.54(m, 2H), 6.40(d, 1H), 5.58-5.54(m, 1H), 5.09-5.07(m, 1H), 3.15(s, 3H), 2.50(s, 2H), 1.99(s, 3H), 1.84-1.26(m, 12H). |
| 892 | (d6-DMSO) δ 9.66(s, 1H), 8.05(d, 1H), 7.84-7.82(m, 1H), 7.53(d, 1H), 7.46(t, 1H), 6.67(d, 1H), 3.99(t, 2H), 3.54(t, 4H), 2.32-2.27(m, 6H), 2.21(s, 2H), 2.04-2.03(m, 1H), 1.86-1.83(m, 2H), 1.50(s, 2H), 1.36-1.26(m, 8H), 1.15-1.05 |
| 893 | (d6-DMSO) δ 8.25(d, 1H), 7.67-7.65(m, 1H), 7.58-7.46(m, 2H), 6.34-6.29(m, 1H), 3.89-3.84(m, 1H), 3.75-3.70(m, 1H), 3.14(s, 3H), 2.51-2.49(m, 2H). 2.14-2.07(m, 1H), 1.83(s, 3H), 1.74-1.42(m, 12H), 0.89-0.86(m, 6H). |
| 894 | (d6-DMSO) δ 9.48(s, 1H), 7.72(d, 1H), 7.48(d, 1H), 7.32(t, 1H), 3.52(t, 2H), 3.41-3.36(m, 4H), 2.83(t, 2H), 2.72-2.69(m, 3H), 2.13(s, 2H), 2.05-2.00(m, 1H), 1.86(s, 1H), 1.80-1.76(m, 2H), 1.48-1.47(m, 3H), 1.37-1.26(m, 10H), 1.23-1.03(m, 3H)0.80(s, 6H) |
| 895 | (d6-DMSO) δ 9.65(s, 1H), 8.07(d, 1H), 7.49-7.42(m, 2H), 6.64(d, 1H), 4.96-4.87(m, 3H), 3.79-3.69(m, 4H) 2.21(s, 2H), 2.05(s, 1H), 1.51(br s, 2H) 1.39-1.24(m, 8H)1.17-1.03(m, 2H)0.81(s, 6H) |

The following compounds have been or can be prepared according to the methods of the invention. For purposes of Table 3, activity of each compound is expressed as follows:

TABLE 3

Pore Formation Data for Exemplary Compounds of the Invention.

| ID | Pore Formation % inhibition |
|---|---|
| 702 | ++++ |
| 707 | ++++ |
| 709 | ++++ |
| 717 | ++++ |
| 727 | ++++ |
| 751 | *** |
| 780 | **** |
| 804 | ++++ |

"+" compound exhibited 0-25% pore formation inhibition at 0.3 μM
"++" compound exhibited 25-50% pore formation inhibition at 0.3 μM
"+++" compound exhibited 50-75% pore formation inhibition at 0.3 μM
"++++" compound exhibited 75% or greater pore formation inhibition at 0.3 μM
"*" compound exhibited 0-25% pore formation inhibition at 0.1 μM
"**" compound exhibited 25-50% pore formation inhibition at 0.1 μM

TABLE 3-continued

Pore Formation Data for Exemplary Compounds of the Invention.

| ID | Pore Formation % inhibition |
|---|---|

"***" compound exhibited 50-75% pore formation inhibition at 0.1 μM
"****" compound exhibited 75% or greater pore formation inhibition at 0.1 μM
Compounds with a percent inhibition represented by "++++" or "****" are of particular interest.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:
1. A bicycloheteroaryl compound having a formula:

II wherein
A is selected from CO;
B and Y are independently selected from $CR^{2a}$ and $CR^{2a}R^{2b}$;
W, W' and Z are independently selected from $CR^4$;
$L^1$ is a bond or a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy;
n is 0, 1, 2 or 3;
$R^1$ is selected from 3-13 membered cycloalkyl, which can be optionally substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamido;
each of $R^{2a}$, $R^{2b}$, $R^{2'}$ and $R^{2''}$ is independently selected from hydrogen, substituted or unsubstituted $C_1$-$C_6$ alkyl; or any of $R^{2'}$ and $R^{2''}$ can join together to form a cycloalkyl or cycloheteroalkyl ring of 3-7 atoms;
$R^3$ is selected from hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bicycloaryl, and substituted or unsubstituted bicycloheteroaryl; provided that, when $L^1$ is a bond, $R^3$ may be selected from hydrogen, substituted or unsubstituted alkyl, substituted or unsubstituted cycloalkyl, and substituted or unsubstituted heterocycloalkyl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfo, substituted or unsubstituted sulfonyl, substututed or unsubstituted sulfanyl, substituted or unsubstituted aminosulfonyl, substituted or unsubstituted arylsulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;

and the dotted bond is a single or a double bond;

or a pharmaceutically acceptable salt;

and stereoisomers and tautomers thereof.

2. A compound according to claim 1 wherein each of B and Y is $CR^{2a}R^{2b}$; and the dotted bond is a single bond.

3. A compound according to claim 1 wherein each of B and Y is $CH_2$; and the dotted bond is a single bond.

4. A compound according to claim 1 wherein each of B and Y is $CR^{2a}$; and the dotted bond is a double bond.

5. A compound according to claim 1 wherein each of B and Y is CH; and the dotted bond is a double bond.

6. A compound according to claim 1 wherein each of $R^{2'}$ and $R^{2''}$ of the

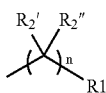

group is H.

7. A compound according to claim 1 wherein one of $R^{2'}$ and $R^{2''}$ of the

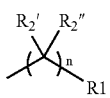

group is Me and the other is H.

8. A compound according to claim 1 wherein each of $R^{2'}$ and $R^{2''}$ of the

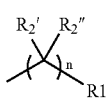

group is Me.

9. A compound according to claim 1 wherein the n of

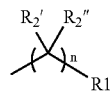

group is 0 and $R^1$ selected from substituted or unsubstituted adamantane.

10. A compound according to claim 1 wherein the n of

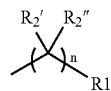

group is 0 or 1; each of $R^{2'}$ and $R^{2''}$ is H; and $R^1$ is

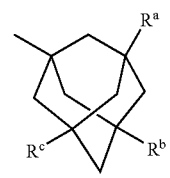

and wherein $R^a$, $R^b$ and $R^c$ are independently selected from H, halo, hydroxyl, substituted hydroxyl, alkyl, substituted alkyl, amino, substituted amino, aryl and substituted aryl.

11. A compound of claim 10 wherein $R^a$, $R^b$ and $R^c$ are independently selected from H, Br, Cl, OH, Me, NHAc, Ph and F.

12. A compound of claim 10 wherein each of $R^a$, $R^b$ and $R^c$ is H.

13. A compound according to claim 1 wherein the compound is depicted by a formula

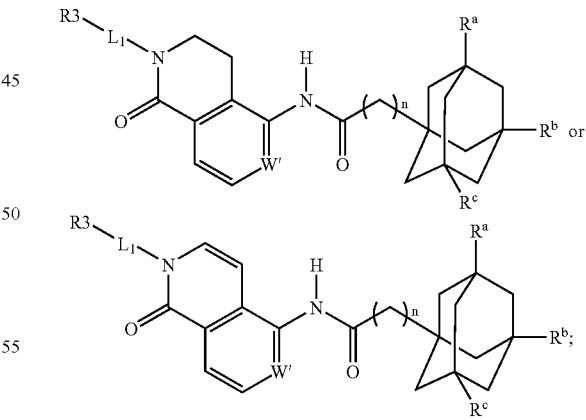

and wherein $L^1$, $R^3$, W' and n are as described in claim 1; and wherein $R^a$, $R^b$ and $R^c$ are independently selected from H, halo, hydroxyl, substituted hydroxyl, alkyl, substituted alkyl, amino, substituted amino, aryl and substituted aryl.

14. A compound according to claim 13 wherein n is 0.

15. A compound according to claim 13 wherein n is 1.

16. A compound according to claim 13 wherein each of $R^a$, $R^b$ and $R^c$ is H.

17. A compound according to claim 13 wherein each of $R^a$, $R^b$ and $R^c$ is Me.

18. A compound according to claim 13 wherein one of $R^a$, $R^b$ and $R^c$ is Me.

19. A compound according to claim 13 wherein two of $R^a$, $R^b$ and $R^c$ is Me.

20. A compound according to either of claim 1 or 13 wherein $L^1$ is a bond and $R^3$ is H.

21. A compound according to either of claim 1 or 13 wherein $L^1$ is a $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy; and $R^3$ is H.

22. A compound according to either of claim 1 or 13 wherein $L^1$ is —$CH_2$—.

23. A compound according to either of claim 1 or 13 wherein $L^1$ is $C_1$-$C_5$ alkylene group which can be optionally substituted by a substituent selected from alkyl, hydroxy, hydroxyalkyl, aminoalkyl, alkylaminoalkyl, dialkylaminoalkyl, halogen, carbamoyl, and $C_1$-$C_6$ alkoxy.

24. A compound according to either of claim 1 or 13 wherein $R^3$ is substituted or unsubstituted alkyl.

25. A compound according to either of claim 1 or 13 wherein $R^3$ is substituted alkyl and the substitution on alkyl is selected from aryl, heteroaryl, cycloalkyl, heterocycloalkyl, halo, alkoxy, hydroxy, cyano, and aryloxy.

26. A compound according to either of claim 1 or 13 wherein $R^3$ is substituted alkyl and the substitution on alkyl is selected from Ph, Cl, F, Br, CN, OH, OMe, OPh, $CF_3$, $CHF_2$, $OCF_3$, t-Bu, SMe, SOMe, $SO_2Me$, $SO_3H$, $SO_3Me$, pyridyl, cyclopropyl, cyclopentyl and cyclohexyl.

27. A compound according to either of claim 1 or 13 wherein $R^3$ is

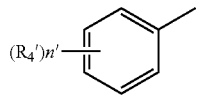

and wherein n' is selected from 1-5 and each of $R^{4'}$ is independently selected from hydrogen, alkyl, substituted alkyl, acyl, substituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfo, substituted or unsubstituted sulfonyl, substituted or unsubstituted sulfanyl, substituted or unsubstituted aminosulfonyl, substituted or unsubstituted arylsulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

28. A compound according to claim 27 wherein n' is 1, 2 or 3.

29. A compound according to claim 27 wherein each $R^{4'}$ is independently selected from Me, Et, Ph, Cl, F, Br, CN, OH, OMe, OPh, COPh, $CF_3$, $CHF_2$, $OCF_3$, t-Bu, SMe, $CH=CH—CO_2H$, SOMe, $SO_2Me$, $SO_3H$, $SO_3Me$, and pyridyl.

30. A compound according to either of claim 1 or 13 wherein $R^3$ is substituted or unsubstituted cycloalkyl, heterocycloalkyl, heteroaryl, bicycloaryl or bicycloheteroaryl.

31. A compound according to either of claim 1 or 13 wherein $R^3$ is substituted or unsubstituted naphthalene, furanyl, thiophenyl, pyrrolyl, pyrazolyl, imidazolyl, triazolyl, pyridyl, pyrimidinyl, quinoline, isoquinolinyl, tetrahydroquinolinyl, tetrahydroisoquinolinyl, indolyl, benzopyranyl, benzofuranyl, benzoxazinyl, or benzodioxanyl.

32. A compound according to claim 1 wherein each of W, and Z is independently $CR^4$.

33. A compound according to claim 1 wherein each of W, and Z is independently CH.

34. A compound according to claims 1 or 13 wherein W' is C-Me.

35. A compound according to either one of claims 1 or 13 wherein W' is CH.

36. A compound according to claim 1 wherein Z is $CR^4$ and W and W' both are CHs.

37. A compound according to claim 1 wherein the compound is selected from

| Name | Structure |
|---|---|
| 2-Adamantan-1-yl-N-(2-benzyl-1-oxo-1,2-dihydro-isoquinolin-5-yl)-acetamide | 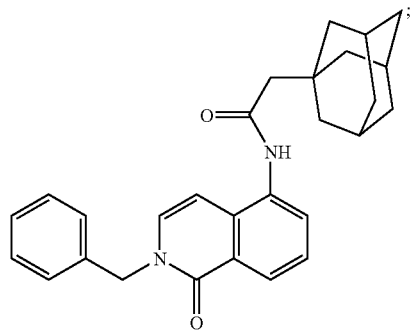 |

-continued
| Name | Structure |
|---|---|
| 2-Adamantan-1-yl-N-(2-benzyl-1-oxo-1,2,3,4-tetrahydro-isoquinolin-5-yl)-acetamide | 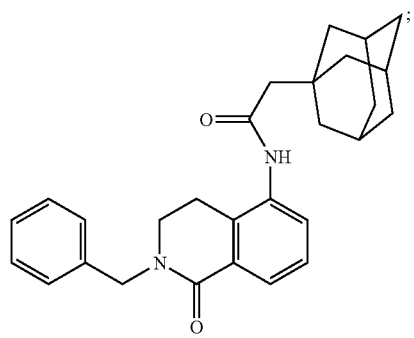 |
| 2-Adamantan-1-yl-N-[2-(4-fluoro-benzyl)-1-oxo-1,2-dihydro-isoquinolin-5-yl]-acetamide | 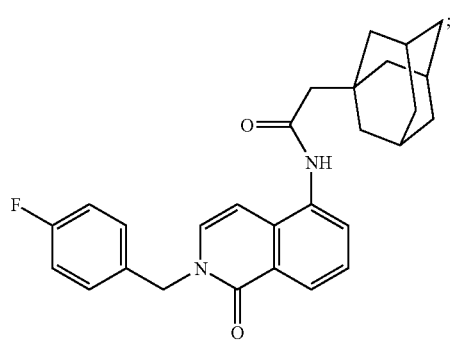 |
| 2-Adamantan-1-yl-N-[2-(4-fluoro-benzyl)-1-oxo-1,2,3,4-tetrahydro-isoquinolin-5-yl]-acetamide | 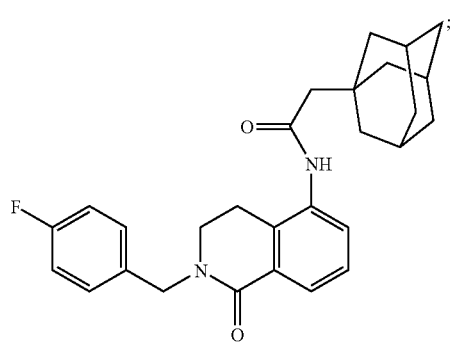 |
| 2-Adamantan-1-yl-N-[2-(2,4-difluoro-benzyl)-1-oxo-1,2-dihydro-isoquinolin-5-yl]-acetamide | 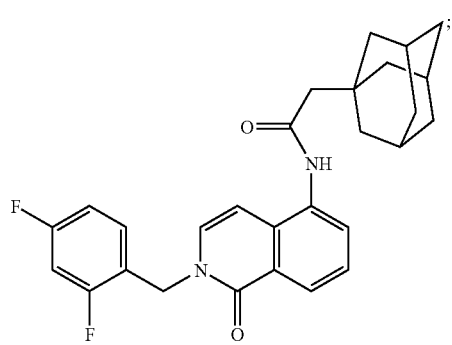 |

| Name | Structure |
|---|---|
| 2-Adamantan-1-yl-N-[2-(2-fluoro-benzyl)-1-oxo-1,2-dihydro-isoquinolin-5-yl]-acetamide | 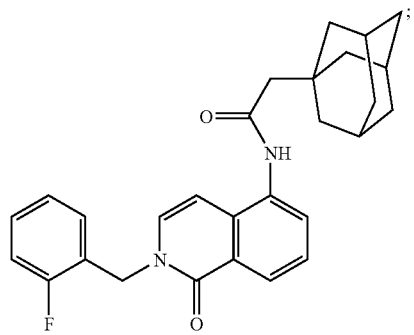 |
| 2-Adamantan-1-yl-N-[2-(2,3-dihydro-benzo[1,4]dioxin-6-ylmethyl)-1-oxo-1,2-dihydro-isoquinolin-5-yl]-acetamide | 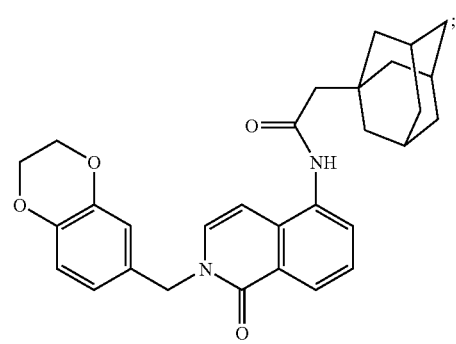 |
| 2-Adamantan-1-yl-N-[2-(2-chloro-benzyl)-1-oxo-1,2-dihydro-isoquinolin-5-yl]-acetamide | 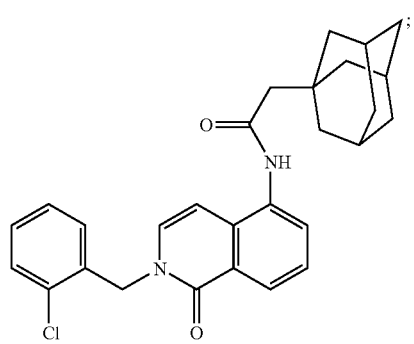 |
| 2-Adamantan-1-yl-N-[1-oxo-2-(tetrahydro-furan-2-ylmethyl)-1,2-dihydro-isoquinolin-5-yl]-acetamide | 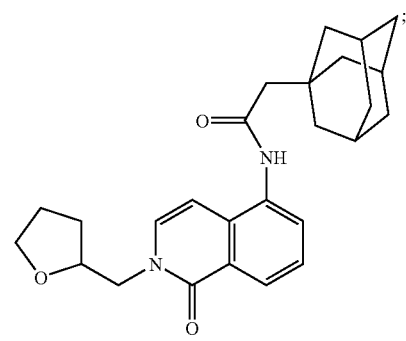 |

-continued
| Name | Structure |
|---|---|
| 2-Adamantan-1-yl-N-[2-(5-methyl-pyrazin-2-ylmethyl)-1-oxo-1,2-dihydro-isoquinolin-5-yl]-acetamide | 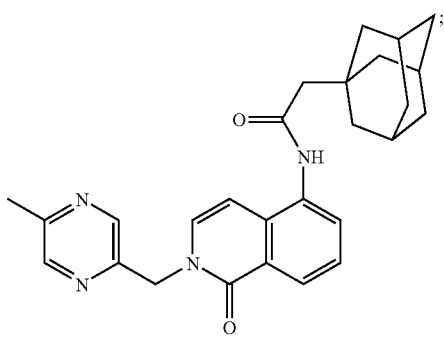 |
| 2-Adamantan-1-yl-N-[1-oxo-2-(1-phenyl-ethyl)-1,2-dihydro-isoquinolin-5-yl] acetamide | 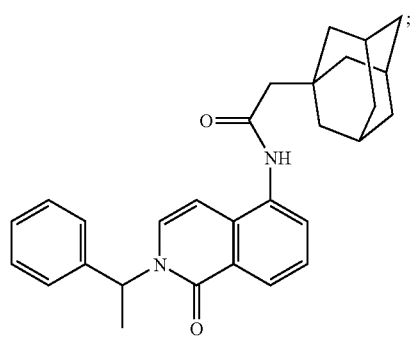 |
| 2-Adamantan-1-yl-N-(2-furan-2-ylmethyl-1-oxo-1,2-dihydro-isoquinolin-5-yl)-acetamide | 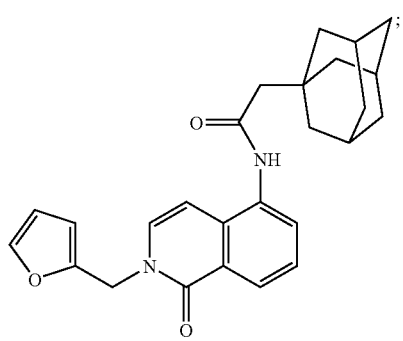 |
| 2-Adamantan-1-yl-N-[1-oxo-2-(4-trifluoromethyl-benzyl)-1,2-dihydro-isoquinolin-5-yl]-acetamide | 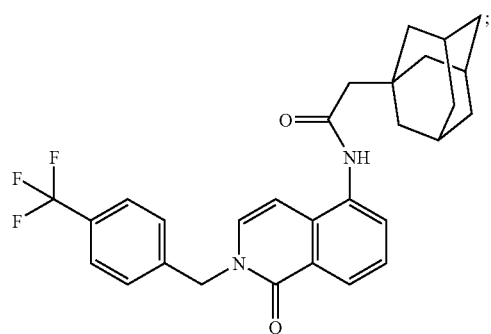 |

-continued
| Name | Structure |
|---|---|
| 2-Adamantan-1-yl-N-(1-oxo-2-pyridin-2-ylmethyl-1,2-dihydro-isoquinolin-5-yl)-acetamide | 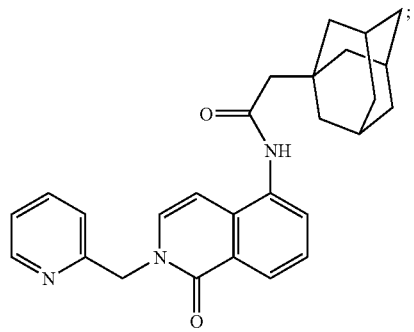 |
| 2-Adamantan-1-yl-N-(1-oxo-2-pyridin-3-ylmethyl-1,2-dihydro-isoquinolin-5-yl)-acetamide | 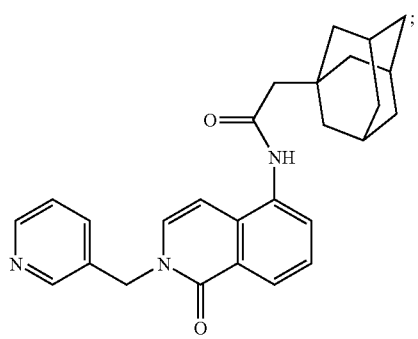 |
| 2-Adamantan-1-yl-N-(1-oxo-2-pyridin-4-ylmethyl-1,2-dihydro-isoquinolin-5-yl)-acetamide | 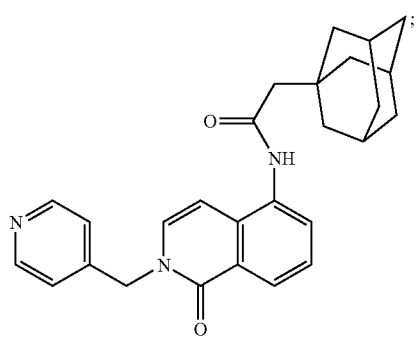 |
| 2-Adamantan-1-yl-N-[1-oxo-2-(tetrahydro-pyran-4-ylmethyl)-1,2-dihydro-isoquinolin-5-yl]-acetamide | 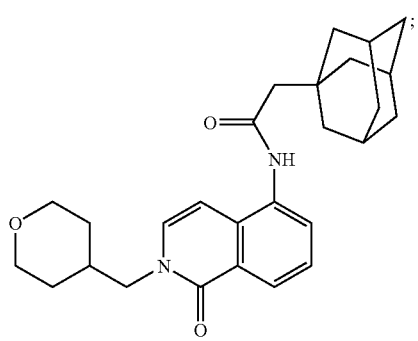 |

-continued
| Name | Structure |
|---|---|
| 2-Adamantan-1-yl-N-[1-oxo-2-(1,3,5-trimethyl-1H-pyrazol-4-ylmethyl)-1,2-dihydro-isoquinolin-5-yl]-acetamide | 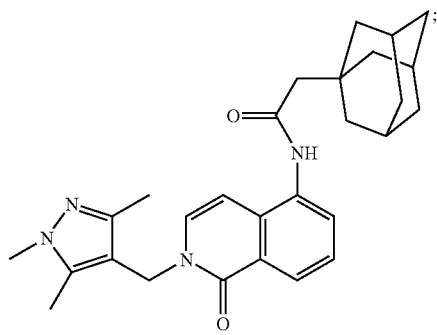 |
| 2-Adamantan-1-yl-N-[2-(1,5-dimethyl-1H-pyrazol-3-ylmethyl)-1-oxo-1,2-dihydro-isoquinolin-5-yl]-acetamide | 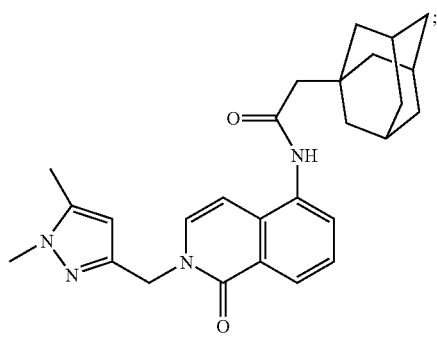 |
| 2-Adamantan-1-yl-N-[1-oxo-2-((S)-1-phenyl-ethyl)-1,2-dihydro-isoquinolin-5-yl]-acetamide | 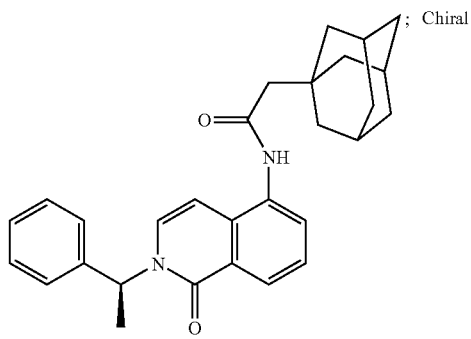 |
| 2-Adamantan-1-yl-N-[1-oxo-2-((R)-1-phenyl-ethyl)-1,2-dihydro-isoquinolin-5-yl]-acetamide | 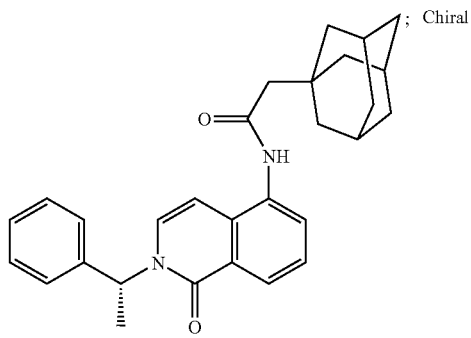 |

-continued
| Name | Structure |
|---|---|
| 2-Adamantan-1-yl-N-[2-(2-chloro-6-fluoro-benzyl)-1-oxo-1,2-dihydro-isoquinolin-5-yl]-acetamide | 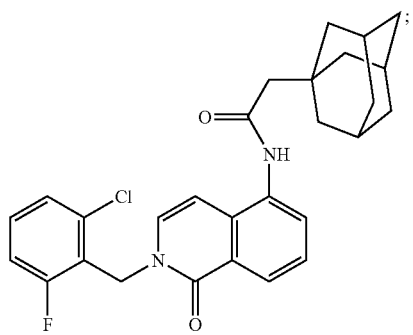 |
| 2-Adamantan-1-yl-N-[2-(2-methyl-benzyl)-1-oxo-1,2-dihydro-isoquinolin-5-yl]-acetamide | 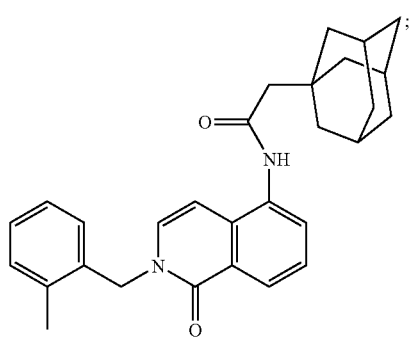 |
| 2-Adamantan-1-yl-N-(2-[1,4]dioxan-2-ylmethyl-1-oxo-1,2-dihydro-isoquinolin-5-yl)-acetamide | 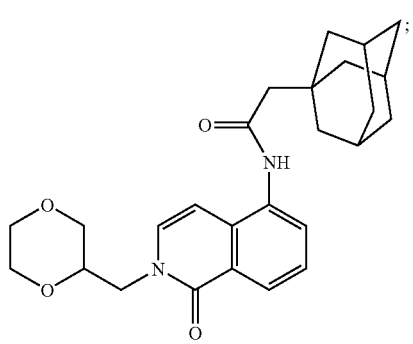 |
| 2-Adamantan-1-yl-N-[2-(2,4-difluoro-benzyl)-1-oxo-1,2,3,4-tetrahydro-isoquinolin-5-yl]-acetamide | 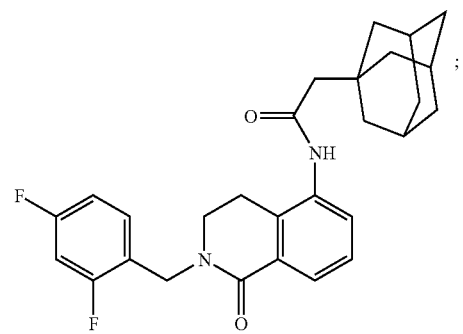 |

-continued
| Name | Structure |
|---|---|
| 2-Adamantan-1-yl-N-[1-oxo-2-(tetrahydro-furan-2-ylmethyl)-1,2,3,4-tetrahydro-isoquinolin-5-yl]-acetamide | 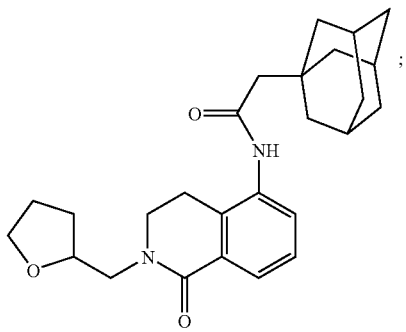 ; |
| 2-Adamantan-1-yl-N-[1-oxo-2-(4-trifluoromethyl-benzyl)-1,2,3,4-tetrahydro-isoquinolin-5-yl]-acetamide | 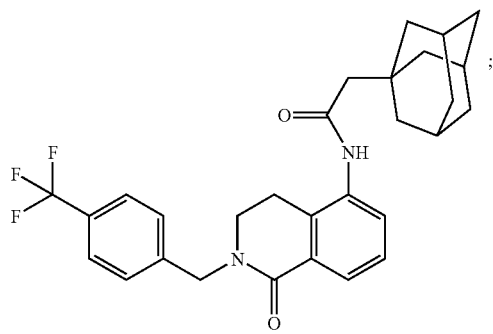 ; |
| 2-Adamantan-1-yl-N-(1-oxo-2-pyridin-3-ylmethyl-1,2,3,4-tetrahydro-isoquinolin-5-yl)-acetamide | 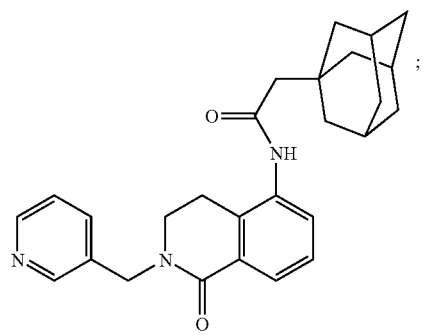 ; |
| 2-Adamantan-1-yl-N-[1-oxo-2-(1,3,5-trimethyl-1H-pyrazol-4-ylmethyl)-1,2,3,4-tetrahydro-isoquinolin-5-yl]-acetamide | 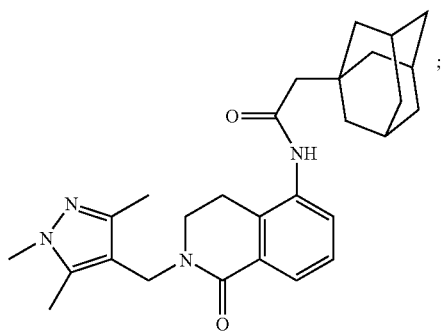 ; |

| Name | Structure |
|---|---|
| 2-Adamantan-1-yl-N-(2-furan-2-ylmethyl-1-oxo-1,2,3,4-tetrahydro-isoquinolin-5-yl)-acetamide | 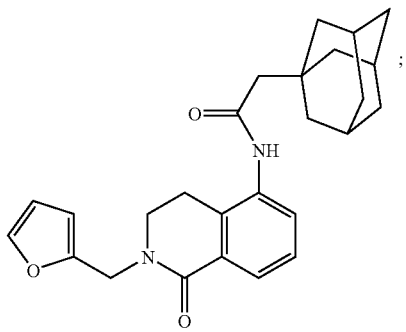 |
| 2-Adamantan-1-yl-N-[1-oxo-2-(1-phenyl-ethyl)-1,2,3,4-tetrahydro-isoquinolin-5-yl]-acetamide | 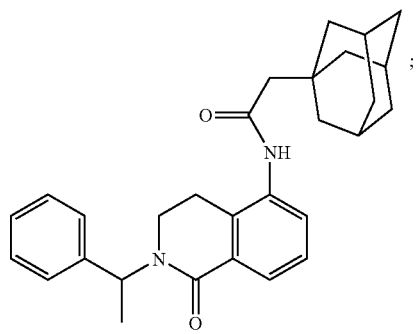 |
| 2-Adamantan-1-yl-N-[2-(5-methyl-pyrazin-2-ylmethyl)-1-oxo-1,2,3,4-tetrahydro-isoquinolin-5-yl]-acetamide | 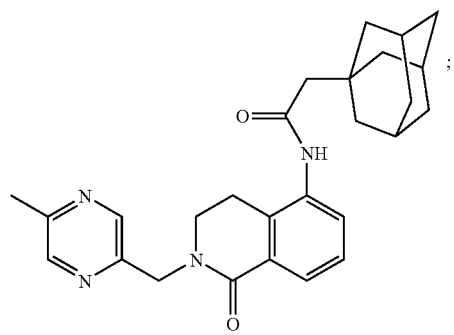 |
| 2-Adamantan-1-yl-N-[2-(2,6-difluoro-benzyl)-1-oxo-1,2-dihydro-isoquinolin-5-yl]-acetamide | 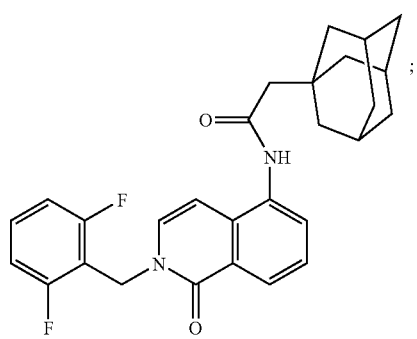 |

| Name | Structure |
|---|---|
| 2-Adamantan-1-yl-N-[2-(2,3-dihydro-benzo[1,4]dioxin-2-ylmethyl)-1-oxo-1,2-dihydro-isoquinolin-5-yl]-acetamide | 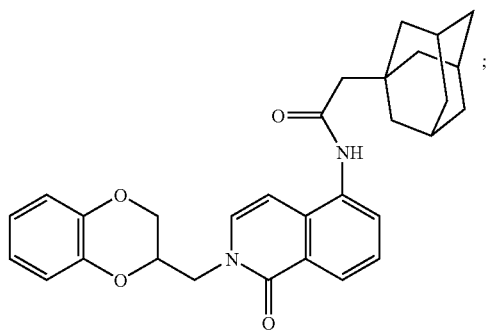 |
| 2-Adamantan-1-yl-N-[2-(3,4-difluoro-benzyl)-1-oxo-1,2-dihydro-isoquinolin-5-yl]-acetamide | 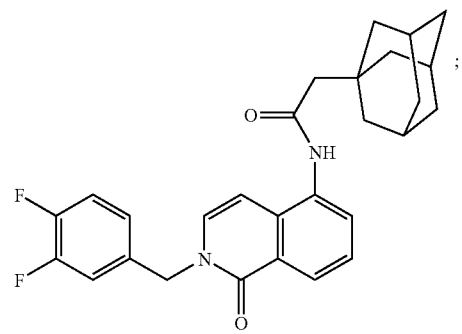 |
| 2-Adamantan-1-yl-N-[2-(2-dimethylamino-ethyl)-1-oxo-1,2-dihydro-isoquinolin-5-yl]-acetamide | 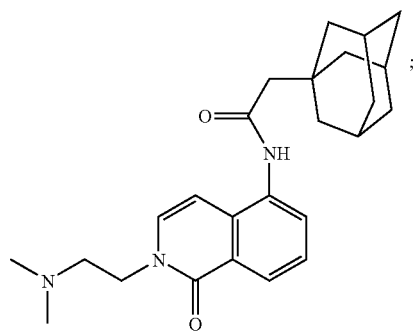 |
| 2-Adamantan-1-yl-N-[2-(5-methyl-isoxazol-3-ylmethyl)-1-oxo-1,2-dihydro-isoquinolin-5-yl]-acetamide | 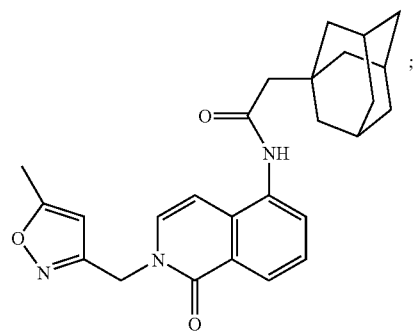 |

| Name | Structure |
|---|---|
| 2-Adamantan-1-yl-N-[2-(5-methyl-2-phenyl-2H-[1,2,3]triazol-4-ylmethyl)-1-oxo-1,2-dihydro-isoquinolin-5-yl]-acetamide | 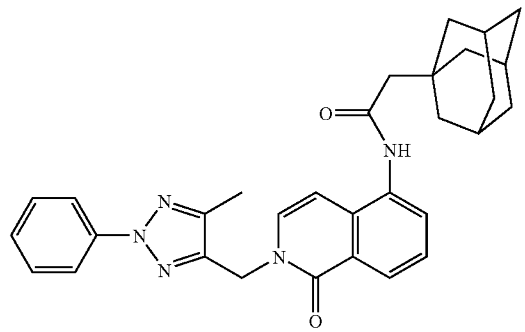 |
| 2-Adamantan-1-yl-N-{1-oxo-2-[(S)-1-(tetrahydro-furan-2-yl)methyl]-1,2-dihydro-isoquinolin-5-yl}-acetamide | Chiral |
| 2-(3,5-Dimethyl-adamantan-1-yl)-N-{2-[2-(1H-imidazol-4-yl)-ethyl]-1-oxo-1,2-dihydro-isoquinolin-5-yl}-acetamide | 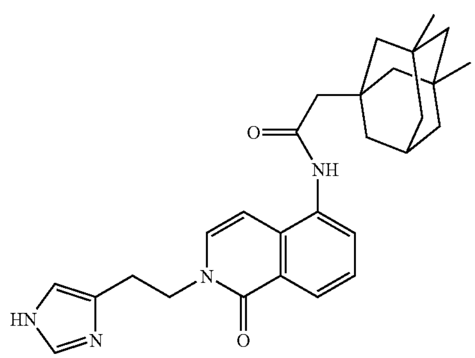 |
| 2-(3,5-Dimethyl-adamantan-1-yl)-N-[1-oxo-2-(1-phenyl-ethyl)-1,2-dihydro-isoquinolin-5-yl]-acetamide | 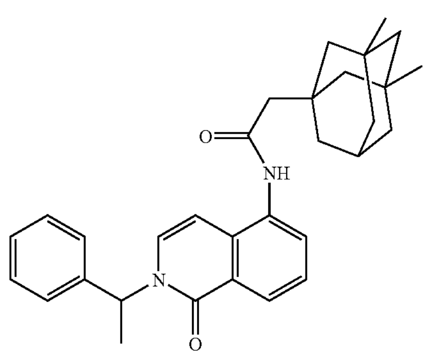 |

-continued

| Name | Structure |
|---|---|
| 2-(3,5-Dimethyl-adamantan-1-yl)-N-[2-(2-fluoro-benzyl)-1-oxo-1,2-dihydro-isoquinolin-5-yl]-acetamide | 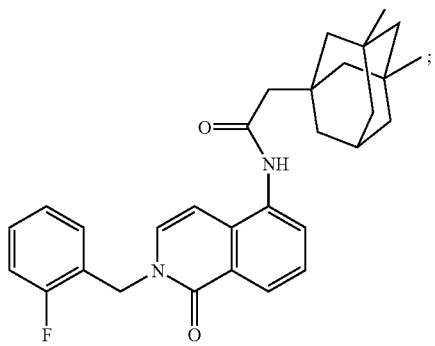 ; |
| 2-(3,5-Dimethyl-adamantan-1-yl)-N-(1-oxo-2-pyridin-2-ylmethyl-1,2-dihydro-isoquinolin-5-yl)-acetamide | 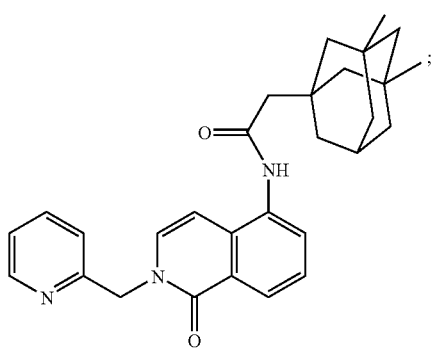 ; |
| 2-(3,5-Dimethyl-adamantan-1-yl)-N-[2-(1,5-dimethyl-1H-pyrazol-3-ylmethyl)-1-oxo-1,2-dihydro-isoquinolin-5-yl]-acetamide | 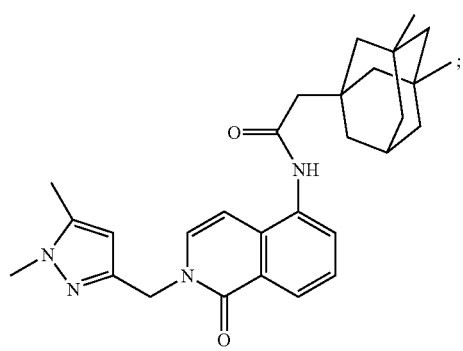 ; |
| 2-(3,5-Dimethyl-adamantan-1-yl)-N-[2-(1-methyl-piperidin-4-ylmethyl)-1-oxo-1,2-dihydro-isoquinolin-5-yl]-acetamide | 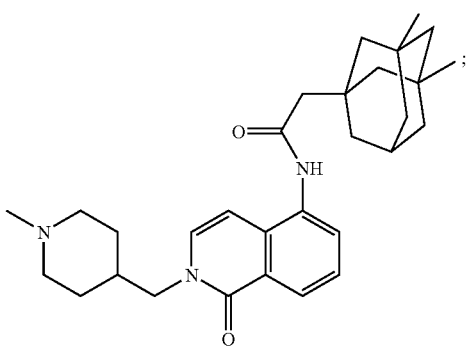 ; |

-continued
| Name | Structure |
|---|---|
| 2-Adamantan-1-yl-N-[2-(4-dimethylamino-benzyl)-1-oxo-1,2-dihydro-isoquinolin-5-yl]-acetamide | 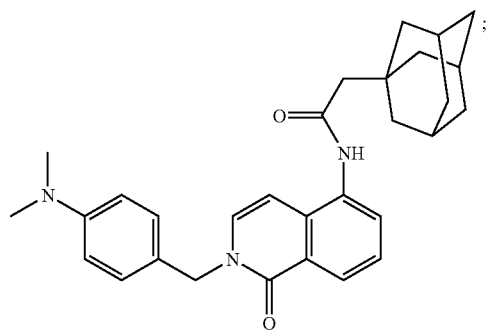 |
| 4-[5-(2-Adamantan-1-yl-acetylamino)-1-oxo-1H-isoquinolin-2-ylmethyl]-piperidine-1-carboxylic acid tert-butyl ester | 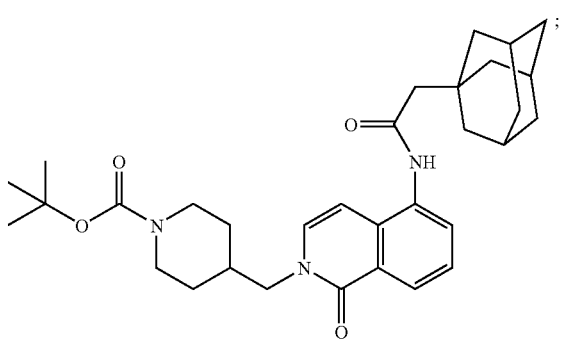 |
| 2-Adamantan-1-yl-N-(1-oxo-2-piperidin-4-ylmethyl-1,2-dihydro-isoquinolin-5-yl)-acetamide | 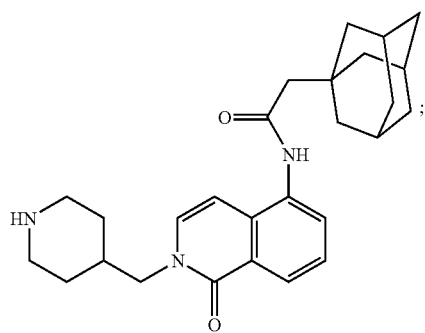 |
| 2-Adamantan-1-yl-N-[2-(1-ethyl-pyrrolidin-2-ylmethyl)-1-oxo-1,2-dihydro-isoquinolin-5-yl]-acetamide | 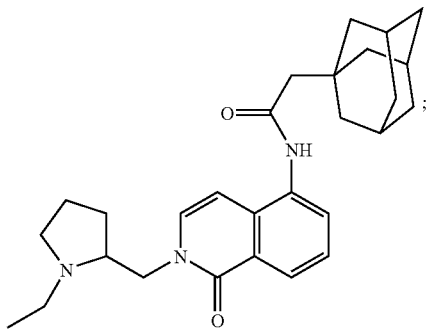 |

-continued
| Name | Structure |
|---|---|
| N-(2-Benzyl-1-oxo-1,2-dihydro-isoquinolin-5-yl)-2-(3,5-dimethyl-adamantan-1-yl)-acetamide | 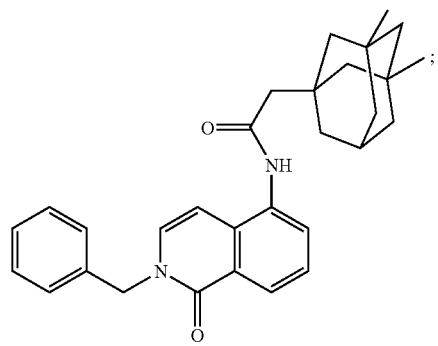 ; |
| 2-(3,5-Dimethyl-adamantan-1-yl)-N-[1-oxo-2-(2-pyridin-2-yl-ethyl)-1,2-dihydro-isoquinolin-5-yl]-acetamide | 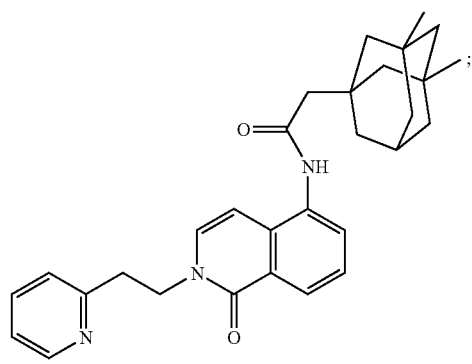 ; |
| 2-(3,5-Dimethyl-adamantan-1-yl)-N-[1-oxo-2-(4-trifluoromethyl-benzyl)-1,2-dihydro-isoquinolin-5-yl]-acetamide | 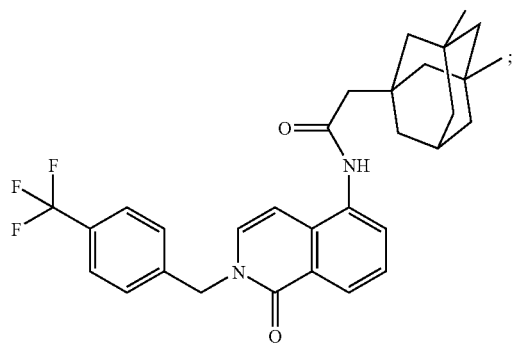 ; |
| 2-(3,5-Dimethyl-adamantan-1-yl)-N-[2-(4-fluoro-benzyl)-1-oxo-1,2-dihydro-isoquinolin-5-yl]-acetamide | 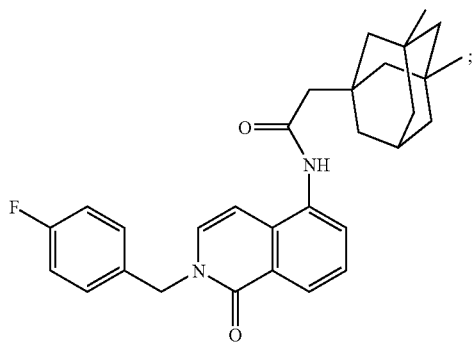 ; |

-continued

| Name | Structure |
|---|---|
| 2-(3,5-Dimethyl-adamantan-1-yl)-N-(1-oxo-2-pyridin-4-ylmethyl-1,2-dihydro-isoquinolin-5-yl)-acetamide | 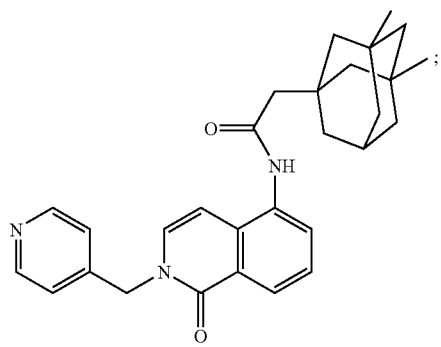 |
| 2-(3,5-Dimethyl-adamantan-1-yl)-N-(1-oxo-2-pyridin-3-ylmethyl-1,2-dihydro-isoquinolin-5-yl)-acetamide | 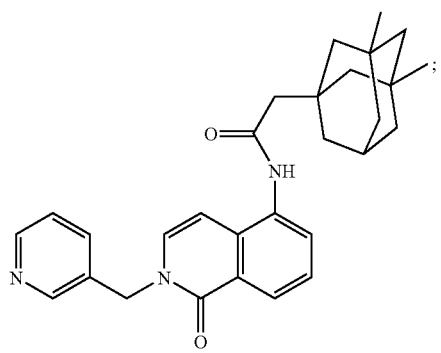 |
| 2-(3,5-Dimethyl-adamantan-1-yl)-N-[2-(5-methyl-pyrazin-2-ylmethyl)-1-oxo-1,2-dihydro-isoquinolin-5-yl]-acetamide | 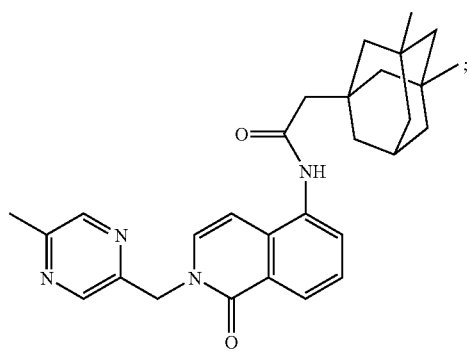 |
| 2-(3,5-Dimethyl-adamantan-1-yl)-N-(2-imidazo[1,2-a]pyridin-2-ylmethyl-1-oxo-1,2-dihydro-isoquinolin-5-yl)-acetamide | 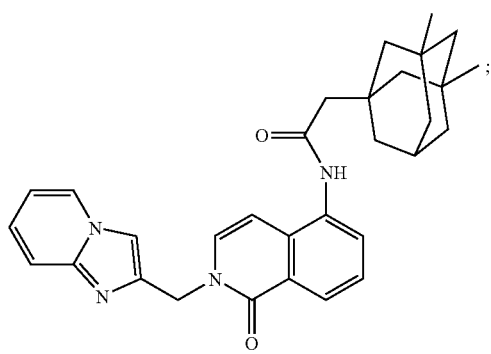 |

| Name | Structure |
|---|---|
| 2-(3,5-Dimethyl-adamantan-1-yl)-N-[2-(4-methanesulfonyl-benzyl)-1-oxo-1,2-dihydro-isoquinolin-5-yl]-acetamide | 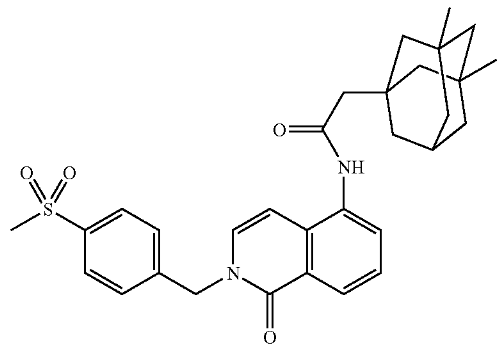 |
| 2-(3,5-Dimethyl-adamantan-1-yl)-N-(2-furan-2-ylmethyl-1-oxo-1,2-dihydro-isoquinolin-5-yl)-acetamide | 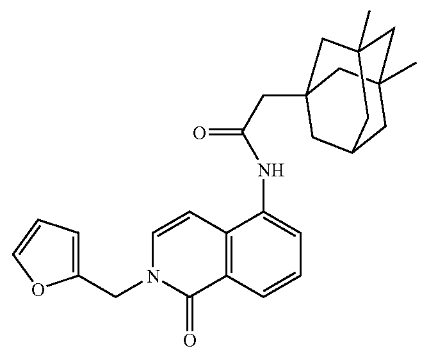 |
| 2-(3,5-Dimethyl-adamantan-1-yl)-N-[2-(5-methyl-isoxazol-3-ylmethyl)-1-oxo-1,2-dihydro-isoquinolin-5-yl]-acetamide | 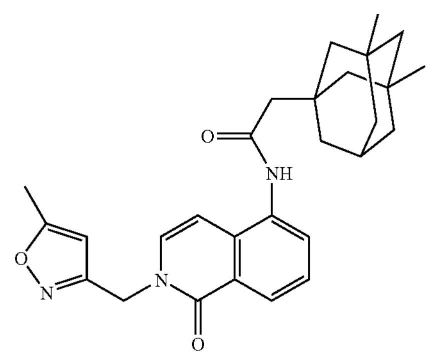 |
| 2-(3,5-Dimethyl-adamantan-1-yl)-N-(2-[1,4]dioxan-2-ylmethyl-1-oxo-1,2-dihydro-isoquinolin-5-yl)-acetamide | 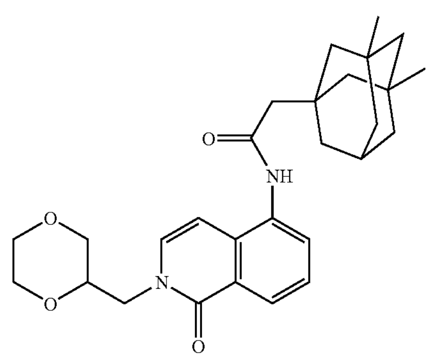 |

| Name | Structure |
|---|---|
| 2-(3,5-Dimethyl-adamantan-1-yl)-N-[2-(2-dimethylamino-ethyl)-1-oxo-1,2-dihydro-isoquinolin-5-yl]-acetamide | 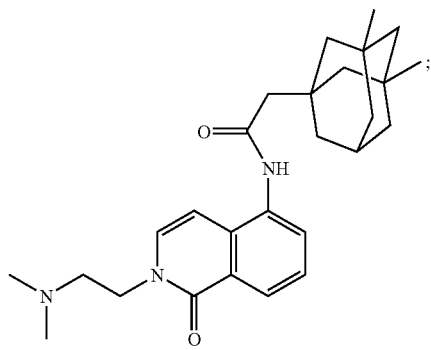 |
| N-[2-(2,4-Difluoro-benzyl)-1-oxo-1,2-dihydro-isoquinolin-5-yl]-2-(3,5-dimethyl-adamantan-1-yl)-acetamide | 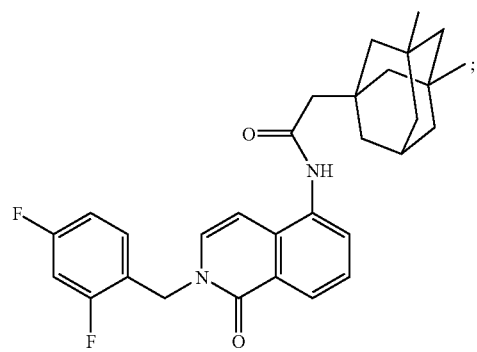 |
| N-[2-(2,4-Difluoro-benzyl)-1-oxo-1,2,3,4-tetrahydro-isoquinolin-5-yl]-2-(3,5-dimethyl-adamantan-1-yl)-acetamide | 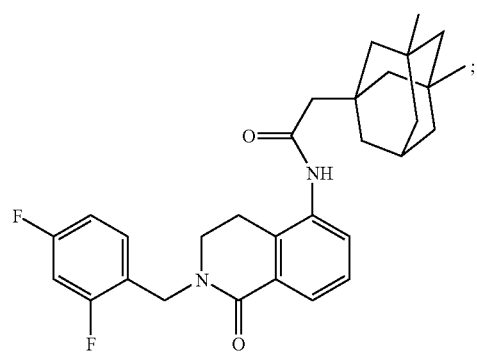 |
| N-[2-(2,3-Dihydro-benzo[1,4]dioxin-2-ylmethyl)-1-oxo-1,2-dihydro-isoquinolin-5-yl]-2-(3,5-dimethyl-adamantan-1-yl)-acetamide | 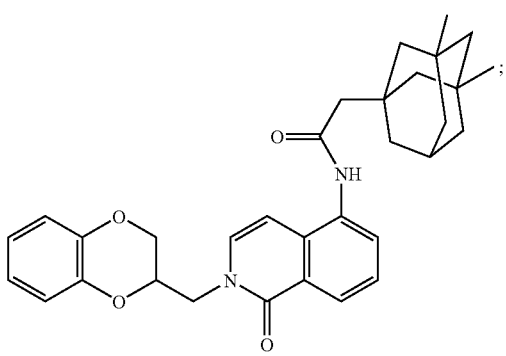 |

-continued
| Name | Structure |
|---|---|
| 2-Adamantan-1-yl-N-[2-(1-methyl-piperidin-4-ylmethyl)-1-oxo-1,2-dihydro-isoquinolin-5-yl]-acetamide | 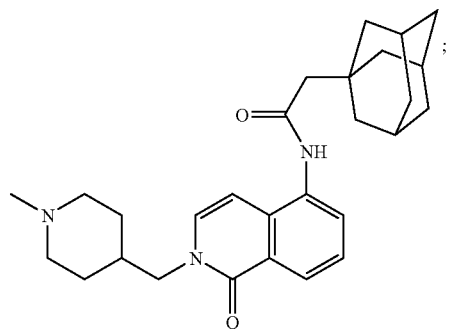 |
| 2-Adamantan-1-yl-N-[2-(4-methanesulfonyl-benzyl)-1-oxo-1,2-dihydro-isoquinolin-5-yl]-acetamide | 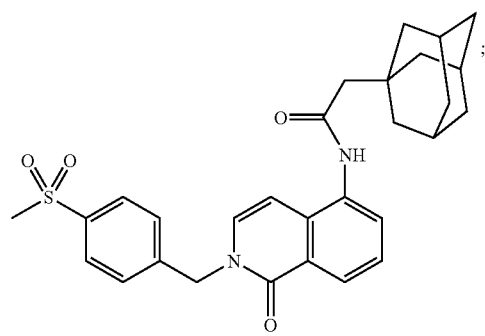 |
| 2-Adamantan-1-yl-N-[2-(2,3-dihydro-benzo[1,4]dioxin-5-ylmethyl)-1-oxo-1,2-dihydro-isoquinolin-5-yl]-acetamide | 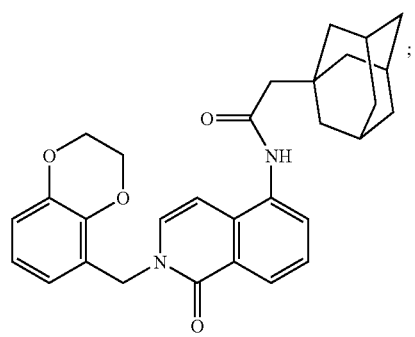 |
| 2-Adamantan-1-yl-N-(2-imidazo[1,2-a]pyridin-2-ylmethyl-1-oxo-1,2-dihydro-isoquinolin-5-yl)-acetamide | 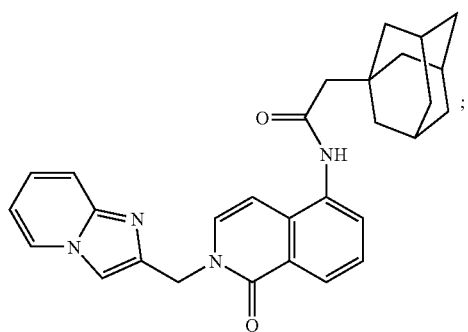 |

-continued

| Name | Structure |
|---|---|
| 2-Adamantan-1-yl-N-{1-oxo-2-[(R)-1-(tetrahydro-furan-2-yl)methyl]-1,2-dihydro-isoquinolin-5-yl}-acetamide | ; Chiral |
| 2-(3,5-Dimethyl-adamantan-1-yl)-N-[2-(1-ethyl-pyrrolidin-2-ylmethyl)-1-oxo-1,2-dihydro-isoquinolin-5-yl]-acetamide | ; |
| 2-[5-(2-Adamantan-1-yl-acetylamino)-1-oxo-1H-isoquinolin-2-ylmethyl]-pyrrolidine-1-carboxylic acid tert-butyl ester | ; |
| (R)-2-[5-(2-Adamantan-1-yl-acetylamino)-1-oxo-1H-isoquinolin-2-ylmethyl]-pyrrolidine-1-carboxylic acid tert-butyl ester | ; Chiral |

-continued

| Name | Structure |
|---|---|
| (S)-2-[5-(2-Adamantan-1-yl-acetylamino)-1-oxo-1H-isoquinolin-2-ylmethyl]-pyrrolidine-1-carboxylic acid tert-butyl ester | ; Chiral |
| (S)-2-[5-(2-Adamantan-1-yl-acetylamino)-1-oxo-1H-isoquinolin-2-yl]-3-phenyl propionamide | ; Chiral |
| N-(2-Benzyl-1-oxo-1,2,3,4-tetrahydro-isoquinolin-5-yl)-2-(3,5-dimethyl-adamantan-1-yl)-acetamide | ; |
| 2-(3,5-Dimethyl-adamantan-1-yl)-N-[2-(5-methyl-pyrazin-2-ylmethyl)-1-oxo-1,2,3,4-tetrahydro-isoquinolin-5-yl]-acetamide | ; |

-continued
| Name | Structure |
|---|---|
| 2-Adamantan-1-yl-N-(2-benzo[1,3]dioxol-5-ylmethyl-1-oxo-1,2-dihydro-isoquinolin-5-yl)-acetamide | 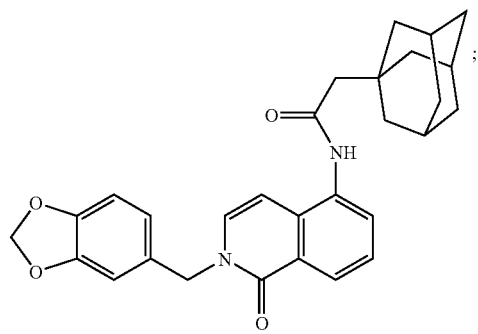 |
| 2-Adamantan-1-yl-N-[2-(2-morpholin-4-yl-ethyl)-1-oxo-1,2-dihydro-isoquinolin-5-yl]acetamide | 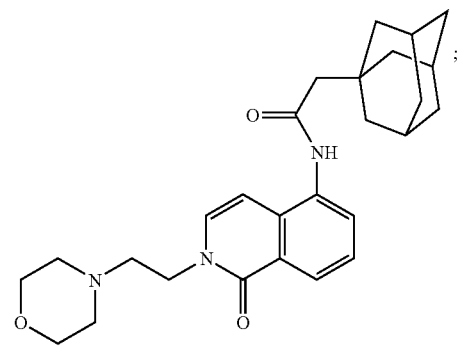 |
| 2-Adamantan-1-yl-N-[2-(3-morpholin-4-yl-propyl)-1-oxo-1,2-dihydro-isoquinolin-5-yl]-acetamide | 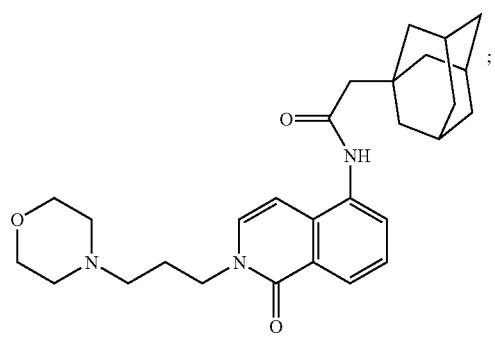 |
| 2-Adamantan-1-yl-N-[1-oxo-2-(2-pyridin-3-yl-ethyl)-1,2-dihydro-isoquinolin-5-yl]-acetamide | 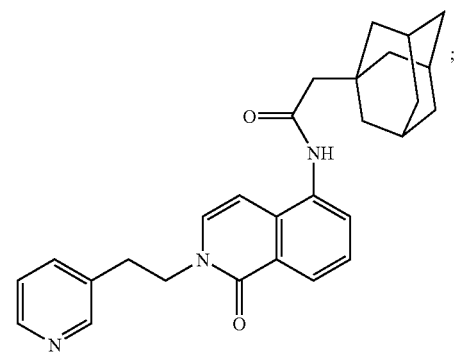 |

| Name | Structure |
|---|---|
| 2-Adamantan-1-yl-N-[1-oxo-2-(2-pyrrolidin-1-yl-ethyl)-1,2-dihydro-isoquinolin-5-yl]-acetamide | 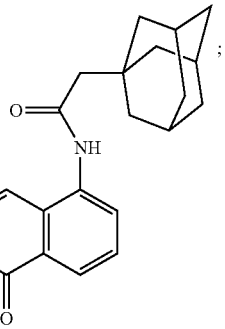 |
| 2-Adamantan-1-yl-N-[1-oxo-2-(2-pyridin-4-yl-ethyl)-1,2-dihydro-isoquinolin-5-yl]-acetamide | 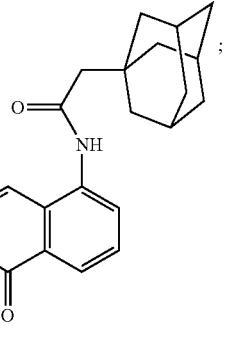 |
| 2-Adamantan-1-yl-N-[1-oxo-2-(2-pyridin-2-yl-ethyl)-1,2-dihydro-isoquinolin-5-yl]-acetamide | 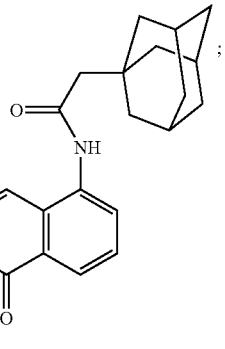 |
| 2-Adamantan-1-yl-N-[1-oxo-2-(2-thiomorpholin-4-yl-ethyl)-1,2-dihydro-isoquinolin-5-yl]-acetamide | 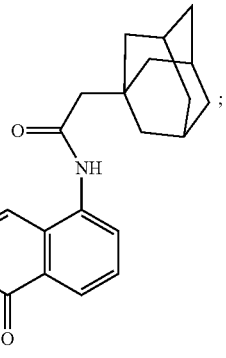 |

| Name | Structure |
|---|---|
| 2-Adamantan-1-yl-N-{2-[3-(4-methyl-piperazin-1-yl)-propyl]-1-oxo-1,2-dihydro-isoquinolin-5-yl}-acetamide | 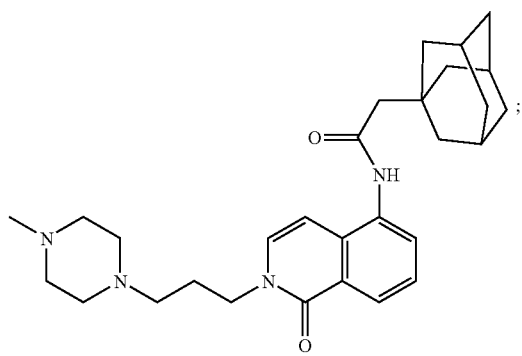 |
| 2-Adamantan-1-yl-N-{2-[2-(1-methyl-pyrrolidin-2-yl)-ethyl]-1-oxo-1,2-dihydro-isoquinolin-5-yl}-acetamide | 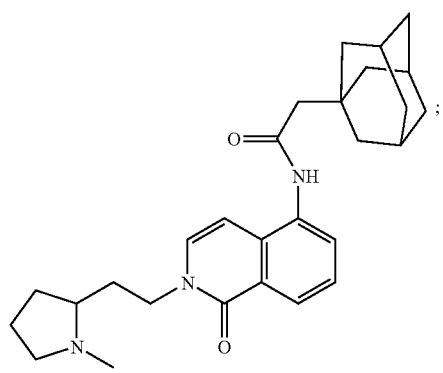 |
| 2-Adamantan-1-yl-N-[1-oxo-2-(3-pyrrolidin-1-yl-propyl)-1,2-dihydro-isoquinolin-5-yl]-acetamide | 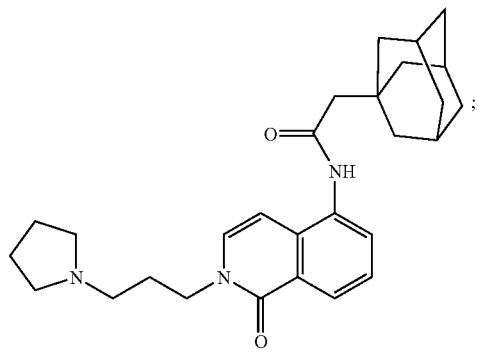 |
| 2-Adamantan-1-yl-N-[2-(2-fluoro-benzyl)-1-oxo-1,2,3,4-tetrahydro-isoquinolin-5-yl]-acetamide | 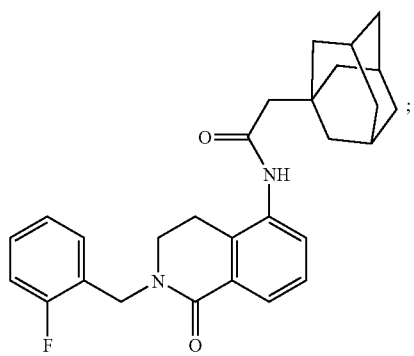 |

| Name | Structure |
|---|---|
| 2-Adamantan-1-yl-N-[2-(2,3-dihydro-benzo[1,4]dioxin-6-ylmethyl)-1-oxo-1,2,3,4-tetrahydro-isoquinolin-5-yl]-acetamide | 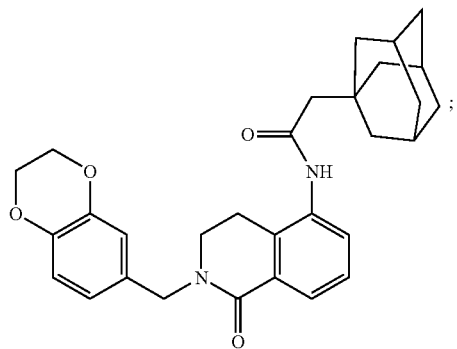 |
| 2-Adamantan-1-yl-N-[2-(2-methyl-benzyl)-1-oxo-1,2,3,4-tetrahydro-isoquinolin-5-yl]-acetamide | 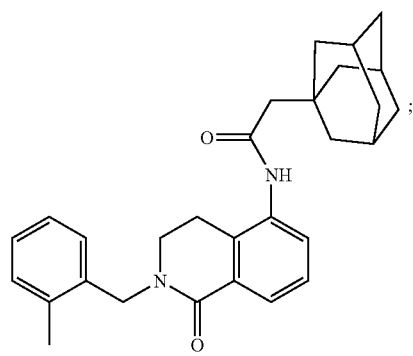 |
| 2-Adamantan-1-yl-N-[2-(2-chloro-benzyl)-1-oxo-1,2,3,4-tetrahydro-isoquinolin-5-yl]-acetamide | 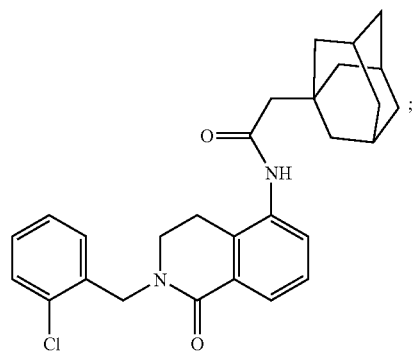 |
| 2-Adamantan-1-yl-N-[2-(1-methyl-piperidin-4-ylmethyl)-1-oxo-1,2,3,4-tetrahydro-isoquinolin-5-yl]-acetamide | 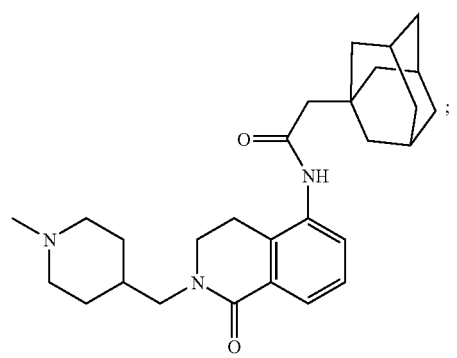 |

| Name | Structure |
|---|---|
| 2-Adamantan-1-yl-N-(1-oxo-2-pyridin-2-ylmethyl-1,2,3,4-tetrahydro-isoquinolin-5-yl)-acetamide | 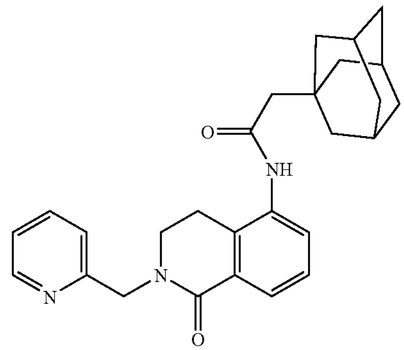 |
| 2-Adamantan-1-yl-N-(2-[1,4]dioxan-2-ylmethyl-1-oxo-1,2,3,4-tetrahydro-isoquinolin-5-yl)-acetamide | 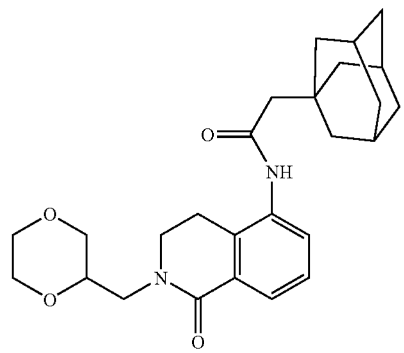 |
| 2-Adamantan-1-yl-N-[2-(1,5-dimethyl-1H-pyrazol-3-ylmethyl)-1-oxo-1,2,3,4-tetrahydro-isoquinolin-5-yl]-acetamide | 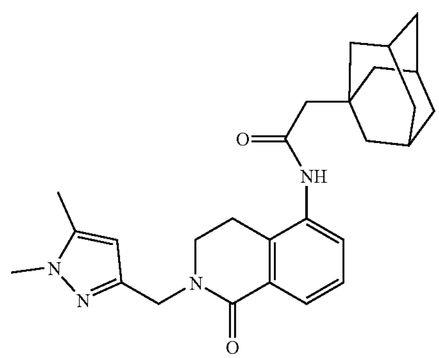 |
| 2-Adamantan-1-yl-N-[2-(2,6-difluoro-benzyl)-1-oxo-1,2,3,4-tetrahydro-isoquinolin-5-yl]-acetamide | 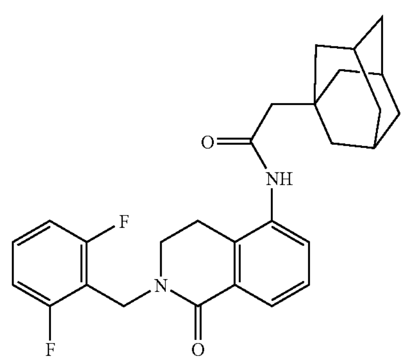 |

| Name | Structure |
|---|---|
| 2-Adamantan-1-yl-N-[2-(3,4-difluoro-benzyl)-1-oxo-1,2,3,4-tetrahydro-isoquinolin-5-yl]-acetamide | 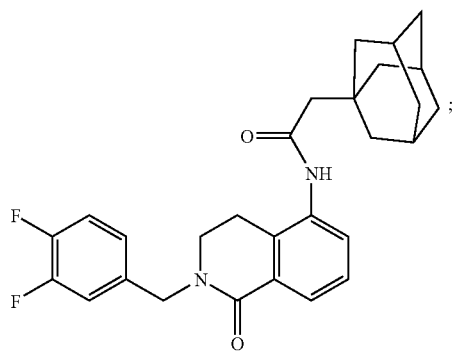 |
| 2-Adamantan-1-yl-N-[2-(2-dimethylamino-ethyl)-1-oxo-1,2,3,4-tetrahydro-isoquinolin-5-yl]-acetamide | 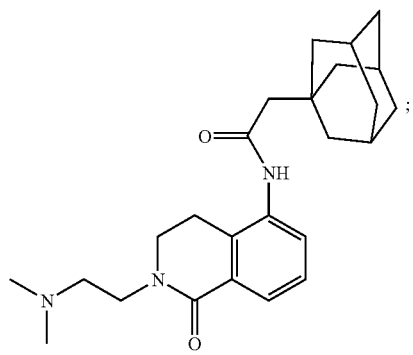 |
| 2-Adamantan-1-yl-N-[2-(5-methyl-isoxazol-3-ylmethyl)-1-oxo-1,2,3,4-tetrahydro-isoquinolin-5-yl]-acetamide | 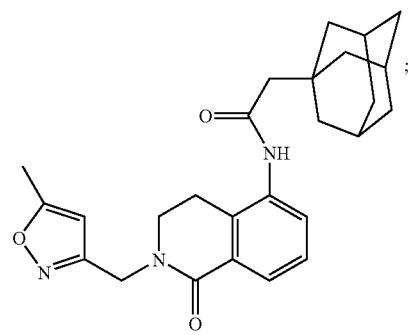 |
| 2-Adamantan-1-yl-N-{2-[2-(1H-imidazol-4-yl)-ethyl]-1-oxo-1,2,3,4-tetrahydro-isoquinolin-5-yl}-acetamide | 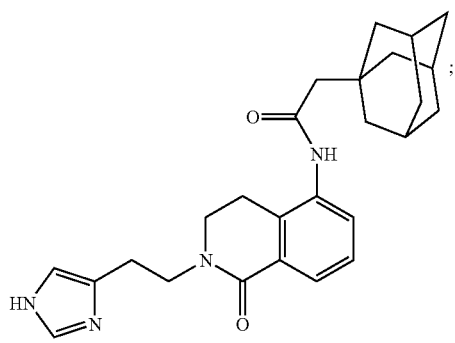 |

| Name | Structure |
|---|---|
| N-[2-(2,3-Dihydro-benzo[1,4]dioxin-6-ylmethyl)-1-oxo-1,2-dihydro-isoquinolin-5-yl]-2-(3,5-dimethyl-adamantan-1-yl)-acetamide | 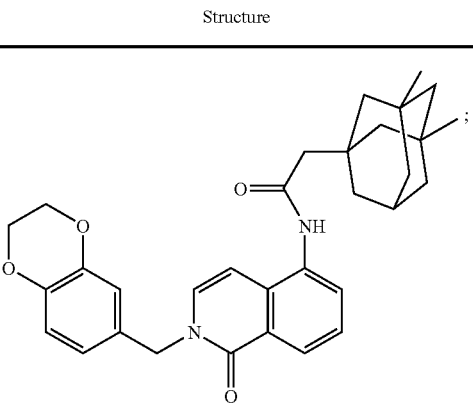 |
| 2-Adamantan-1-yl-N-(1-oxo-1,2-dihydro-isoquinolin-5-yl)-acetamide | 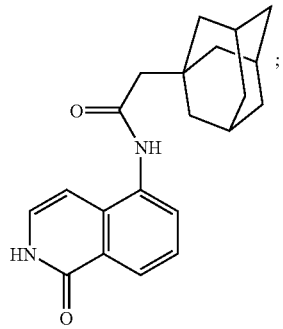 |
| 2-Adamantan-1-yl-N-(2-methyl-1-oxo-1,2-dihydro-isoquinolin-5-yl)-acetamide | 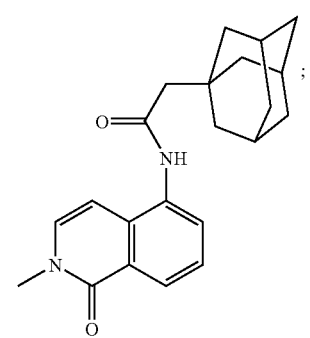 |
| 2-Adamantan-1-yl-N-[2-(5-methyl-piperazin-2-ylmethyl)-1-oxo-1,2,3,4-tetrahydro-isoquinolin-5-yl]-acetamide | 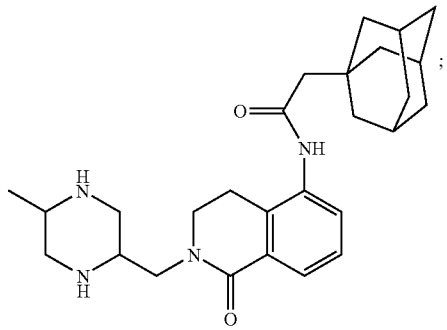 |

-continued
| Name | Structure |
|---|---|
| 2-(3,5-Dimethyl-adamantan-1-yl)-N-(1-oxo-2-pyridin-2-ylmethyl-1,2,3,4-tetrahydro-isoquinolin-5-yl)-acetamide | 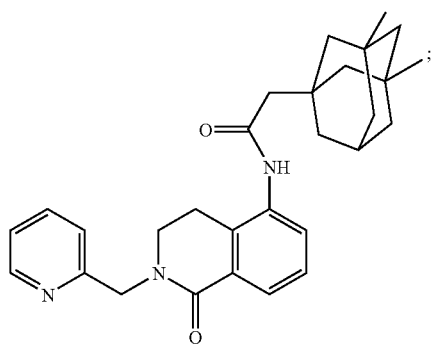 |
| 2-Adamantan-1-yl-N-{2-[2-(1H-imidazol-4-yl)-ethyl]-1-oxo-1,2-dihydro-isoquinolin-5-yl}-acetamide | 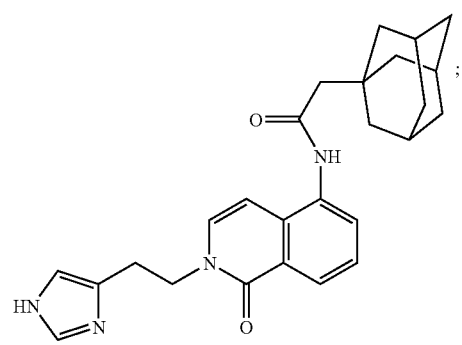 |
| 2-Adamantan-1-yl-N-(1-oxo-2-pyrrolidin-2-ylmethyl-1,2-dihydro-isoquinolin-5-yl) acetamide | 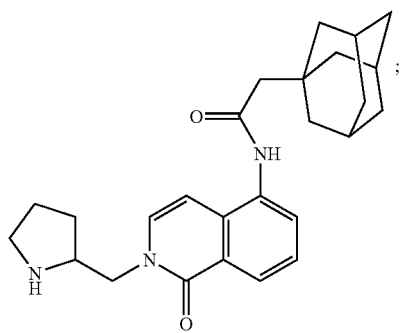 |
| 2-Adamantan-1-yl-N-(1-oxo-2-(S)-1-pyrrolidin-2-ylmethyl-1,2-dihydro-isoquinolin-5-yl)-acetamide | Chiral 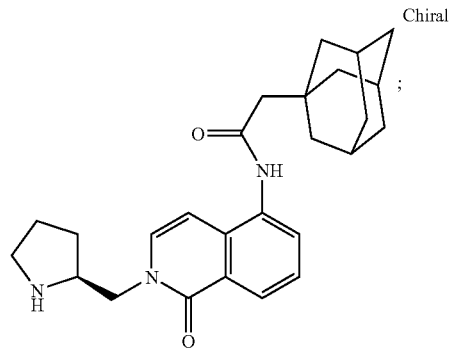 |

| Name | Structure |
|---|---|
| 2-Adamantan-1-yl-N-(1-oxo-2-(R)-1-pyrrolidin-2-ylmethyl-1,2-dihydro-isoquinolin-5-yl)-acetamide | 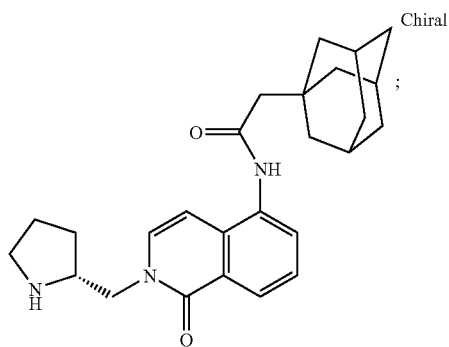 |
| 2-(3,5-Dimethyl-adamantan-1-yl)-N-[1-oxo-2-((S)-1-phenyl-ethyl)-1,2,3,4-tetrahydro-isoquinolin-5-yl]-acetamide | 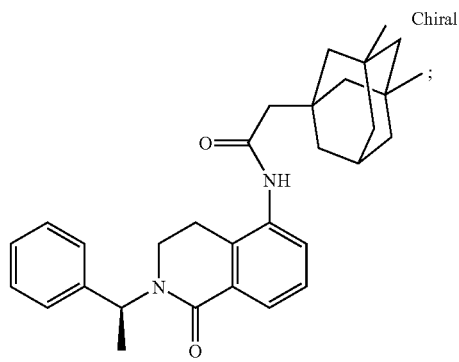 |
| 2-(3,5-Dimethyl-adamantan-1-yl)-N-[1-oxo-2-(tetrahydro-pyran-4-ylmethyl)-1,2,3,4-tetrahydro-isoquinolin-5-yl]-acetamide | 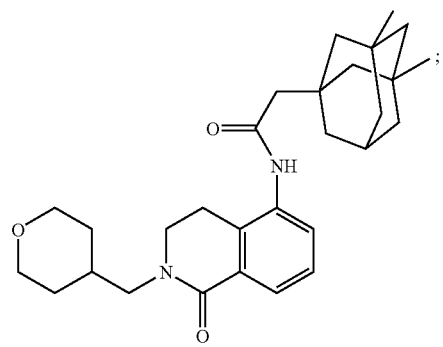 |
| N-(2-Benzo[1,3]dioxol-5-ylmethyl-1-oxo-1,2,3,4-tetrahydro-isoquinolin-5-yl)-2-(3,5-dimethyl-adamantan-1-yl)-acetamide | 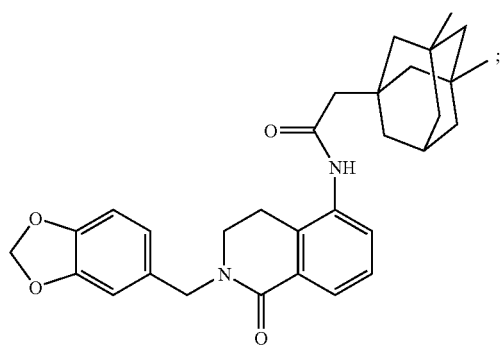 |

-continued
| Name | Structure |
|---|---|
| 2-(3,5-Dimethyl-adamantan-1-yl)-N-[2-(2-morpholin-4-yl-ethyl)-1-oxo-1,2,3,4-tetrahydro-isoquinolin-5-yl]-acetamide | 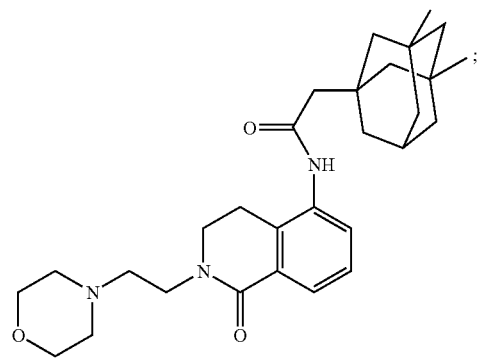 ; |
| 3-Fluoro-adamantane-1-carboxylic acid (2-benzyl-1-oxo-1,2-dihydro-isoquinolin-5-yl)-amide | 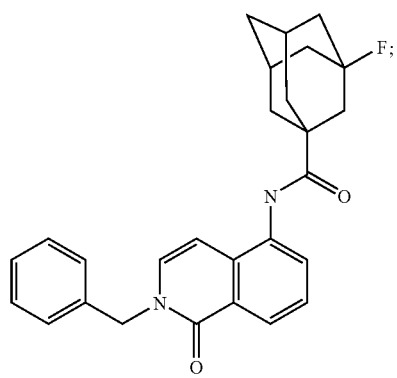 ; |
| 2-Adamantan-1-yl-N-[2-(2-morpholin-4-yl-ethyl)-1-oxo-1,2,3,4-tetrahydro-isoquinolin-5-yl]-acetamide | 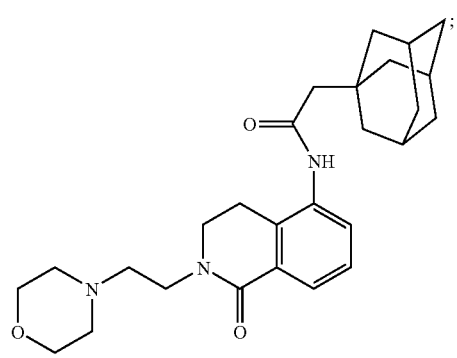 ; |
| 2-(3,5-Dimethyl-adamantan-1-yl)-N-[1-oxo-2-((S)-1-phenyl-ethyl)-1,2-dihydro-isoquinolin-5-yl]-acetamide | 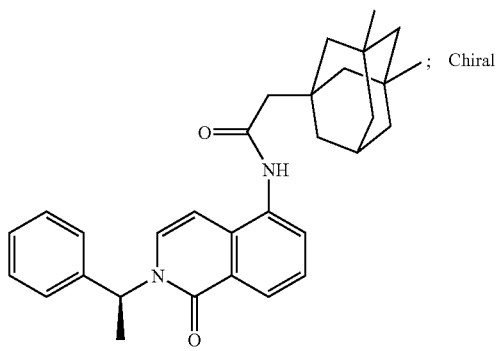 ; Chiral |

| Name | Structure |
|---|---|
| N-[2-(3,4-Difluoro-benzyl)-1-oxo-1,2-dihydro-isoquinolin-5-yl]-2-(3,5-dimethyl-adamantan-1-yl)-acetamide | 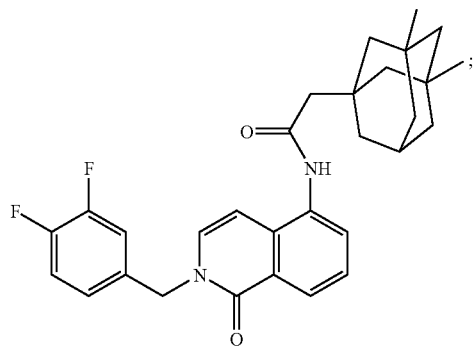 |
| 2-(3,5-Dimethyl-adamantan-1-yl)-N-[1-oxo-2-(tetrahydro-pyran-4-ylmethyl)-1,2-dihydro-isoquinolin-5-yl]-acetamide | 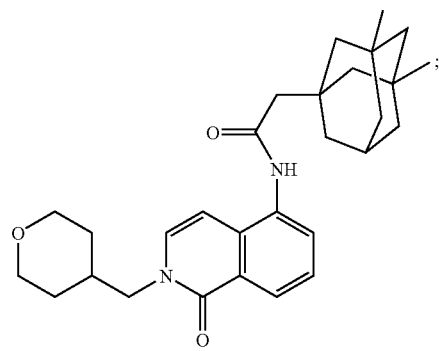 |
| N-(2-Benzo[1,3]dioxol-5-ylmethyl-1-oxo-1,2-dihydro-isoquinolin-5-yl)-2-(3,5-dimethyl-adamantan-1-yl)-acetamide | 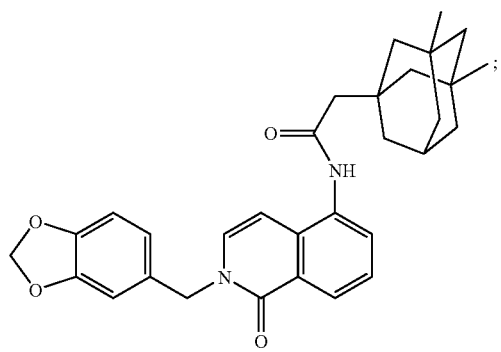 |
| 2-(3,5-Dimethyl-adamantan-1-yl)-N-[2-(3-morpholin-4-yl-propyl)-1-oxo-1,2,3,4-tetrahydro-isoquinolin-5-yl]-acetamide | 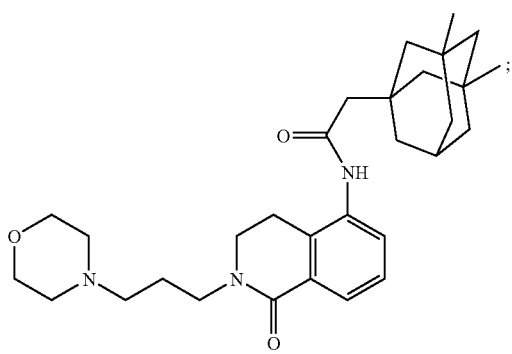 |

-continued

| Name | Structure |
|---|---|
| N-[2-(2,3-Dihydro-benzo[1,4]dioxin-6-ylmethyl)-1-oxo-1,2,3,4-tetrahydro-isoquinolin-5-yl]-2-(3,5-dimethyl-adamantan-1-yl)-acetamide | 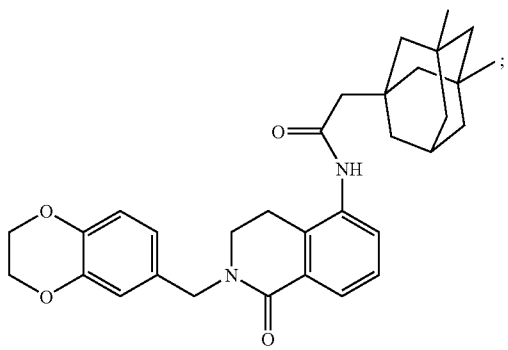 |
| 2-Adamantan-1-yl-N-[2-(3-imidazol-1-yl-propyl)-1-oxo-1,2-dihydro-isoquinolin-5-yl]-acetamide | 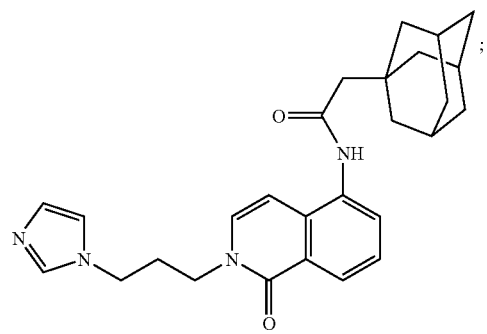 |
| 2-Adamantan-1-yl-N-[2-(3-methyl-pyridin-2-ylmethyl)-1-oxo-1,2,3,4-tetrahydro-isoquinolin-5-yl]-acetamide | 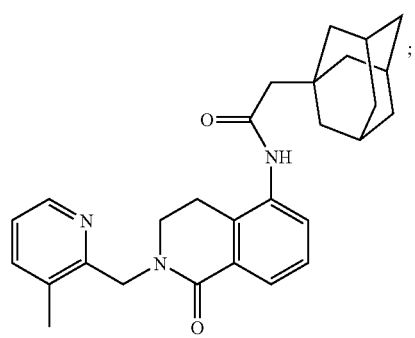 |
| 2-Adamantan-1-yl-N-[2-(2-hydroxy-1-hydroxymethyl-ethyl)-1-oxo-1,2-dihydro-isoquinolin-5-yl]-acetamide | 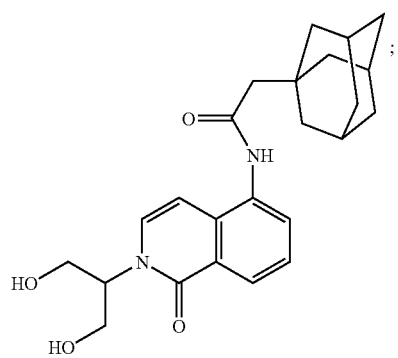 |

-continued

| Name | Structure |
|---|---|
| 2-Adamantan-1-yl-N-[2-(2-hydroxy-1-hydroxymethyl-ethyl)-1-oxo-1,2,3,4-tetrahydro-isoquinolin-5-yl]-acetamide | 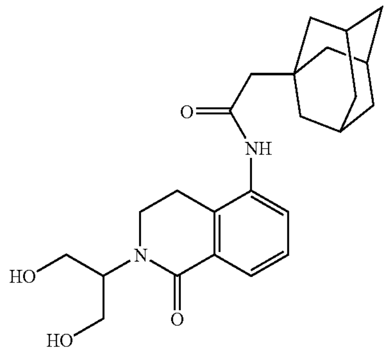 |
| 2-[5-(2-Adamantan-1-yl-acetylamino)-1-oxo-1H-isoquinolin-2-yl]-acetamide | 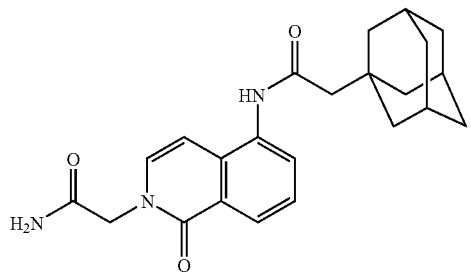 |
| 3-[5-(2-Adamantan-1-yl-acetylamino)-1-oxo-1H-isoquinolin-2-yl]-propionamide | 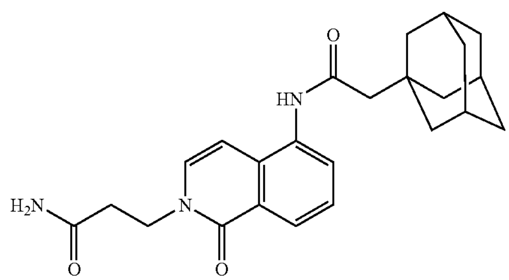 |
| 2-Adamantan-1-yl-N-[1-oxo-2-(2-piperazin-1-yl-ethyl)-1,2-dihydro-isoquinolin-5-yl]-acetamide | 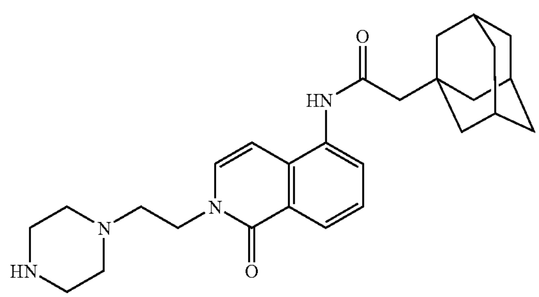 |
| 4-{2-[5-(2-Adamantan-1-yl-acetylamino)-1-oxo-1H-isoquinolin-2-yl]-ethyl}-piperazine-1-carboxylic acid tert-butyl ester | 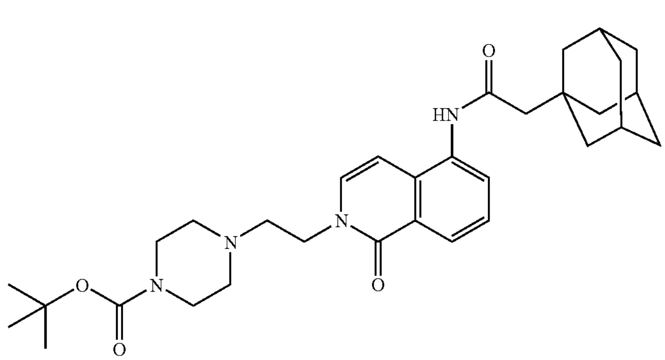 |

| Name | Structure |
|---|---|
| 3-Fluoro-adamantane-1-carboxylic acid (2-benzyl-1-oxo-1,2,3,4-tetrahydro-isoquinolin-5-yl)-amide | 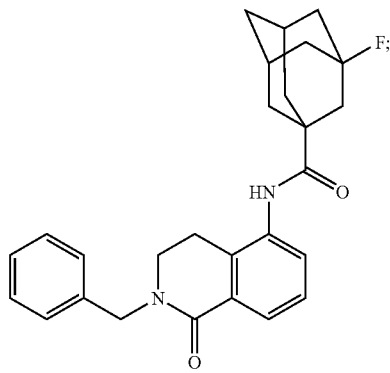 |
| 2-Adamantan-1-yl-N-[1-oxo-2-(tetrahydro-pyran-4-ylmethyl)-1,2,3,4-tetrahydro-isoquinolin-5-yl]-acetamide | 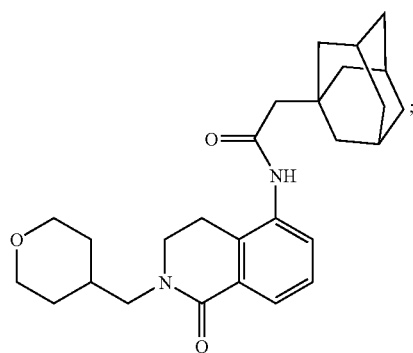 |
| 2-Adamantan-1-yl-N-[2-(1-ethyl-pyrrolidin-2-ylmethyl)-1-oxo-1,2,3,4-tetrahydro-isoquinolin-5-yl]-acetamide | 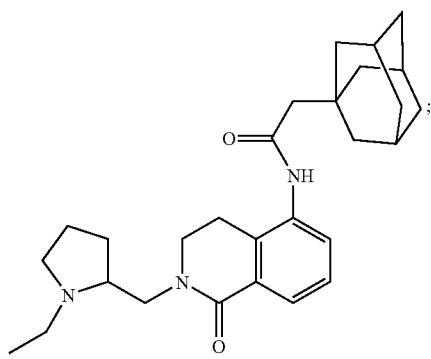 |
| N-[2-(2,6-Difluoro-benzyl)-1-oxo-1,2-dihydro-isoquinolin-5-yl]-2-(3,5-dimethyl-adamantan-1-yl)-acetamide | 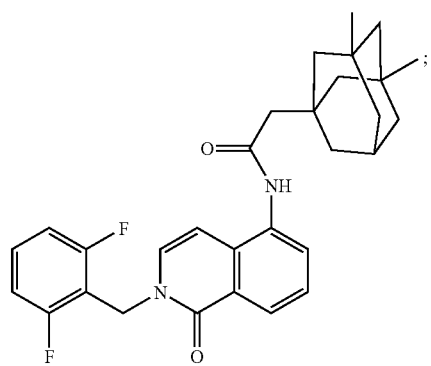 |

| Name | Structure |
|---|---|
| 2-Adamantan-1-yl-N-[2-(3-imidazol-1-yl-propyl)-1-oxo-1,2,3,4-tetrahydro-isoquinolin-5-yl]-acetamide | 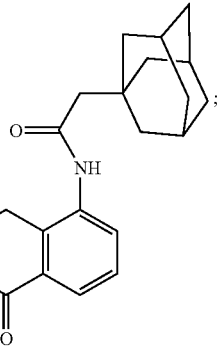 |
| 2-Adamantan-1-yl-N-[1-oxo-2-(1-pyridin-3-yl-ethyl)-1,2-dihydro-isoquinolin-5-yl]-acetamide | 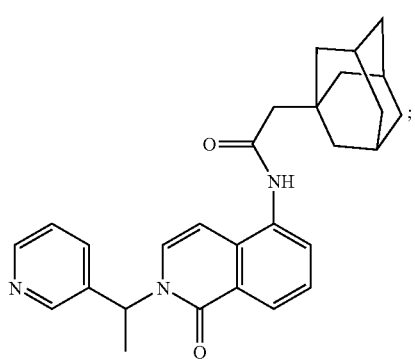 |
| 2-(3,5-Dimethyl-adamantan-1-yl)-N-[1-oxo-2-(1-phenyl-ethyl)-1,2,3,4-tetrahydro-isoquinolin-5-yl]-acetamide | 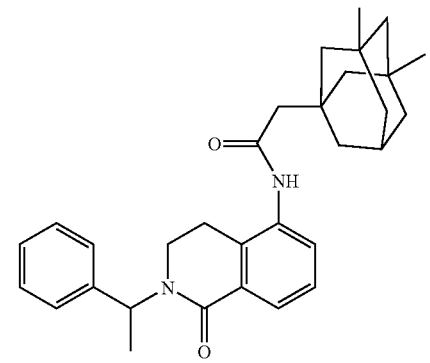 |
| 2-(3,5-Dimethyl-adamantan-1-yl)-N-[2-(2-fluoro-benzyl)-1-oxo-1,2,3,4-tetrahydro-isoquinolin-5-yl]-acetamide | 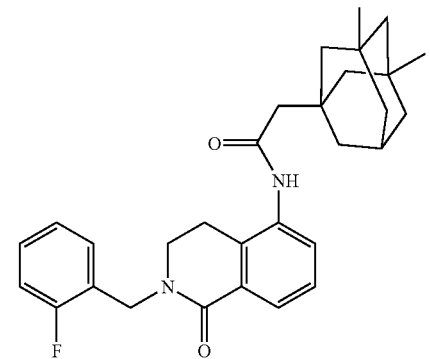 |

| Name | Structure |
|---|---|
| N-[2-(2,6-Difluoro-benzyl)-1-oxo-1,2,3,4-tetrahydro-isoquinolin-5-yl]-2-(3,5-dimethyl-adamantan-1-yl)-acetamide | 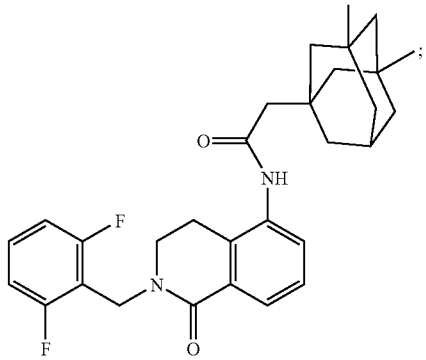 |
| 2-(3,5-Dimethyl-adamantan-1-yl)-N-(1-oxo-1,2-dihydro-isoquinolin-5-yl)-acetamide | 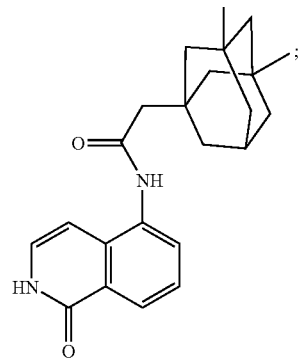 |
| 2-Adamantan-1-yl-N-{2-[2-(4-methyl-piperazin-1-yl)-ethyl]-1-oxo-1,2-dihydro-isoquinolin-5-yl}-acetamide | 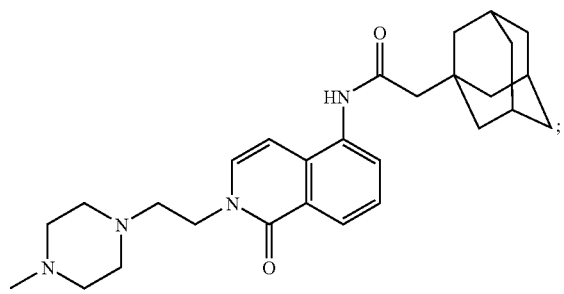 |
| 2-Adamantan-1-yl-N-[2-(1,1-dimethyl-2-morpholin-4-yl-ethyl)-1-oxo-1,2-dihydro-isoquinolin-5-yl]-acetamide | 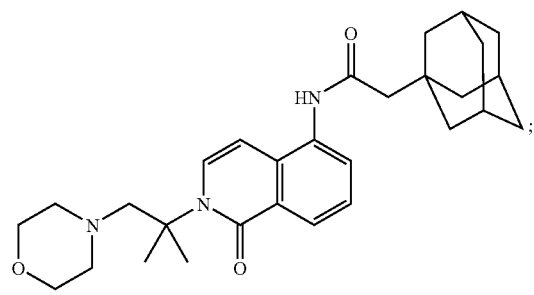 |

-continued
| Name | Structure |
|---|---|
| 2-Adamantan-1-yl-N-[2-(2-hydroxy-ethyl)-1-oxo-1,2-dihydro-isoquinolin-5-yl]-acetamide | 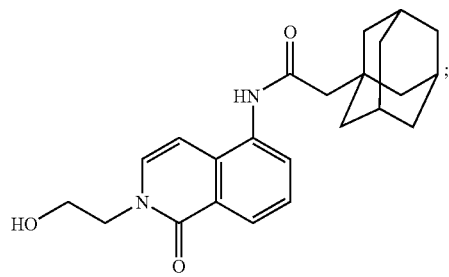 |
| 2-[5-(2-Adamantan-1-yl-acetylamino)-1-ylmethyl]-pyrrolidine-1-carboxylic acid tert-oxo-3,4-dihydro-1H-isoquinolin-2-butyl ester | 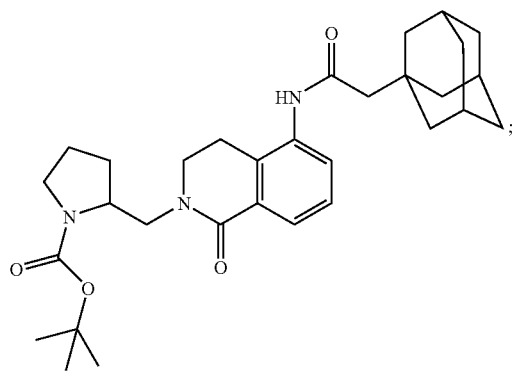 |
| 2-Adamantan-1-yl-N-[1-oxo-2-(1-pyridin-2-yl-ethyl)-1,2-dihydro-isoquinolin-5-yl]-acetamide | 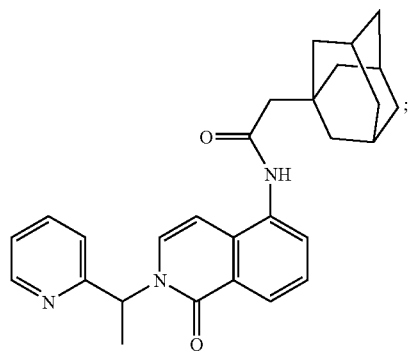 |
| 2-Adamantan-1-yl-N-[1-oxo-2-(1-pyridin-4-yl-ethyl)-1,2-dihydro-isoquinolin-5-yl]-acetamide | 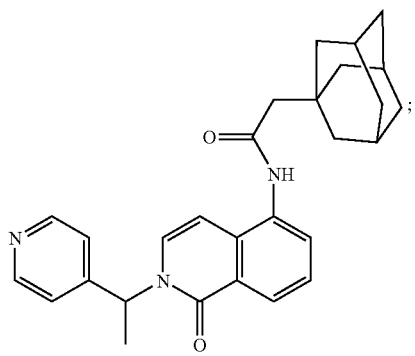 |

-continued
| Name | Structure |
|---|---|
| 2-Adamantan-1-yl-N-{2-[2-(2,6-dimethyl-morpholin-4-yl)-ethyl]-1-oxo-1,2-dihydro-isoquinolin-5-yl}-acetamide | 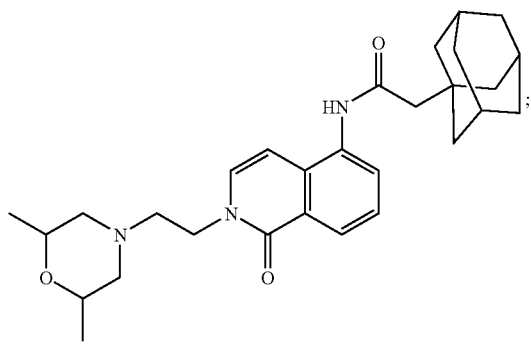 |
| 2-Adamantan-1-yl-N-[2-(2-diethylamino-ethyl)-1-oxo-1,2-dihydro-isoquinolin-5-yl]-acetamide | 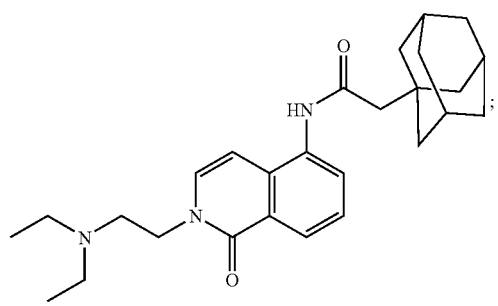 |
| 2-Adamantan-1-yl-N-(2-isobutyl-1-oxo-1,2-dihydro-isoquinolin-5-yl)-acetamide | 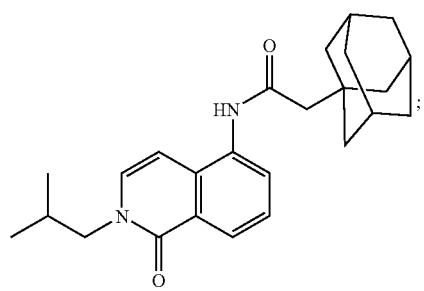 |
| 2-Adamantan-1-yl-N-[2-(2,3-dihydro-benzo[1,4]dioxin-2-ylmethyl)-1-oxo-1,2,3,4-tetrahydro-isoquinolin-5-yl]-acetamide | 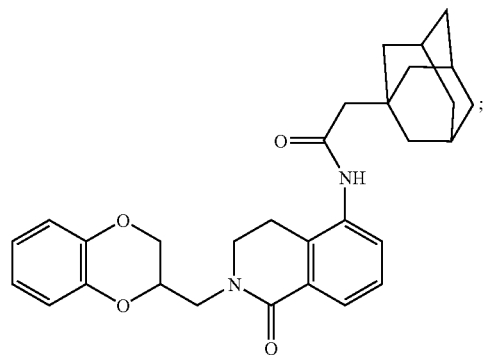 |

| Name | Structure |
|---|---|
| 2-Adamantan-1-yl-N-(2-furan-3-ylmethyl-1-oxo-1,2-dihydro-isoquinolin-5-yl)-acetamide | 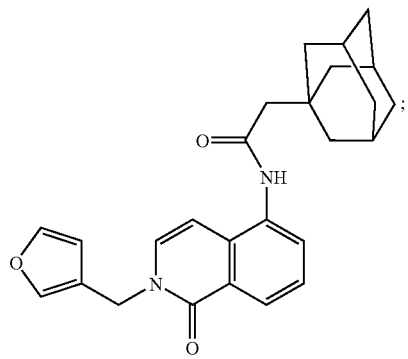 |
| 2-Adamantan-1-yl-N-(1-oxo-1,2,3,4-tetrahydro-isoquinolin-5-yl)-acetamide | 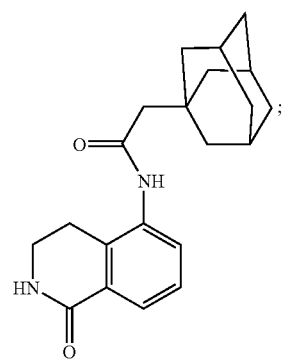 |
| 2-Adamantan-1-yl-N-(1-oxo-2-piperidin-4-ylmethyl-1,2,3,4-tetrahydro-isoquinolin-5-yl)-acetamide | 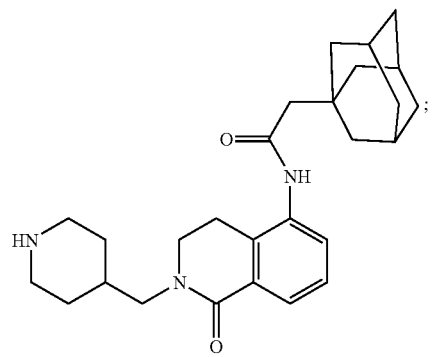 |
| 2-Adamantan-1-yl-N-[2-(3-morpholin-4-yl-propyl)-1-oxo-1,2,3,4-tetrahydro-isoquinolin-5-yl]-acetamide | 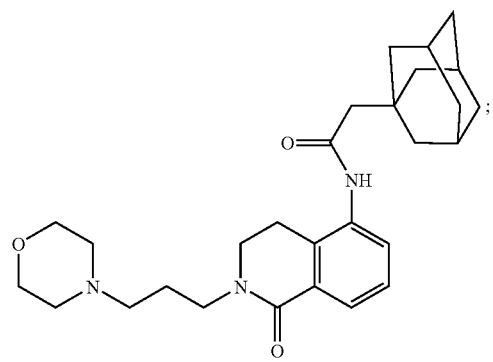 |

| Name | Structure |
|---|---|
| 2-Adamantan-1-yl-N-[1-oxo-2-(2-pyrrolidin-1-yl-ethyl)-1,2,3,4-tetrahydro-isoquinolin-5-yl]-acetamide | 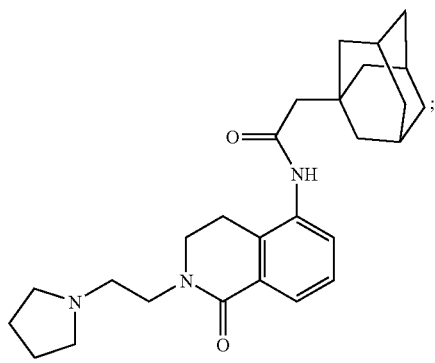 |
| 2-Adamantan-1-yl-N-{2-[3-(4-methyl-piperazin-1-yl)-propyl]-1-oxo-1,2,3,4-tetrahydro-isoquinolin-5-yl}-acetamide | 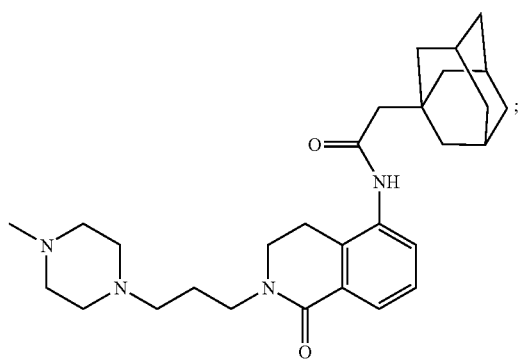 |
| 2-Adamantan-1-yl-N-{2-[2-(1-methyl-pyrrolidin-2-yl)-ethyl]-1-oxo-1,2,3,4-tetrahydro-isoquinolin-5-yl}-acetamide | 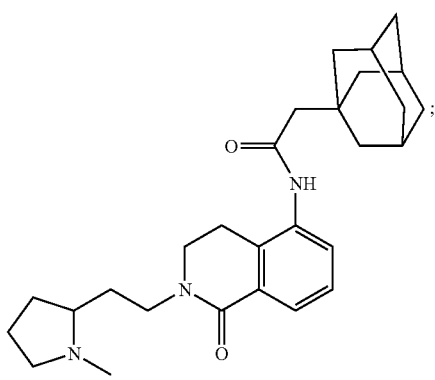 |
| 2-Adamantan-1-yl-N-[1-oxo-2-(3-pyrrolidin-1-yl-propyl)-1,2,3,4-tetrahydro-isoquinolin-5-yl]-acetamide | 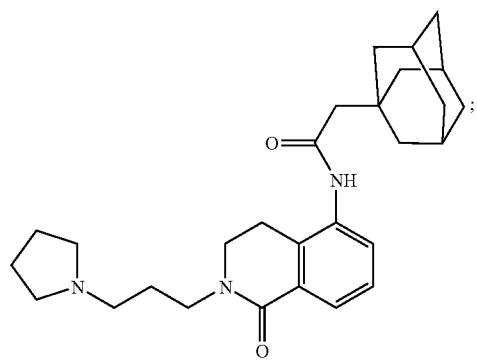 |

| Name | Structure |
|---|---|
| (R)-2-[5-(2-Adamantan-1-yl-acetylamino)-1-oxo-1H-isoquinolin-2-yl]-3-cyclohexyl-propionamide | 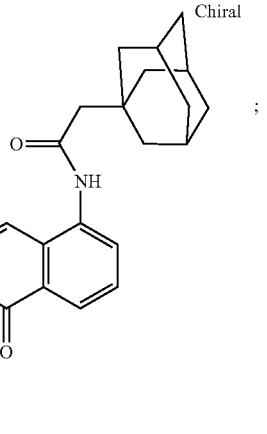 |
| (S)-2-[5-(2-Adamantan-1-yl-acetylamino)-1-oxo-1H-isoquinolin-2-yl]-3-(1H-imidazol 4-yl)-propionamide | 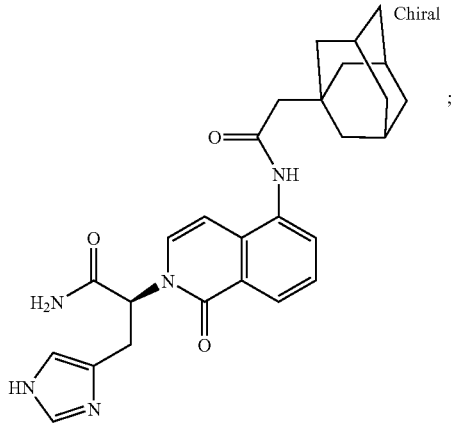 |
| 2-Adamantan-1-yl-N-{2-[(R)-2-hydroxy-1-(1H-imidazol-4-ylmethyl)-ethyl]-1-oxo-1,2-dihydro-isoquinolin-5-yl}-acetamide | 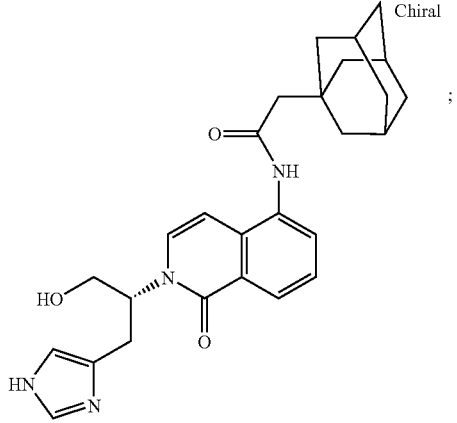 |
| 2-Adamantan-1-yl-N-[1-oxo-2-(pyridin-2-ylamino)-1,2-dihydro-isoquinolin-5-yl]-acetamide | 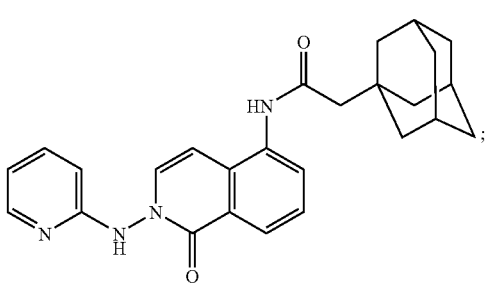 |

-continued

| Name | Structure |
|---|---|
| 2-Adamantan-1-yl-N-(1-oxo-2-thiazol-2-ylmethyl-1,2-dihydro-isoquinolin-5-yl)-acetamide | 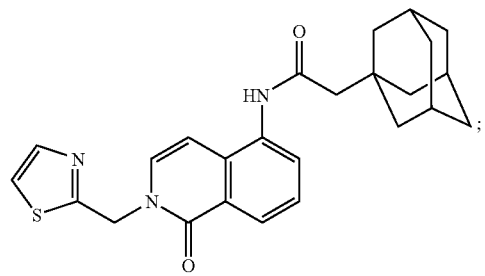 |
| 2-Adamantan-1-yl-N-{2-[2-(4-methyl-piperazin-1-yl)-ethyl]-1-oxo-1,2,3,4-tetrahydro-isoquinolin-5-yl}-acetamide | 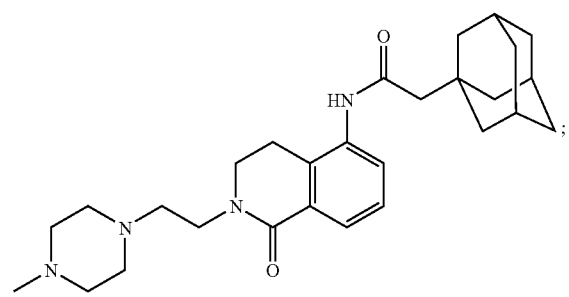 |
| 2-Adamantan-1-yl-N-[2-(1-hydroxymethyl-2-methyl-propyl)-1-oxo-1,2-dihydro-isoquinolin-5-yl]-acetamide | 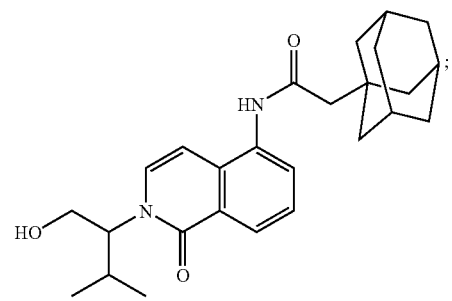 |
| 2-Adamantan-1-yl-N-[2-(2-hydroxy-1-methyl-ethyl)-1-oxo-1,2-dihydro-isoquinolin-5-yl]-acetamide | 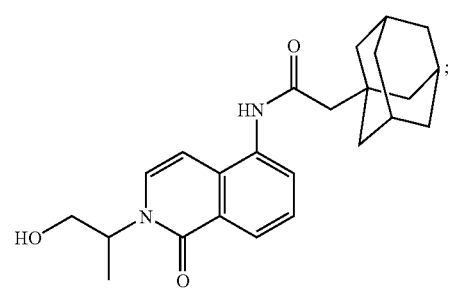 |
| 2-(3,5-Dimethyl-adamantan-1-yl)-N-(1-oxo-2-piperidin-4-ylmethyl-1,2-dihydro-isoquinolin-5-yl)-acetamide | 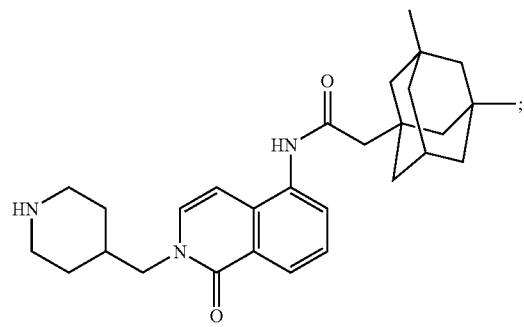 |

| Name | Structure |
|---|---|
| 2-Adamantan-1-yl-N-methyl-N-(1-oxo-2-vinyl-1,2-dihydro-isoquinolin-5-yl)-acetamide | 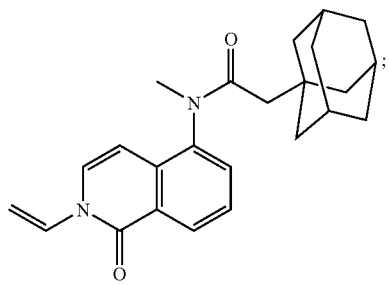 |
| 2-(3,5-Dimethyl-adamantan-1-yl)-N-[2-(3-morpholin-4-yl-propyl)-1-oxo-1,2-dihydro-isoquinolin-5-yl]-acetamide | 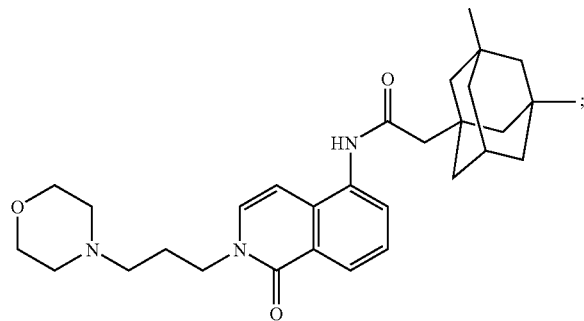 |
| 2-Adamantan-1-yl-N-(2-isobutyl-1-oxo-1,2-dihydro-isoquinolin-5-yl)-N-methyl-acetamide | 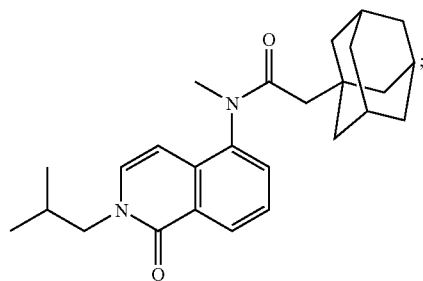 |
| 2-(3,5-Dimethyl-adamantan-1-yl)-N-[2-(1-methyl-piperidin-4-ylmethyl)-1-oxo-1,2,3,4-tetrahydro-isoquinolin-5-yl]-acetamide | 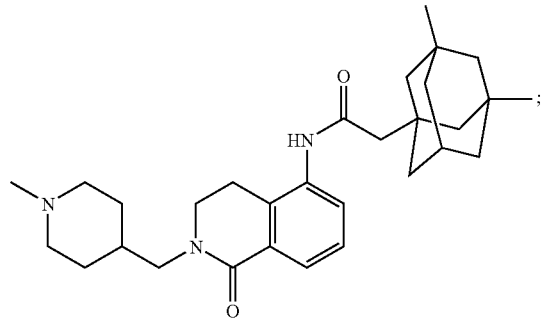 |

-continued

| Name | Structure |
|---|---|
| 2-(3,5-Dimethyl-adamantan-1-yl)-N-[2-(2-hydroxy-1-hydroxymethyl-ethyl)-1-oxo-1,2-dihydro-isoquinolin-5-yl]-acetamide | 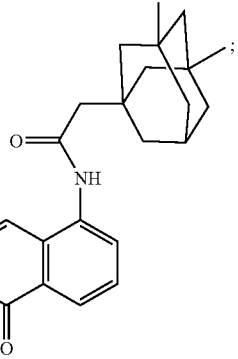 |
| 2-Adamantan-1-yl-N-[2-((S)-2-hydroxy-1-methyl-ethyl)-1-oxo-1,2-dihydro-isoquinolin-5-yl]-acetamide | 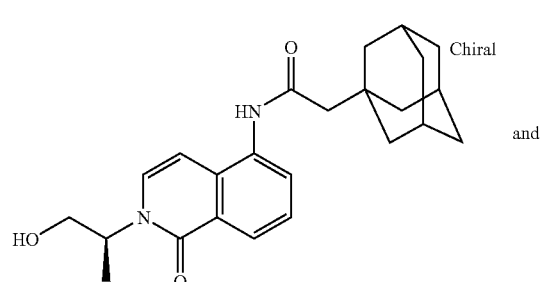 and |
| 2-Adamantan-1-yl-N-[2-((R)-2-hydroxy-1-methyl-ethyl)-1-oxo-1,2-dihydro-isoquinolin-5-yl]-acetamide | 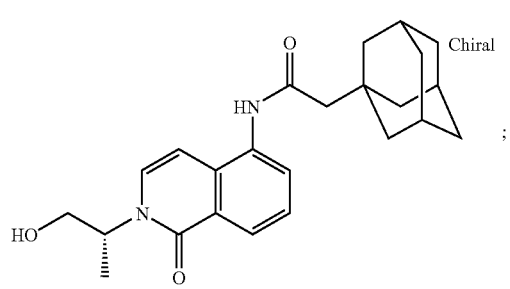 | or a pharmaceutically acceptable salt; and stereoisomers and tautomers thereof.

38. A pharmaceutical composition comprising a pharmaceutically acceptable carrier and a pharmaceutically effective amount of a compound of claim 1.

39. The pharmaceutical composition of claim 38, wherein the carrier is a parenteral carrier.

40. The pharmaceutical composition of claim 38, wherein the carrier is an oral carrier.

41. The pharmaceutical composition of claim 38, wherein the carrier is a topical carrier.

* * * * *